(12) United States Patent
Elliott et al.

(10) Patent No.: US 7,119,067 B2
(45) Date of Patent: Oct. 10, 2006

(54) HUMAN NEURONAL NICOTINIC ACETYLCHOLINE RECEPTOR COMPOSITIONS AND METHODS EMPLOYING SAME

(75) Inventors: Kathryn J. Elliott, San Diego, CA (US); Michael M. Harpold, El Cajon, CA (US)

(73) Assignee: Merck & Co., Inc., Rahway, NJ (US)

( * ) Notice: Subject to any disclaimer, the term of this patent is extended or adjusted under 35 U.S.C. 154(b) by 648 days.

(21) Appl. No.: 10/349,836

(22) Filed: Jan. 23, 2003

(65) Prior Publication Data

US 2003/0138911 A1    Jul. 24, 2003

Related U.S. Application Data

(60) Division of application No. 08/660,451, filed on Jun. 7, 1996, now Pat. No. 6,524,789, which is a continuation-in-part of application No. 08/484,722, filed on Jun. 7, 1995, now Pat. No. 6,485,967.

(51) Int. Cl.
*C07K 14/705* (2006.01)

(52) U.S. Cl. ........................ 514/12; 530/350

(58) Field of Classification Search .............. None
See application file for complete search history.

(56) References Cited

U.S. PATENT DOCUMENTS 5,837,489 A * 11/1998 Elliott et al. ............... 435/69.1

OTHER PUBLICATIONS

Elliott et al. *J. Mol. Neurosci.*, vol. 7, pp. 217-228, 1996, abstract only.*
Gerzanich et al. *Mol. Pharmacol.*, vol. 51, pp. 320-327, 1997, abstract only.*
Grinevich et al. *JPET*, vol. 312, pp. 619-626, 2005, abstract only.*
Quik et al., *Eur. J. Pharmacol.*, vol. 393, pp. 223-230, 2000, abstract only.*
Quik et al., *J PET*, vol. 316, pp. 481-489, 2006, abstract only.*

* cited by examiner

*Primary Examiner*—Lorraine Spector
*Assistant Examiner*—Stephen Gucker
(74) *Attorney, Agent, or Firm*—Vineet Kohli; Joanne M. Giesser

(57) ABSTRACT

Nucleic acid molecules encoding human neuronal nicotinic acetylcholine receptor alpha and beta subunits, mammalian and amphibian cells containing the nucleic acid molecules, and methods for producing alpha and beta subunits are provided. In particular, nucleic acid molecules encoding $\alpha_6$ subunits and molecules encoding $\beta_3$ subunits of human neuronal nicotinic acetylcholine receptors are provided. In addition, combinations of a plurality of subunits, such as one or more of $\alpha_1$, $\alpha_2$, $\alpha_3$, $\alpha_4$, $\alpha_5$, $\alpha_6$ and/or $\alpha_7$ subunits in combination with one or more of $\beta_3$ subunits or such as one or more of $\beta_2$, $\beta_3$ and/or $\beta_4$ subunits in combination with an $\alpha_6$ subunit are provided.

3 Claims, 2 Drawing Sheets

HUMAN NEURONAL NICOTINIC ACETYLCHOLINE RECEPTOR COMPOSITIONS AND METHODS EMPLOYING SAME

CROSS-REFERENCE TO RELATED APPLICATIONS

This application is a divisional of U.S. application Ser. No. 08/660,451, now U.S. Pat. No. 6,524,789 B1, filed Jun. 7, 1996, and is a continuation-in-part of U.S. application Ser. No. 08/484,722, now U.S. Pat. No. 6,485,967 B1, by Elliott et al., entitled "HUMAN NEURONAL NICOTINIC ACETYLCHOLINE RECEPTOR COMPOSITIONS AND METHODS EMPLOYING SAME", filed Jun. 7, 1995. The subject matter of U.S. Pat. No. 6,485,967 B1, is herein incorporated in its entirety by reference thereto.

STATEMENT REGARDING FEDERALLY-SPONSORED R&D

Not applicable.

REFERENCE TO MICROFICHE APPENDIX

Not applicable.

FIELD OF THE INVENTION

This invention relates to nucleic acid molecules encoding human neuronal nicotinic acetylcholine receptor protein subunits, as well as the encoded proteins. In particular, human neuronal nicotinic acetylcholine receptor α-subunit-encoding DNA and RNA, α-subunit proteins, β-subunit-encoding DNA and RNA, β-subunit proteins, and combinations thereof are provided.

BACKGROUND OF THE INVENTION

Ligand-gated ion channels provide a means for communication between cells of the central nervous system. These channels convert a signal (e., a chemical referred to as a neurotransmitter) that is released by one cell into an electrical signal that propagates along a target cell membrane. A variety of neurotransmitters and neurotransmitter receptors exist in the central and peripheral nervous systems. Five families of ligand-gated receptors, including the nicotinic acetylcholine receptors (nAChRs) of neuromuscular and neuronal origins, have been identified (Stroud et al. 1990 *Biochemistry* 29:11009–11023). There is, however, little understanding of the manner in which the variety of receptors generates different responses to neurotransmitters or to other modulating ligands in different regions of the nervous system.

The nicotinic acetylcholine receptors (nAChRs) are multisubunit proteins of neuromuscular and neuronal origins. These receptors form ligand-gated ion channels that mediate synaptic transmission between nerve and muscle and between neurons upon interaction with the neurotransmitter acetylcholine (ACh). Since various neuronal nicotinic acetylcholine receptor (nAChR) subunits exist, a variety of nAChR compositions (i.e., combinations of subunits) exist. The different nAChR compositions exhibit different specificities for various ligands and are thereby pharmacologically distinguishable. Thus, the nicotinic acetylcholine receptors expressed at the vertebrate neuromuscular junction, in vertebrate sympathetic ganglia and in the vertebrate central nervous system have been distinguished on the basis of the effects of various ligands that bind to different nAChR compositions. For example, the elapid α-neurotoxins that block activation of nicotinic acetylcholine receptors at the neuromuscular junction do not block activation of some neuronal nicotinic acetylcholine receptors that are expressed on several different neuron-derived cell lines.

Muscle nAChR is a glycoprotein composed of five subunits with the stoichimetry (α) 2β (γ or ε)δ. Each of the subunits has a mass of about 50–60 kilodaltons (kd) and is encoded by a different gene. The (α)2β (γ or ε)δ complex forms functional receptors containing two ligand binding sites and a ligand-gated transmembrane channel. Upon interaction with a cholinergic agonist, muscle nicotinic nAChRs conduct sodium ions. The influx of sodium ions rapidly short-circuits the normal ionic gradient maintained across the plasma membrane, thereby depolarizing the membrane. By reducing the potential difference across the membrane, a chemical signal is transduced into an electrical signal at the neuromuscular junction that induces muscle contraction.

Functional muscle nicotinic acetylcholine receptors have been formed with αβδγ subunits, αβγ subunits, αβδ subunits, αδγ subunits, but not only with one subunit (see, e.g., Kurosaki et al. (1987) *FEBS Lett.* 214 253–258; Comacho et al. (1993) *J. Neuroscience* 13:605–613). In contrast, functional neuronal nAChRs can be formed from α subunits alone or combinations of α and β subunits. The larger α subunit is generally believed to be a ACh-binding subunit and the lower molecular weight β subunit is generally believed to be the structural subunit, although it has not been definitely demonstrated that the β subunit does not have the ability to bind ACh or participate in the formation of the ACh binding site. Each of the subunits which participate in the formation of a functional ion channel are, to the extent they contribute to the structure of the resulting channel, "structural" subunits, regardless of their ability (or inability) to bind ACh. Neuronal nAChRs, which are also ligand-gated ion channels, are expressed in ganglia of the autonomic nervous system and in the central nervous system (where they mediate signal transmission), and in pre- and extra-synaptic locations (where they modulate neurotransmission and may have additional functions; Wonnacott et al. (1990) *In: progress in Brain Research*, A. Nordberg et al., Eds., Elsevier, Amsterdam) 157–163.

DNA encoding nAChRs has been isolated from several sources. Based on the information available from such work, it has been evident for some time that nAChRs expressed in muscle, in autonomic ganglia, and in the central nervous system are functionally diverse. This functional diversity could be due, at least in part, to the large number of different nAChR subunits which exist. There is an incomplete understanding, however, of how (and which) nAChR subunits combine to generate unique nAChR subtypes, particularly in neuronal cells. Indeed, there is evidence that only certain nAChR subtypes may be involved in disease such as Alzheimer's disease. Moreover, it is not clear whether nAChRs from analogous tissues or cell types are similar across species.

Accordingly, there is a need for the isolation and characterization of DNAs encoding each human neuronal nAChR subunit, recombinant cells containing such subunits and receptors prepared therefrom. In order to study the function of human neuronal nAChRs and to obtain disease-specific pharmacologically active agents, there is also a need to obtain isolated (preferably purified) human neuronal nAChRs, and isolated (preferably purified) human neuronal nAChR subunits. In addition, there is also a need to develop assays to identify such pharmacologically active agents.

The availability of such nucleic acids, cells, receptor subunits and receptor compositions will eliminate the uncertainty of speculating as to human neuronal nAChR structure and function based on predictions drawn from non-human nAChR data, or human or non-human muscle or ganglia nAChR data.

Therefore, it is an object herein to isolate and characterize DNA encoding subunits of human neuronal nicotinic acetylcholine receptors. It is also an object herein to provide methods for recombinant production of human neuronal nicotinic acetylcholine receptor subunits. It is also an object herein to provide purified receptor subunits and to provide methods for screening compounds to identify compounds that modulate the activity of human neuronal nAChRs.

These and other objects will become apparent to those of skill in the art upon further study of the specification and claims.

SUMMARY OF THE INVENTION

Isolated nucleic acid molecules encoding human alpha ($\alpha$) and beta°($\beta$) subunits of neuronal nAChRs are provided. In particular, isolated DNA and RNA molecules encoding human $\alpha_6$ and $\beta_3$ subunits of neuronal nAChRs are provided. Messenger RNA and polypeptides encoded by the DNA are also provided.

Recombinant human neuronal nicotinic nAChR subunits, including $\alpha_6$ and $\beta_3$ subunits, as well as methods for the production thereof are also provided. In addition, recombinant human neuronal nicotinic acetylcholine receptors containing at least one human neuronal nicotinic nAChR subunit are also provided, as well as methods for the production thereof. Also provided are recombinant neuronal nicotinic nAChRs that contain a mixture of one or more nAChR subunits encoded by a host cell, and one or more nAChR subunits encoded by heterologous DNA or RNA (i.e., DNA or RNA as described herein that has been introduced into the host cell), as well as methods for the production thereof.

Plasmids containing DNA encoding the above-described subunits are also provided. Recombinant cells containing the above-described DNA, mRNA or plasmids are also provided herein. Such cells are useful, for example, for replicating DNA, for producing human nAChR subunits and recombinant receptors, and for producing cells that express receptors containing one or more human subunits.

The DNA, RNA, vectors, receptor subunits, receptor subunit combinations and cells provided herein permit production of selected neuronal nicotinic nAChR receptor subtypes and specific combinations thereof, as well as antibodies to the receptor subunits. This provides a means to prepare synthetic or recombinant receptors and receptor subunits that are substantially free of contamination from many other receptor proteins whose presence can interfere with analysis of a single nAChR subtype. The availability of desired receptor subtypes makes it possible to observe the effect of a drug substance on a particular receptor subtype and to thereby perform initial in vitro screening of the drug substance in a test system that is specific for humans and specific for a human neuronal nicotinic nAChR subtype.

Also provided herein, are single-stranded probes containing portions of the DNA molecules described herein and antibodies that specifically bind to proteins encoded by the DNA. Also provided herein is an isolated nucleic acid molecule containing nucleotides 98–211 of SEQ ID NO:15.

Proteins encoded by the DNA are also provided. The proteins may be prepared by expressing the DNA in a suitable prokaryotic or eukaryotic host cell and isolating the resulting protein.

Methods for identifying functional neuronal nicotinic acetylcholine receptor subunits and combinations thereof are also provided.

Assays for identifying compounds that modulate the activity of human nicotinic acetylcholine receptors are also provided. The ability to screen drug substances in vitro to determine the effect of the drug on specific receptor compositions should permit the development and screening of receptor subtype-specific or disease-specific drugs. Also, testing of single receptor subunits or specific receptor subtype combinations with a variety of potential agonists or antagonists provides additional information with respect to the function and activity of the individual subunits and should lead to the identification and design of compounds that are capable of very specific interaction with one or more of the receptor subunits or receptor subtypes. The resulting drugs should exhibit fewer unwanted side effects than drugs identified by screening with cells that express a variety of subtypes.

Further in relation to drug development and therapeutic treatment of various disease states, the availability of DNA and RNA encoding human neuronal nAChR subunits provides a means for identification of any alterations in such genes (e.g., mutations) that may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

DETAILED DESCRIPTION OF THE INVENTION

Definitions

Figure 1:
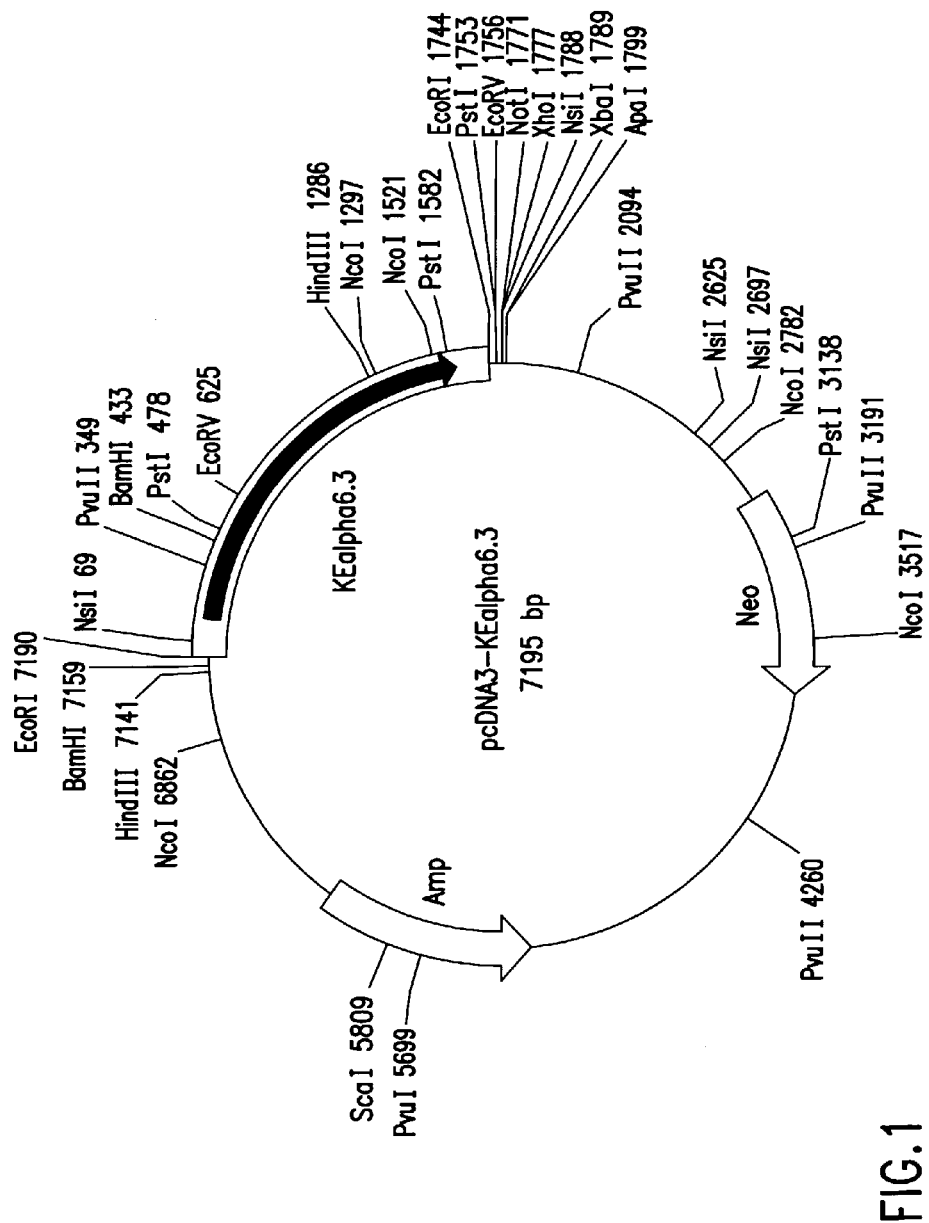
FIG. 1 presents a restriction map of a cytomegalovirus (CMV) promoter-based vector pcDNA3-KEalpha6.3 that contains an $\alpha_6$-encoding fragment as an EcoRI insert.

Unless defined otherwise, all technical and scientific terms used herein have the same meaning as is commonly understood by one of skill in the art to which this invention belongs. All patents and publications referred to herein are, unless noted otherwise, incorporated by reference in their entirety.

As used herein, isolated (or substantially purified or pure) as a modifier of nucleic acid molecule, DNA, RNA, polypeptides or proteins means that the DNA, RNA, polypeptides or proteins so-designated have been separated from their in vivo cellular environments through the hand of man. Thus, for example, as used herein, isolated (or substantially pure) DNA refers to DNA fragments purified according to standard techniques employed by those skilled in the art (see, e.g., Maniatis et al. (1982) *Molecular Cloning: A Laboratory Manual*, Cold Spring Harbor Laboratory Press, Cold Spring Harbor, N.Y.).

Similarly, as used herein, "recombinant" as a modifier of DNA, RNA, polypeptides or proteins means that the DNA, RNA, polypeptides or proteins so designated have been prepared by the efforts of human beings, e.g., by cloning, recombinant expression, or such method. Thus, as used herein, recombinant proteins, for example, refers to proteins produced by a recombinant host expressing DNAs which have been added to that host through the efforts of human beings.

As used herein, vector (or plasmid) refers to discrete elements that are used to introduce heterologous DNA into cells for either expression or replication thereof. Selection and use of such vehicles are well within the level of skill of the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as plasmid, a phage, recombinant virus or other vector that, upon introduction to a host cell, allows expression of DNA cloned into the appropriate site on the vector. Appropriate expression vectors are well known to those of skill in the art and include those that are replicable in eukaryotic cells and/or prokaryotic cells and those that remain episomal or those which integrate into the host cell genome. Presently preferred plasmids for expression of the nAChR subunits in eukaryotic host cells, particularly mammalian cells, include, but are not limited to, cytomegalovirus (CMV), Simian virus 40 (SV40) and mouse mammary tumor virus (MMTV) promoter-containing vectors such as pCMV, pcDNA1, pcDNA3, pZeoSV, pCEP4, pMAMneo and pMAMhyg.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use herein include the SV40 early promoter, the cytomegalovirus (CMV) promoter, the mouse mammary tumor virus (MMTV) steroid-inducible promoter, and Moloney murine leukemia virus (MMLV) promoter, and other suitable promoters.

As used herein, the term "operatively linked" refers to the functional relationship of DNA with regulatory and effector sequences of nucleotides, such as promoters, enhancers, transcriptional and translational start and stop sites, and other signal sequences. For example, operative linkage of DNA to a promoter refers to the physical and functional relationship between the DNA and the promoter such that the transcript of such DNA is initiated from the promoter by an RNA polymerase that specifically recognizes, binds to and transcribes the DNA. In order to optimize expression and/or in vitro transcription, it may be necessary to remove or alter 5' untranslated portions of the clones to remove extra, potential alternative translation initiation (i.e., start) codons or other sequences that interfere with or reduce expression, either at the level of transcription or translation. Alternatively, consensus ribosome binding sites (see, for example, Kozak (1991) *J. Biol. Chem.* 266:19867–19870) can be inserted immediately 5' of the start codon to enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the SV40 promoter-based expression vectors, such as pZeoSV (Invitrogen, San Diego, Calif.), CMV promoter-based vectors such as pcDNA1, pcDNA3, pCEP4 (Invitrogen, San Diego, Calif.), and MMTV promoter-based vectors such as pMAMneo (Clontech, Inc.).

As used herein, a human alpha ($\alpha$) subunit gene is a gene that encodes an alpha subunit of a human neuronal nicotinic acetylcholine receptor. Alpha subunits of human nAChRs typically exhibit a conservation of adjacent cysteine residues in the presumed extracellular domain of the subunit that are the homologs of cysteines 192 and 193 of the Torpedo alpha subunit (see Noda et al. (1982) *Nature* 299:793–797).

As used herein, an alpha subunit subtype refers to a human neuronal nAChR subunit that is encoded by DNA that hybridizes under high stringency conditions to at least one of the neuronal nAChR alpha subunit-encoding DNA clones disclosed herein. An alpha subunit generally binds to ACh under physiological conditions and at physiological concentrations and, in the optional presence of a beta subunit (i.e., some alpha subunits are functional alone, while others require the presence of a beta subunit), generally forms a functional nAChR as assessed by methods described herein or known to those of skill in this art.

Also contemplated are alpha subunits encoded by DNA molecules that encode alpha subunits as defined above, but that by virtue of degeneracy of the genetic code do not necessarily hybridize to the disclosed DNA under specified hybridization conditions. Such subunits also form a functional receptor, as assessed by the methods described herein or known to those of skill in the art, generally with one or more beta subunit subtypes. Typically, unless an alpha subunit is encoded by RNA that arises from alternative splicing (i.e., a splice variant), alpha-encoding DNA and the alpha subunit encoded thereby share substantial sequence homology with at least one of the alpha subunit DNAs (and proteins encoded thereby) described herein. It is understood that DNA or RNA encoding a splice variant may overall share less than 90% homology with the DNA or RNA provided herein, but include regions of nearly 100% homology to a DNA fragment described herein, and encode an open reading frame that includes start and stop codons and encodes a functional alpha subunit.

As used herein, a human beta ($\beta$) subunit gene is a gene that encodes a beta subunit of a human neuronal nicotinic acetylcholine receptor. Assignment of the name "beta" to a putative neuronal nAChR subunit has been based on the lack of adjacent cysteine residues (which residues are characteristic of alpha subunits). The beta subunit is frequently referred to as the structural nAChR subunit (although it is possible that beta subunits also have ACh binding properties). Combination of the appropriate beta subunit(s) with appropriate alpha subunit(s) leads to the formation of a functional receptor.

As used herein, a beta subunit subtype refers to a neuronal nAChR subunit that is encoded by DNA that hybridizes under high stringency conditions to at least one of the neuronal nAChR-encoding DNAs disclosed herein. A beta subunit may form a functional nAChR, as assessed by methods described herein or known to those of skill in this art, with appropriate alpha subunit subtype(s).

Also contemplated are beta subunits encoded by DNA that encodes beta subunits as defined above, but that by virtue of degeneracy of the genetic code do not necessarily hybridize to the disclosed DNA under the specified hybridization conditions. Such subunits may also form functional receptors, as assessed by the methods described herein or known to those of skill in the art, in combination with appropriate alpha subunit subtype(s). Typically, unless a beta subunit is encoded by RNA that arises as a splice variant, beta-encoding DNA and the beta subunit encoded thereby share substantial sequence homology with the beta-encoding DNA and beta subunit protein described herein. It is understood that DNA or RNA encoding a splice variant may share less that 90% overall homology with the DNA or RNA provided herein, but such DNA will include regions of nearly 100% homology to the DNA described herein.

As used herein, a nAChR subtype refers to a nicotinic acetylcholine receptor containing a particular combination of α and/or β subunit subtypes, e.g., a receptor containing human nAChR $\alpha_6$ and $\beta_3$ subunits.

As used herein, a splice variant refers to variant nAChR subunit-encoding nucleic acid(s) produced by differential processing of primary transcript(s) of genomic DNA, resulting in the production of more than one type of mRNA. cDNA derived from differentially processed genomic DNA will encode nAChR subunits that have regions of complete amino acid identify and regions having different amino acid sequences. Thus, the same genomic sequence can lead to the production of multiple, related mRNAs and proteins. The resulting mRNA and proteins are referred to as "splice variants".

As used herein, heterologous or foreign DNA and RNA are used interchangeably and refer to DNA or RNA that does not occur naturally as part of the genome in which it is present or which is found in a location or locations in the genome that differ from that in which it occurs in nature. It is typically DNA or RNA that is not endogenous to the cell and has been artificially introduced into the cell. Examples of heterologous DNA include, but are not limited to, DNA that encodes a human nAChR subunit and DNA that encodes RNA or proteins that mediate or alter expression of endogenous DNA by affecting transcription, translation, or other regulatable biochemical processes. The cell that expresses the heterologous DNA, such as DNA encoding a human nAChR subunit, may contain DNA encoding the same or different nicotinic acetylcholine receptor subunits. The heterologous DNA need not be expressed and may be introduced in a manner such that it is integrated into the host cell genome or is maintained episomally.

Stringency of hybridization is used herein to refer to conditions under which polynucleic acid hybrids are stable. As known to those of skill in the art, the stability of hybrids is reflected in the melting temperature ($T_m$) of the hybrids. Tm can be approximated by the formula:

$$81.5° C.-16.6 (\log_{10}[Na^+])+0.41 (\% G+C)-600/1,$$

where 1 is the length of the hybrids in nucleotides. $T_m$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein:

(1) HIGH STRINGENCY conditions, with respect to fragment hybridization, refer to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhardt's solution, 5×SSPE, 0.2% SDS, 200 µg/ml denaturated sonicated herring sperm DNA, at 42° C., followed by washing in 0.1× SSPE, and 0.1% SDS at 65° C.;

(2) MODERATE STRINGENCY conditions, with respect to fragment hybridization, refer to conditions equivalent to hybridization in 50% formamide, 5× Denhardt's solution, 5×SSPE, 0.2% SDS, 200 µg/ml denatured sonicated herring sperm DNA, at 42° C., followed by washing in 0.2×SSPE, 0.2% SDS, at 60° C.;

(3) LOW STRINGENCY conditions, with respect to fragment hybridization, refer to conditions equivalent to hybridization in 10% formamide, 5× Denhardt's solution, 6×SSPE, 0.2% SDS, 200 µg/ml denatured sonicated herring sperm DNA, followed by washing in 1×SSPE, 0.2% SDS, at 50° C.; and (4) HIGH STRINGENCY conditions, with respect to oligonucleotide (i.e., synthetic DNA≦about 30 nucleotides in length) hybridization, refer to conditions equivalent to hybridization in 10% formamide, 5× Denhardt's solution, 6×SSPE, 0.2% SDS, 200 µg/ml denatured sonicated herring sperm DNA, at 42° C., followed by washing in 1×SSPE, and 0.2% SDS at 50° C.

It is understood that these conditions may be duplicated using a variety of buffers and temperatures and that they are not necessarily precise.

Denhardt's solution and SSPE (see, e.g., Sambrook et al. (1989) *Molecular Cloning: A Laboratory Manual,* 2nd Ed., Cold Spring Harbor Laboratory Press, Cold Spring Harbor, N.Y.) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhardt's solution (see, Denhardt (1966) *Biochem. Biohphys. Res. Commun.* 23:641) can be prepared, for example, as a 50×stock solution by mixing 5 g Ficoll (Type 400, Pharmacia LKB Biotechnology, INC., Piscataway N.J.), 5 g of polyvinylpyrrolidone, 5 g bovine serum albumin (Fraction V; Sigma, St. Louis Mo.) water to 500 ml and filtering to remove particulate matter.

As used herein, the phrase "substantial sequence homology" refers to two sequences of nucleotides that share at least about 90% identity, and amino acid sequences which typically share greater than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated herein.

The phrase "substantially the same" is used herein in reference to the nucleotide sequence of DNA, the ribonucleotide sequence of RNA, or the amino acid sequence or protein, that have slight and non-consequential sequence variations from the actual sequences disclosed herein. Species that are substantially the same are considered to be functionally equivalent to the disclosed sequences. Thus, as used herein functionally equivalent nucleic acid molecules or proteins are those that are sufficiently similar to function in substantially the same manner to achieve substantially the same results.

As used herein, "slight and non-consequential sequence variations" mean that sequences that are substantially the same as the DNA, RNA, or proteins disclosed and claimed herein are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNA molecules encode human-derived proteins that are the same as those disclosed herein or that have conservative amino acid variations, such as substitution of a non-polar residue for another non-polar residue or a charged residue for a similarly charged residue (see, e.g., Table 1). These changes include those recognized by those of skill in the art as those that do not substantially alter the tertiary structure of the protein.

Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. co., p.224). Such substitutions are preferably made in accordance with those set forth in TABLE 1 as follows:

TABLE 1

| Ala (A) | Gly; Ser |
| --- | --- |
| Arg (R) | Lys |
| Asn (N) | Gln; His |
| Cys (C) | Ser; neutral amino acids |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Glny; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

Any such modification of the polypeptide may be effected by any means known to those of skill in this art.

As used herein, activity of a human neuronal nAChR refers to any activity characteristic of an nAChR. Such activity can typically be measured by one or more in vitro methods, and frequently corresponds to an in vivo activity of a human neuronal nAChR. Such activity may be measured by any method known to those of skill in the art, such as, for example, measuring the amount of current which flows through the recombinant channel in response to a stimulus.

Methods to determine the presence and/or activity of human neuronal nAChRs include, but are not limited to, assays that measure nicotine binding, $^{86}$Rb ion-flux, $Ca^{2+}$ influx, the electrophysiological response of cells, the electrophysiological response of oocytes injected with RNA. In particular, methods are provided herein for the measurement or detection of an nAChR-mediated response upon contact of cells containing the DNA or mRNA with a test compound.

As used herein, a recombinant or heterologous human neuronal nAChR refers to a receptor that contains one or more subunits encoded by heterologous DNA that has been introduced into and expressed in cells capable of expressing receptor protein. A recombinant human neuronal nAChR may also include subunits that are produced by DNA endogenous to the host cell. In certain embodiments, recombinant or heterologous human neuronal nAChR may contain only subunits that are encoded by heterologous DNA.

As used herein, a functional neuronal nAChR is a receptor that exhibits an activity of neuronal nicotinic nAChRs as assessed by any in vitro or in vivo assay disclosed herein or known to those of skill in the art. Possession of any such activity that may be assessed by any methods known to those of skill in the art and provided herein is sufficient to designate a receptor as functional. Methods for detecting nAChR protein and/or activity include, but are not limited to, for example, assays that measure nicotine binding, $^{86}$Rb ion-flux, $Ca^{2+}$ influx and the electrophysiological response of cells containing heterologous DNA or mRNA encoding one or more receptor subunit subtypes. Since all combinations of alpha and beta subunits may not form functional receptors, numerous combinations of alpha and beta subunits may be tested in order to fully characterize a particular subunit and cells which produce same. Thus, as used herein, "functional" with respect to a recombinant or heterologous human neuronal nAChR means that the receptor channel is able to provide for and regulate entry of human neuronal nAChR-permeable ions, such as, for example, $Na^+$, $K^+$, $Ca^{2+}$ or $Ba^{2+}$, in response to a stimulus and/or bind ligands with affinity for the receptor. Preferably such human neuronal nAChR activity is distinguishable, such as by electrophysiological, pharmacological and other means known to those of skill in the art, from any endogenous nAChR activity that may be produced by the host cell.

As used herein, one type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional nicotinic acetylcholine receptors. In this situation, the response of test cell to the test compound is compared to the response (or lack of response) of the nicotinic acetylcholine receptor-negative cell to the test compound, when cells or cultures of each type of cell are exposed to substantially the same reaction conditions in the presence of the compound being assayed.

As used herein, a compound or signal that "modulates the activity of a neuronal nAChR" refers to a compound or signal that alters the activity of nAChR so that activity of the nAChR is different in the presence of the compound or signal than in the absence of the compound or signal. In particular, such compounds or signals include agonists and antagonists. The term agonist refers to a substance or signal, such as ACh, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

A. Isolated DNA Clones

DNA molecules encoding human alpha and beta subunits of neuronal nAChRs are provided. Specifically, isolated DNAs encoding $\alpha_6$ and $\beta_3$ subunits of human neuronal nAChRs are described herein. Recombinant messenger RNA (mRNA) and recombinant polypeptides encoded by the above-described DNA are also provided.

For purposes herein, "$\alpha_6$ subunit-encoding nucleic acid" refers to DNA or RNA encoding a neuronal nicotinic acetylcholine receptor subunit of the same name. Such nucleic acid molecules can be characterized in a number of ways, for example the nucleotides of the DNA (or ribonucleotides of the RNA) may encode the amino acid sequence set forth in SEQ ID NO:10 or SEQ ID NO:20.

Presently preferred $\alpha_6$-encoding nucleic acid includes DNA or RNA that hybridizes to the coding sequence set forth in SEQ ID NO:9 (preferably to substantially the entire coding sequence thereof, i.e., nucleotides 143–1624) or SEQ ID NO:19 (preferably to substantially the entire coding sequence thereof, i.e., nucleotides 143–1579) under high stringency conditions.

Especially preferred $\alpha_6$-encoding nucleic acid molecules are those that encode a protein having substantially the same amino acid sequence (i., with only conservative amino acid substitutions) as that set forth in SEQ ID NO:10 or SEQ ID NO:20. Most preferred molecules include a sequence of nucleotides (or ribonucleotides with U substituted for T) having substantially the same sequence of nucleotides as set forth in SEQ ID NO:9 (i.e., particularly nucleotides 143–1624 thereof) or SEQ ID NO:19 (i.e., particularly nucleotides 143–1579 thereof).

Typically, unless an $\alpha_6$ subunit arises as a splice variant, $\alpha_6$-encoding DNA will share substantial sequence homology (i.e. greater than about 90%), with a $\alpha_6$-encoding nucleic acid molecules described herein. DNA or RNA encoding a splice variant may share less than 90% overall sequence homology with the DNA or RNA provided herein, but such a splice variant would include regions of nearly 100% homology to one or more of the nucleic acid molecules provided herein.

Also provided herein are "$\beta_3$ subunit-encoding nucleic acids", which include DNA or RNA molecules that encode a neuronal nicotinic acetylcholine receptor subunit of the same name. Such nucleic acid molecules can be characterized in a number of ways, for example, the nucleotides of the DNA (or ribonucleotides of the RNA) may encode the amino acid sequence set forth in SEQ ID NO:16.

Presently preferred $\beta_3$-encoding nucleic acid includes DNA or RNA that hybridizes under high stringency conditions to the coding sequence set forth in SEQ ID NO:15 (preferably to substantially the entire coding sequence thereof, i.e., nucleotides 98–1471). More preferred are those nucleic acids that encode a protein that includes the sequence of amino acids (or substantially the sequence of amino acids with only conservative amino acid substitutions) set forth in SEQ ID NO:16. Especially preferred $\beta_3$-encoding nucleic acid molecules provided herein have substantially the same nucleotide sequence as set forth in SEQ ID NO:15 (i.e., particularly nucleotides 98–1471 thereof).

Typically, unless a $\beta_3$ subunit arises as a splice variant, $\beta_3$-encoding nucleic acid will share substantial sequence homology (greater than about 90%) with the $\beta_3$-encoding nucleic acid molecules described herein. DNA or RNA encoding a splice variant may share less than 90% overall sequence homology with the DNA or RNA provided herein, but such nucleic would include regions of nearly 100% homology to one or more of the above-described nucleic acid molecules.

B. Probes

DNA encoding human neuronal nicotinic nAChR alpha and beta subunits may be isolated by screening suitable human cDNA or human genomic libraries under suitable hybridization conditions with the DNA disclosed herein (including nucleotides derived from SEQ ID NOs:9 or 15). Suitable libraries can be prepared from tissues such as neuronal tissue samples, basal ganglia, thalamus, and hypothalamus tissues. The library is preferably screened with a portion of DNA including the entire subunit-encoding sequence thereof, or the library may be screened with a suitable probe. Typically probes are labeled with an identifiable tag, such as a radiolabel, enzyme or other such tag known to those of skill in the art.

Probes for use in methods of isolating $\alpha_6$- and $\beta_3$-encoding nucleic acids are also provided. Thus, for example, with reference to human $\alpha_6$ subunits, a probe is a single-stranded DNA or RNA molecule that has a sequence of nucleotides that includes at at least 27 contiguous bases that are the same as (or the complement of) any 27 bases set forth in SEQ ID NO:9 or SEQ ID NO:19.

With reference to human $\beta_3$ subunits, a probe is single-stranded DNA or RNA that has a sequence of nucleotides that includes at least 28 contiguous bases that are the same as (or the complement of) any 28 bases derived from the first 105 nucleotides of signal sequence/coding sequence set forth in SEQ ID NO:15.

Among the preferred regions from which to construct probes include, but are not limited to, 5' and/or 3' coding sequences, regions containing sequences predicted to encode transmembrane domains, regions containing sequences predicted to encode a cytoplasmic loop, signal sequences, and acetylcholine (ACh) and α-bungarotoxin (α-bgtx) binding sites. Amino acids that correspond to residues 190-198 of the Torpedo nAChR α subunit (see, e.g., Karlin (1993) *Curr. Opin. Neurobiol.* 3:299–309) are typically involved in ACh and α-bgtx binding. The approximate amino acid residues which include such regions for other probes are set forth in the following table, Table 2:

| Subunit | Signal Sequence | TMD1* | TMD2 | TMID3 | TMD4 | Cytoplasmic loop |
|---|---|---|---|---|---|---|
| $\alpha_6$# | 1–30 | 240–265 | 272–294 | 301–326 | 458–483 | 327–457 |
| $\beta_3$ | 1–20 | 231–258 | 265–287 | 293–318 | 421–446 | 319–420 |

*TMD = transmembrane domain
With reference to the amino acid sequence shown in SEQ ID NO: 10.

Alternatively, portions of the DNA can be used as primers to amplify selected fragments in a particular library.

C. Isolation of Clones Encoding $\alpha_6$ and $\beta_3$ Subunits of Human Neuronal Nicotinic Acetylcholine Receptors The probes are used to screen a suitable library. Suitable libraries for obtaining DNA encoding each subunit include, but are not limited to: substantia nigra, thalamus or hypothalamus to isolate human $\alpha_6$-encoding DNA and substantia nigra or thalamus to isolate human $\beta_3$-encoding DNA.

After screening the library, positive clones are identified by detecting a hybridization signal; the identified clones are characterized by restriction enzyme mapping and/or DNA sequence analysis, and then examined, by comparison with the sequences set forth herein, to ascertain whether they include DNA encoding a complete alpha or beta subunit. If the selected clones are incomplete, the may be used to rescreen the same or a different library to obtain overlapping clones. If desired, the library can be rescreened with positive clones until overlapping clones that encode an entire alpha or beta subunit are obtained. If the library is a cDNA library, then the overlapping clones will include an open reading frame. If the library is genomic, then the overlapping clones may include exons and introns. Complete clones may be identified by comparison with the DNA and encoded proteins provided herein.

Complementary DNA clones encoding various subtypes of human neuronal nAChR alpha and beta subunits have been isolated. Each subtype of the subunit appears to be encoded by a different gene. The DNA clones provided herein may be used to isolate genomic clones encoding each subtype and to isolate any splice variants by screening libraries prepared from different neural tissues. Nucleic acid amplification techniques, which are well known in the art, can be used to locate splice variants of human neuronal nAChR subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human neuronal nAChR subunits.

It has been found that not all subunit subtypes are expressed in all neural tissues or in all portions of the brain. Thus, in order to isolate cDNA encoding particular subunit subtypes or splice variants of such subtypes, it is preferable to screen libraries prepared from different neuronal or neural tissues.

D. Cells and Vectors Containing $\alpha_6$- and $\beta_3$-encoding Nucleic Acids The above-described nucleic acid molecules encoding human nAChR subunits can be incorporated into vectors for further manipulation. Incorporation of cloned DNA into a suitable expression vector, transfection of eukaryotic cells with one or a combination of expression constructs encoding one or more distinct genes or with linear DNA, and selection of transfected cells are well known in the art (see, e.g., Sambrook et al. (1989) *Molecular Cloning: A Laboratory Manual,* 2nd Ed., Cold Spring Harbor Laboratory Press, Cold Spring Harbor, N.Y.).

Heterologous DNA may be introduced into host cells by any method known to those of skill in the art, such as transfection with an expression construct encoding the heterologous DNA by CaPO4 precipitation (see, e.g., Wigler et al. (1979) *Proc. Natl. Acad. Sci. U.S.A.* 76:1373–1376). Recombinant cells can then be cultured under conditions whereby the subunit(s) encoded by the DNA is (are) expressed. Preferred cells include, but are not limited to, mammalian cells (e.g., HEK 293, CHO and Ltk cells), yeast cells (e.g., methylotrophic yeast cells, such as *Pichia pastoris*) and bacterial cells (e.g., *Escherichia coli*).

The nucleic acids encoding $\alpha_6$ or $\beta_3$ subunits can be incorporated into vectors individually or in combination with nucleic acids encoding other nicotinic acetylcholine receptor subunits for further manipulation. Full-length DNA clones encoding human neuronal nAChR subunits have been inserted into vector pcDNA3, a pUC19-based mammalian cell expression vector containing the CMV promoter/enhancer, a polylinker downstream of the CMV promoter/enchancer, followed by the bovine growth hormone (BGH) polyadenylation signal. Placement of nAChR subunit-encoding DNA between the CMV promoter and BGH polyadenylation signal provides for constitutive expression of the DNA in a mammalian host cell transfected with the construct. For inducible expression of human nAChR subunit-encoding DNA in a mammalian cell, the DNA can be inserted into a plasmid such as pMAMneo. This plasmid contains the mouse mammary tumor virus (MMTV) promoter for steroid-inducible expression of operatively associated foreign DNA. If the host cell does not express endogenous glucocorticoid receptors required for uptake of glucocorticoids (i.e., inducers of the MMTV promoter) into the cell, it is necessary to additionally transfect the cell with DNA encoding the glucocorticoid receptor (ATCC accession no. 67200).

In accordance with another embodiment, there are provided cells containing the above-described polynucleic acids (i.e., DNA or mRNA). Host cells such as bacterial, yeast and mammalian cells can be used for replicating DNA and producing nAChR subunit(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/02311, PCT/US94/02447, PCT/US91/05625, and PCT/US92/11090, in U.S. Pat. No. 5,369,028, and in co-pending U.S. application Ser. Nos. 07/563,751 and 07/812,254. The subject matter of these applications is hereby incorporated by reference herein in its entirety.

While the DNA provided herein may be expressed in any eukaryotic cell, including yeast cells (such as, for example, Pichia, particularly *Pichia pastoris* (see U.S. Pat. Nos. 4,882,279, 4,837,148, 4,929,555 and 4,855,231), *Saccharomyces cerevisiae, Candida tropicalis, Hansenula polymorpha,* and other yeast cells), mammalian expression systems, including commercially available systems and other such systems known to those of skill in the art, for expression of DNA encoding the human neuronal nicotinic nAChR subunits provided herein are presently preferred. Xenopus oocytes are preferred for expression of RNA transcripts of the DNA.

Cloned full-length DNA encoding any of the subunits of human neuronal nicotinic nAChR may be introduced into a plasmid vector for expression in a eukaryotic cell. Such DNA may be genomic DNA or cDNA. Host cells may be transfected with one or a combination of plasmids, each of which encodes at least one human neuronal nAChR subunit. Heterologous DNA may be maintained in the cell as an episomal element or may be integrated into chromosomal DNA of the cell.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human neuronal nicotinic nAChRs containing one or more subunits encoded by the heterologous DNA.

Such cells may be identified empirically or selected from among those known to be readily transfected or injected.

Exemplary cells for introducing DNA include, but are not limited to, cells of mammalian origin (e.g., COS cells, mouse L cells, Chinese hamster ovary (CHO) cells, human embryonic kidney (HEK) cells, GH3 cells and other such cells known to those of skill in the art, amphibian cells (e., *Xenopus laevis* oocytes) and yeast cells (e.g., *Saccharomyces cerevisiae, Pichia pastoris*). Exemplary cells for expressing injected RNA transcripts include *Xenopus laevis* oöcytes. Cells that are preferred for transfection of DNA are known to those of skill in the art or may be empirically identified, and include HEK 293 (which are available from ATCC under accession #CRL 1573); Ltk⁻ cells (which are available from ATCC under accession #CCL1.3); COS-7 cells (which are available from ATCC under accession #CRL 1651); and GH3 cells (which are available from ATCC under accession #CCL82.1). Presently preferred cells include GH3 cells and HEK 293 cells, particularly HEK 293 cells that have been adapted for growth in suspension and that can be frozen in liquid nitrogen and then thawed and regrown. HEK 293 cells are described, for example, in U.S. Pat. No. 5,024,939 to Gorman (see, also, Stillman et al., (1985) *Mol. Cell. Biol.* 5:2051–2060).

DNA can be stably incorporated into cells or may be transiently introduced using methods known in the art. Stably transfected mammalian cells may be prepared by transfecting cells either with one or more expression constructs carrying DNA encoding nAChR subunits and a separate expression vector carrying a selectable marker gene (e.g., but not limited to, the gene for neomycin resistance, zeocin resistance, or hygromycin resistance) or with one or more expression constructs which carry the DNA encoding nAChR subunit and the selectable marker, and growing the transfected cells under conditions selective for cells expressing the marker gene(s). To produce such cells, the cells should be transfected with a sufficient concentration of subunit-encoding nucleic acids to form human neuronal nAChRs that contain the human subunits encoded by heterologous DNA. The precise amounts and ratios of DNA encoding the subunits may be empirically determined and optimized for a particular combination of subunits, cells and assay conditions. Recombinant cells that express neuronal nAChR containing subunits encoded only by the heterologous DNA or RNA are especially preferred.

E. Recombinant nAChRs and nAChR Subunit Proteins

Provided herein are substantially pure human nAChR subunit proteins, particularly human $\alpha_6$ and $\beta_3$ subunit proteins. Also provided herein are recombinant nAChR containing at least one of the human nAChR subunit proteins. Thus, a further embodiment provided herein contains methods of producing recombinant human nAChR subunits and receptors containing the subunits.

In preferred embodiments, DNA encoding human nAChR subunit(s), particularly human nAChR $\alpha_6$ and/or $\beta_3$ subunits, is ligated into a vector, and the resulting construct is introduced into suitable host cells to produce transformed cell lines that express a specific human neuronal nAChR receptor subtype, or specific combinations of subtypes. The resulting cell lines can then be produced in quantity for reproducible quantitative analysis of the effects of drugs on receptor function. In other embodiments, mRNA may be produced by in vitro transcription of DNA encoding each subunit. This mRNA, either from a single subunit clone or from a combination of clones, can then be injected into *Xenopus oocytes* where the mRNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

The resulting recombinant cells may be cultured or subcultured (or passaged, in the case of mammalian cells) from such a culture or a subculture thereof. Methods for transfection, injection and culturing recombinant cells are known to the skilled artisan. Similarly, the human neuronal nicotinic nAChR subunits may be purified using protein purification methods known to those of skill in the art. For example, antibodies or other ligands that specifically bind to one or more of the subunits may be used for affinity purification of the subunit or human neuronal nAChRs containing the subunits.

In accordance with one embodiment, methods for producing cells that express human neuronal nAChR subunits and functional receptors are also provided. In one such method, host cells are transfected with DNA encoding at least one alpha subunit of a neuronal nAChR and at least one beta subunit of neuronal nAChR. Using methods such as northern blot or slot blot analysis, transfected cells that contain alpha and/or beta subunit encoding DNA or RNA can be selected. Transfected cells are also analyzed to identify those that express nAChR protein. Analysis can be carried out, for example, by measuring the ability of cells to bind acetylcholine, nicotine, or a nAChR agonist, compared to the nicotine binding ability of untransfected host cells or other suitable control cells, or by electrophysiologicaly monitoring the currents through the cell membrane in response to a nAChR agonist.

In particularly preferred aspects, eukaryotic cells that contain heterologous DNA, express such DNA and form recombinant functional neuronal nAChR(s) are provided. In more preferred aspects, recombinant neuronal nAChR activity is readily detectable because it is a type that is absent from the untransfected host cell or is of a magnitude not exhibited in the untransfected cell. Such cells that contain recombinant receptors could be prepared, for example, by causing cells transformed with DNA encoding the human neuronal nicotinic nAChR $\alpha_6$ and $\beta_3$ subunits to express the corresponding proteins in the presence or absence of one or more alpha and/or beta nAChR subunits. The resulting synthetic or recombinant receptor would contain the ($\alpha_6$ and $\beta_3$ nAChR subunits. Such a receptor would be useful for a variety of applications, e.g., as part of an assay system free of the interferences frequently present in prior art assay systems employing non-human receptors or human tissue preparations. Furthermore, testing of single receptor subunits with a variety of potential agonists or antagonists would provide additional information with respect to the function and activity of the individual subunits. Such information may lead to the identification of compounds which are capable of very specific interaction with one or more of the receptor subunits. Such specificity may prove of great value in medical application.

Thus, DNA encoding one or more human neuronal nAChR subunits may be introduced into suitable host cells (e.g., eukaryotic or prokaryotic cells) for expression of individual subunits and functional nAChRs. Preferably combinations of alpha and beta subunits may be introduced into cells: such combinations include combinations of any one or more of $\alpha_2$, $\alpha_3$, $\alpha_4$, $\alpha_5$, $\alpha_6$ and $\alpha_7$ with $\beta_2$, $\beta_3$ and/or $\alpha_4$. Sequence information for each of these subunits is presented in the Sequence Listing provided herewith. Sequence information for $\alpha_5$ is also presented in *Proc. Natl. Acad. Sci. USA* (1992) 89:1572–1576; sequence information for $\alpha_2$, $\alpha_3$, $\alpha_4$, $\alpha_7$, $\beta_2$ and $\beta_4$ is also presented in PCT publication WO 94/20617, incorporated by reference herein. Presently preferred combinations of subunits include $\alpha_6$ and/or $\beta_3$ with any one or more of $\alpha_2$, $\alpha_3$, $\alpha_4$, $\alpha_5$, $\beta_2$ or $\beta_4$. It is recognized that some of the subunits may have ion transport function in the absence of additional subunits, while others require a combination of two or more subunits in order to display ion transport function. For example, the $\alpha_7$ subunit is functional in the absence of any added beta subunit. Furthermore, some of the subunits may not form functional nAChRs alone or in combination, but instead may modulate the properties of other nAChR subunit combinations.

In certain embodiments, eukaryotic cells with heterologous human neuronal nAChRs are produced by introducing into the cells a first composition, which contains at least one RNA transcript that is translated in the cell into a subunit of a human neuronal nAChR. In preferred embodiments, the subunits that are translated include an alpha subunit of a human neuronal nAChR. More preferably, the composition that is introduced contains a RNA transcript which encodes an alpha subunit and also contains a RNA transcript which encodes a beta subunit of a human neuronal nAChR. RNA transcripts can be obtained from cells transfected with DNAs encoding human neuronal nAChR subunits or by in vitro transcription of subunit-encoding DNAs. Methods for in vitro transcription of cloned DNA and injection of the resulting mRNA into eukaryotic cells are well known in the art. Amphibian oocytes are particularly preferred for expression of in vitro transcripts of the human neuronal nAChR DNA clones. See e.g. Dascal (1989) *CRC Crit. Rev. Biochem.* 22:317–387, for a review of the use of *Xenopus* oocytes to study ion channels.

Thus, a stepwise introduction into cells of DNA or RNA encoding one or more alpha subtypes, and one or more beta subtypes is possible. The resulting cells may be tested by the methods provided herein or known to those of skill in the art to detect functional nAChR activity. Such testing will allow the identification of combinations of alpha and beta subunit subtypes that produce functional nAChRs, as well as individual subunits that produce functional nAChRs.

Recombinant receptors on recombinant eukaryotic cell surfaces may contain one or more subunits encoded by the DNA or mRNA encoding human neuronal nAChR subunits, or may contain a mixture of subunits encoded by the host cell and subunits encoded by heterologous DNA or mRNA. Recombinant receptors may be homogeneous or may be a mixture of subtypes. Mixtures of DNA or mRNA encoding receptors from various species, such as rats and humans, may also be introduced into the cells. Thus, a cell may be prepared that expresses recombinant receptors containing only $\alpha_6$ and $\ominus_3$ subunits, or in combination with any other alpha and beta subunits provided herein. For example, either or both of the $\alpha_6$ and $\beta_3$ subunits provided herein can be co-expressed with $\alpha_2$, $\alpha_3$, $\alpha_4$, $\alpha_5$, $\alpha_7$, $\beta_2$ and/or $\beta_4$ receptor subunits. As noted previously, some of the neuronal nAChR subunits may be capable of forming functional receptors in the absence of other subunits, thus co-expression is not always required to produce functional receptors. Moreover, some nAChR subunits may require co-expression with two or more nAChR subunits to participate in functional receptors.

F. Assays

In accordance with one embodiment provided herein, recombinant human neuronal nAChR-expressing mammalian cells or oocytes can be contacted with a test compound, and the modulating effect(s) thereof can then be evaluated by comparing the nAChR-mediated response in the presence and absence of test compound, or by comparing the nAChR-mediated response of test cells, or control cells to the presence of the compound.

As understood by those of skill in the art, assay methods for identifying compounds that modulate human neuronal nAChR activity (e.g., agonists and antagonists) generally require comparison to a control. As noted above, one type of a "control" cell or "control" culture is a cell or culture that is treated substantially the same as the cell or culture exposed to the test compound, except the control culture is not expose to test compound. For example, in methods that use voltage clamp eletrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express functional human neuronal nAChRs. In this situation, the response of test cell to test compound is compared to the response (or lack of response) of receptor-negative (control) cell to test compound, when cells or cultures of each type of cell are exposed to substantially the same reaction conditions in the presence of compound being assayed.

Functional recombinant human neuronal nAChRs include at least an alpha subunit, or at least an alpha subunit and a beta subunit of a human neuronal nAChR. Eukaryotic cells expressing these subunits have been prepared by injection of RNA transcripts and by transfection of DNA. Such cells have exhibited nAChR activity attributable to human neuronal nAChRs that contain one or more of the heterologous human neuronal nAChR subunits.

With respect to measurement of the activity of functional heterologous human neuronal nAChRs, endogenous nAChR activity and, if desired, activity of nAChRs that contain a mixture of endogenous host cell subunits and heterologous subunits, should, if possible, be inhibited to a significant extent by chemical, pharmacological and electrophysiological means.

G. Antibodies

Also provided herein are antibodies generated against the above-described nAChR subunits or portions thereof. Such antibodies may be employed for assessing receptor tissue localization, subtype composition, structure of functional domains, purification of receptors, as well as in diagnostic and therapeutic applications. Preferably for therapeutic applications, the antibodies employed will be monoclonal antibodies.

The above-described antibodies can be prepared employing standard techniques, as are well known to those of skill in the art, using the nAChR subunit proteins, or portions thereof, described herein as antigens for antibody production. Both anti-peptide and anti-fusion protein antibodies can be used [see, for example, Bahouth et al. (1991) *Trends Pharmacol. Sci.* 12:338–343; *Current Protocols in Molecular Biology* (Ausubel et al., eds.), John Wiley and Sons, New York (1989)]. Factors to consider in selecting portions of the nAChR subunits for use as immunogen (as either a synthetic peptide or a recombinantly produced bacterial fusion protein) include antigenicity, accessibility (i.e., extracellular and cytoplasmic domains), uniqueness to the particular subtype, and other factors known to those of skill in this art.

The availability of subtype-specific antibodies makes possible the application of the technique of immunochemistry to monitor the distribution and expression density of various subtypes (e.g., in normal vs. diseased brain tissue). The antibodies produced using the human nAChR subunits as immunogens have, among other properties, the ability to specifically and preferentially bind to and/or cause the immunoprecipitation of human nAChR or a subunit thereof which may be present in a biological sample or a solution derived from such a sample. Such antibodies may also be used to selectively isolate cells that express human nAChR that contain the subunit for which the antibodies are specific. Such antibodies could also be employed for diagnostic and therapeutic applications. In a further embodiment, there are provided methods for modulating the ion channel activity of nAChRs by contacting the receptors with an effective amount of the above-described antibodies.

The antibodies herein can be administered to a subject employing standard methods, such as, for example, by intraperitoneal, intramuscular, intravenous, or subcutaneous injection, implant or transdermal modes of administration. One of skill in the art can readily determine dose forms, treatment regiments, etc., depending on the mode of administration employed.

The following examples are included for illustrative purposes only and are not intended to limit the scope of the invention.

EXAMPLE 1

Isolation of DNA Encoding Human nAChR $\alpha_6$ Subunits

A human substantia nigra cDNA library (Clontech Laboratories, Inc.) was screened for hybridization to a fragment of the rat nAChR $\alpha_6$ subunit cDNA. Isolated plaques were transferred to nitrocellulose filters and hybridization was performed in 5× Denhardt's, 5×SSPE, 50% formamide, 200 µg/ml denatured salmon sperm DNA and 0.2% SDS, at 42° C. Washes were performed in 0.2×SSPE, 0.2% SDS, at 60° C.

Five hybridizing clones were plaque-purified and characterized by restriction endonuclease mapping and DNA sequence analysis.

The DNA sequence of the 5'- and 3'-ends of the cDNA inserts was determined using commercially available λgt10 forward and reverse oligonucleotide primers. Analysis of the DNA sequence of the five cDNA inserts revealed that three clones contained the translational initiation codon, a full-length $\alpha_6$ open reading frame (nucleotides 143–1624 of SEQ ID NO:9), the translational stop codon and 142 additional nucleotides of 5'- and 116 nucleotides of 3'-flanking sequences. The amino acid sequence deduced from the nucleotide sequence of the full-length clone has ~82% identity with the amino acid sequence deduced from the rat nAChR $\alpha_6$ subunit DNA. Several regions of the deduced rat and human $\alpha_6$ amino acid sequences are notably dissimilar:

Amino acids 1–30 (the human signal sequence has only ~56% identity with respect to the rat sequence), Amino acids 31–50 (the human sequence has only ~70% identity with respect to the rat sequence), Amino acids 344–391 (the human sequence has only ~40% identity with respect to the rat sequence), Amino acids 401–428 (the human sequence has only 64% identity with respect to the rat sequence).

Furthermore, the insert DNA of a single clone, KEα6.5, was determined to be missing 45 nucleotides of $\alpha_6$ coding sequence, resulting in an in-frame deletion of 15 amino acid residues of the deduced amino acid sequence (residues 74 to 88 of SEQ ID NO:10). The nucleotide sequence of an $\alpha_6$ subunit variant lacking this sequence is shown in SEQ ID NO:19 and the amino acid sequence deduced therefrom is shown in SEQ ID NO:20. Interestingly, the deduced amino acid sequence immediately downstream of the site of the deletion shares only ~58% amino acid identity with the deduced rat αc6 amino acid sequence (amino acids 89–100 of SEQ ID NO:10).

EXAMPLE 2

Isolation of DNA Encoding A Human nAChR $\beta_3$ Subunit

A human substantia nigra cDNA library (Clontech Laboratories, Inc.) was screened for hybridization to synthetic oligonucleotides complementary to the human nicotinic nAChR $\beta_3$ subunit cDNA. Isolated plaques were transferred to nitrocellulose filters and hybridized under high stringency conditions with respect to oligonucleotides (washing conditions 1×SSPE, 0.2% SDS at 50° C.) with synthetic oligonucleotides complementary to sequences of the human $\beta_3$ nAChR subunit cDNA that include nucleotides 212–230 and 1442–1469 of SEQ ID NO:15.

Two hybridizing clones were plaque-purified and characterized by restriction endonuclease mapping. The DNA sequence of the 5'- and 3'-ends of the cDNA insert was determined using commercially available T7 and SP6 oligonucleotide primers. The complete sequence of clone KB$\beta_{3.2}$ was determined. Clone KBβ3.2 contains a 1927 bp cDNA insert that contains a 1,377-nucleotide open reading frame encoding a full-length $\beta_3$ nAChR subunit (nucleotides 98–1471 SEQ ID NO:15) as well as 97 nucleotides of 5'- and 454 nucleotides of 3'-untranslated sequence. The amino acid sequence deduced from the nucleotide sequence of the full-length clone has ~81% identity with the amino acid sequence deduced from the rat nicotinic nAChR $\beta_3$ subunit DNA. Several regions of the deduced rat and human $\beta_3$ amino acid sequences are notably dissimilar:

Amino acids 1–28 (the human signal sequence has only ~25% identity with respect to the rat sequence), Amino acids 347–393 (the human sequence has only ~55% identity with respect to the rat sequence), Amino acids 440–464 (the human sequence has only ~68% identity with respect to the rat sequence).

EXAMPLE 3

Preparation of Constructs for the Expression of Recombinant Human Neuronal nAChR Subunits Isolated cDNAs encoding human neuronal nAChR subunits were incorporated into vectors for use in expressing the subunits in mammalian host cells and for use in generating in vitro transcripts from the DNAs to be expressed in *Xenopus oöcytes*. The following vectors were utilized in preparing the constructs.

A. Constructs for Expressing Human nAChR $\alpha_6$ Subunits

A 1,743 bp EcoRI fragment, encoding a full-length nAChR $\alpha_6$ subunit, was isolated from KEα6.3 by standard methods and ligated into the EcoRI polylinker site of the vector pcDNA3 to generate pcDNA3-KEα6.3 (see FIG. 1). Plasmid pcDNA3 (see FIG. 1) is a pUC19-based vector that contains a CMV promoter/enhancer, a T7 bacteriophage RNA polymerase promoter positioned downstream of the CMV promoter/enhancer, a bovine growth hormone (BGH) polyadenylation signal downstream of the T7 promoter, and a polylinker between the T7 promoter and the BGH polyadenylation signal. This vector thus contains all of the regulatory elements required for expression in a mammalian host cell of heterologous DNA which has been incorporated into the vector at the polylinker. In addition, because the T7 promoter is located just upstream of the polylinker, this plasmid can be used for the synthesis of in vitro transcripts of heterologous DNA that has been subcloned into the vector at the polylinker. Furthermore, this plasmid contains a gene encoding neomycin resistance used as a selectable marker during transfection. FIG. 1 also shows a partial restriction map of pcDNA3-KEα6.3.

The expression of the full-length human nAChR $\alpha_6$ subunit was optimized by the introduction of a consensus ribosome binding site [RBS; see, e.g., Kozak (1991) *J. Biol. Chem.* 266:19867–19870] prior to the translational start codon. The existing 5'-untranslated region was modified by PCR mutagenesis using the plasmid pcDNA3-KEα6.3 as a DNA template and a complementary upstream oligonucleotide containing the appropriate nucleotide RBS substitutions as well as flanking 5' HindIII and EcoRI sites, and an oligonucleotide complementary to $\alpha_6$ coding sequences ~450 nucleotides downstream of the translational start codon. The resulting amplification product contained HindIII and EcoRI sites followed by the consensus RBS and nucleotides 1–459 of the human nAChR $\alpha_6$ coding sequence (nucleotides 143–602 of SEQ ID NO:9). The amplified DNA was digested with HindIII and BamHI; the 308-bp HindIII-BamHI fragment was isolated and ligated with the 5.3 kb BamHI-PvuI fragment of pcDNA3-KEα6.3 and the 1.4-kb PvuI to HindIII fragment from pcDNA3 to generate the ~7.0 kb plasmid pcDNA3-KEα6RBS.

B. Constructs for Expressing Human Neuronal nAChR $\beta_3$ Subunits

Figure 2:
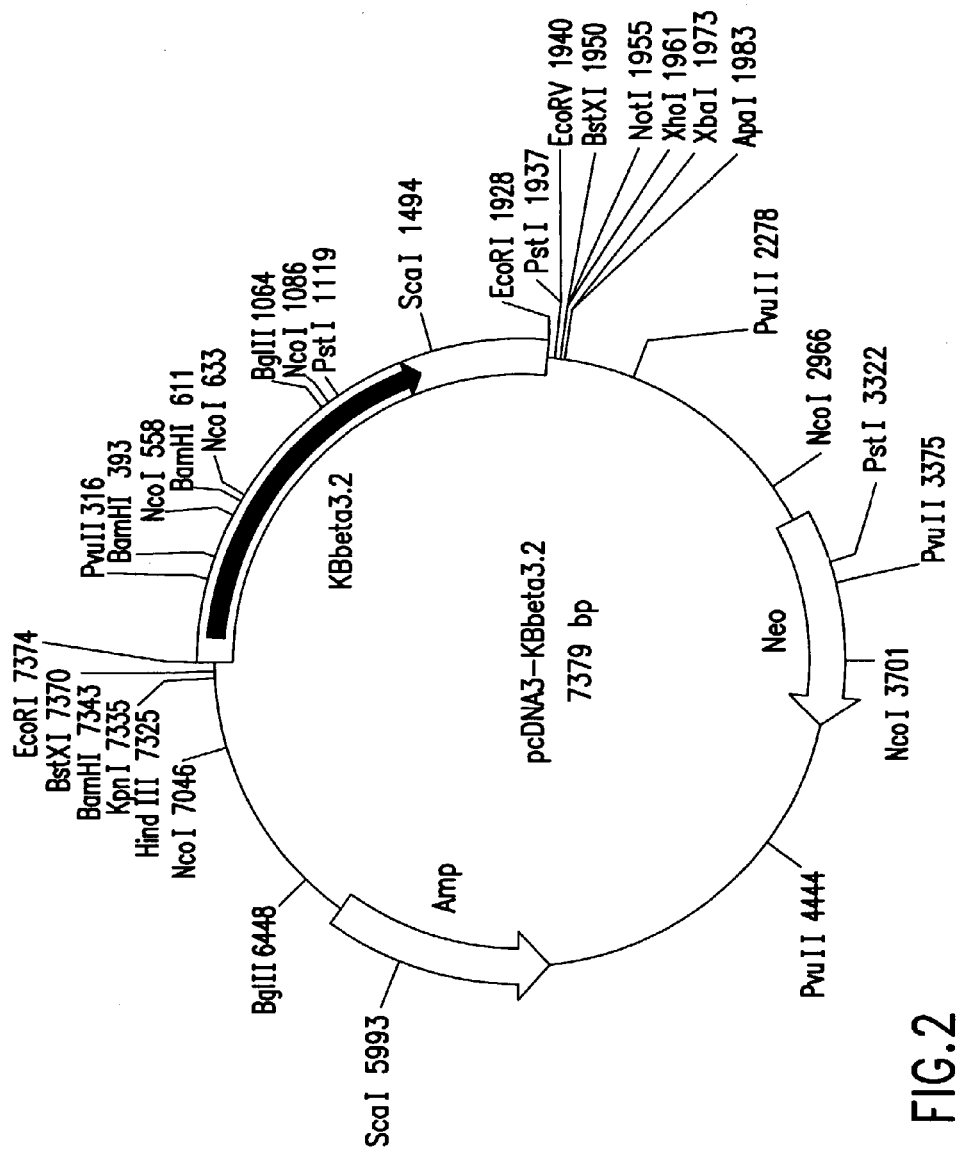
FIG. 2 presents a restriction map of a CMV promoter-based vector pcDNA3-KBbeta3.2 that contains a $\beta_3$-encoding fragment as an EcoRI insert.

An ~2.0 kb EcoRI fragment, encoding a full-length nicotinic AChR $\beta_3$ subunit, was isolated from KBβ3.2 by standard methods and ligated into the EcoRI polylinker site of the vector pcDNA3 to generate pcDNA3-KBβ3.2 (see FIG. 2). FIG. 2 also shows a partial restriction map of pcDNA3.KBβ3.2.

The expression of the full-length human nicotinic nAChR $\beta_3$ subunit is optimized by the introduction of a consensus ribosome binding site (RBS) prior to the translational start codon. The existing 5'-untranslated region is modified by PCR mutagenesis using a method similar to that described above for the $\alpha_6$ nAChR subunit to generate pcDNA3-KBβ3RBS.

EXAMPLE 4

Expression of Recombinant Human Neuronal nAChR in Xenopus

Xenopus oöcytes are injected with in vitro transcripts prepared from constructs containing DNA encoding $\alpha_6$ and $\beta_3$ subunits. Electrophysiological measurements of the oocyte transmembrane currents are made using the two-electrode voltage clamp technique (see, e.g., Stuhmer (1992) *Meth. Enzymol.* 207:310–339).

1. Preparation of in vitro Transcripts

Recombinant capped transcripts of pcDNA3-KEαRBS and pcDNA3-KBβ3RBS are synthesized from linearized plasmids using the mMessage and mMachine in vitro transcription kit according to the capped transcript protocol provided by the manufacturer (Catalog 1344 from AMBION, Inc., Austin, Tex.). The mass of the synthesized transcripts is determined by UV absorbance and the integrity of the transcripts is determined by electrophoresis through an agarose gel.

2. Electrophysiology

Xenopus oöcytes are injected with either 12.5, 50 or 125 ng of one or more human nicotinic nAChR α and β subunit transcript per oocyte. The preparation and injection of oocytes is carried out as described by Dascal (1987) in *Crit. Rev. Biochem.* 22:317–387. Two-to-six days following mRNA injection, the oocytes are examined using the two-electrode voltage clamp technique. The cells are bathed in Ringer's solution (115 mM NaCl, 2.5 mM KCl, 1.8 mM $CaCl_2$, 10 mM HEPES, pH 7.3) containing 1 µM atropine with or without 100 µM d-tubocurarine. Cells are voltage-clamped at −60 to −80 mV. Data are acquired with Axotape software at 2–5 Hz. The agonists acetylcholine (ACh), nicotine, and cytisine are added at concentrations ranging from 0.1 µM to 100 µM.

EXAMPLE 5

Recombinant Expression of Human nAChR Subunits in Mammalian Cells

Human embryonic kidney (HEK) 293 cells are transiently and stably transfected with DNA encoding human neuronal nicotinic nAChR $\alpha_6$ and $\beta_3$ subunits. Transient transfectants are analyzed for expression of nicotinic nAChR using various assays, e.g., electrophysiological methods, $Ca^{2+}$-sensitive fluorescent indicator-based assays.

1. Transient Transfection of HEK Cells

HEK cells are transiently co-transfected with DNA encoding one or more α subunit and/or one or more β subunits. Approximately $2 \times 10^6$ HEK cells are transiently transfected with 18 µg of the indicated plasmid(s) according to standard CaPO4 transfection procedures (Wigler et al. (1979) *Proc. Natl. Acad. Sci. U.S.A.* 76:1373–1376) or using lipofectamine according to the manufacturer's instructions (Bethesda Research Laboratory (BRL), Gaithersburg, Md.). In addition, 2 µg of plasmid pCMVβgal (Clontech Laboratories, Palo Alto, Calif.), which contains the *Escherichia coli* β-galactosidase gene fused to the CMV promoter, are co-transfected as a reporter gene for monitoring the efficiency of transfection. The transfectants are analyzed for β-galactosidase expression by measurement of β-galactosidase activity [Miller (1972) *Experiments in Molecular Genetics*, pp. 352–355, Cold Spring Harbor Press]. Transfectants can also be analyzed for β-galactosidase expression by direct staining of the product of a reaction involving β-galactosidase and the X-gal substrate [Jones (1986) *EMBO* 5:3133–3142].

2. Stable Transfection of HIEK Cells

HEK cells are transfected using the calcium phosphate transfection procedure [*Current Protocols in Molecular Biology*, Vol. 1, Wiley Inter-Science, Supplement 14, Unit 9.1.1–9.1.9 (1990)]. HEK cells are transfected with 1 ml of DNA/calcium phosphate precipitate containing the DNA encoding the desired alpha and beta subunits and pSV2neo (as a selectable marker). After 14 days of growth in medium containing 1 µg/ml G418, colonies form and are individually isolated by using cloning cylinders. The isolates are subjected to limiting dilution and screened to identify those that expressed the highest level of nAChR, as described below.

EXAMPLE 6

Characterization of Cell Lines Expressing Human Neuronal nAChRs

Recombinant cell lines generated by transfection with DNA encoding human neuronal nAChR subunits, such as those described in EXAMPLE 5, can be further characterized using one or more of the following methods.

A. Northern or slot blot analysis for expression of α- and/or β-subunit encoding messages Total RNA is isolated from ~1X10$^7$ cells and 10–15 μg of RNA from each cell type is used for Northern or slot blot hybridization analysis. The inserts from human neuronal nAChR-encoding plasmids can be nick-translated and used as probe. In addition, a fragment of the glyceraldehyde-3-phosphate dehyrodgenase (GAPD) gene sequence (Tso et a (1985) *Nucleic Acids Res.* 13:2485) can be nick-translated and used as a control probe on duplicate filters to confirm the presence or absence of RNA on each blot and to provide a rough standard for use in quantitating differences in α- or β-specific mRNA levels between cell lines. Typical Northern and slot blot hybridization and wash conditions are as follows:

hybridization in 5×SSPE, 5× Denhardt's solution, 0.2% SDS, 200 μg/ml denatured, sonicated herring sperm DNA, 50% formamide, at 42° C. followed by washing in 0.1× SSPE, 0.1%SDS, at 65° C.

B. Binding Assay

Cell lines generated by transfection with human neuronal nAChR α- or α- and β-subunit-encoding DNA can be analyzed for their ability to bind nicotine or other agonist, for example, as compared to control cell lines: e.g., neuronally-derived cell lines PC12 (Boulter et al. (1986) *Nature* 319:368–374; ATCC #CRL1721) and IMR32 (Clementi, et al. (1986) *Int. J. Neurochem.* 47:291–297; ATCC #CCL127), and muscle-derived cell line BC3H1 (Patrick, et al. (1977) *J. Biol. Chem.* 252:2143–2153). Negative control cells (i.e., host cells from which the transfectants were prepared) are also included in the assay. The assay is conducted as follows:

Just prior to being assayed, transfected cells are removed from plates by scraping. Positive control cells used are PC12, BC3H1, and IMR32 (which had been starved for fresh media for seven days). Control cell lines are removed by rinsing in 37° C. assay buffer (50 mM Tris/HCl, 1 mM MgCl$_2$, 2 mM CaCl$_2$, 120 mM NaCl, 3 mM EDTA, 2 mg/ml BSA and 0.1% aprotinin at pH 7.4). The cells are washed and resuspended to a concentration of 1×10$^6$/250 μl. To each plastic assay tube is added 250 μl of the cell solution, 15 nM $^3$H-nicotine, with or without 1 mM unlabeled nicotine, and assay buffer to make a final volume of 500 μl. The assays for the transfected cell lines are incubated for 30 min at room temperature; the assays of the positive control cells are incubated for 2 min at 1° C. After the appropriate incubation time, 450 μl aliquots of assay volume are filtered through Whatman GF/C glass fiber filters which have been pretreated by incubation in 0.05% polyethylenenimine for 24 hours at 4 C. The filters are then washed twice, with 4 ml each wash, with ice cold assay buffer. After washing, the filters are dried, added to vials containing 5 ml scintillation fluid and radioactivity is measured.

C. $^{86}$Rb Ion-Flux Assay

The ability of nicotine or nAChR agonists and antagonists to mediate the influx of $^{86}$Rb into transfected and control cells has been found to provide an indication of the presence of functional nAChRs on the cell surface. The $^{86}$Rb ion-flux assay is conducted as follows:

1. The night before the experiment, cells are plated at 2×10$^6$ per well (i.e., 2 ml per well) in a 6-well polylysine-coated plate.
2. The culture medium is decanted and the plate washed with 2 ml of assay buffer (50 mM HEPES, 260 mM sucrose, 5.4 mM KCl, 1.8 mM CaCl$_2$, 0.8 mM MgSO$_4$, 5.5 mM glucose) at room temperature.
3. The assay buffer is decanted and 1 ml of assay buffer, containing 3 μCi/ml $^{86}$Rb, with 5 mM ouabain and agonist or antagonist in a concentration to effect a maximum response, is added.
4. The plate is incubated on ice at 1° C. for 4 min.
5. The buffer is decanted into a waste container and each well was washed with 3 ml of assay buffer, followed by two washes of 2 ml each.
6. The cells are lysed with 2×0.5 ml of 0.2% SDS per well and transferred to a scintillation vial containing 5 ml of scintillation fluid.
7. The radioactivity contained in each vial 5 is measured and the data calculated. Positive control cells provided the following data in this assay:

|  | PC12 | | IMR32 | |
| --- | --- | --- | --- | --- |
|  | EC$_{50}$ | Maximum Response | EC$_{50}$ | Maximum Response |
| Agonist |  |  |  |  |
| nicotine | 52 μM | 2.1X[a] | 18 μM | 7.7X[a] |
| CCh* | 35 μM | 3.3X[b] | 230 μM | 7.6X[c] |
| Cytisine | 57 μM | 3.6X[d] | 14 μM | 10X[e] |
| Antagonist |  |  |  |  |
| d-tubocurarine | 0.81 μM |  | 2.5 μM |  |
| mecamylamine | 0.42 μM |  | 0.11 μM |  |
| hexamethonium | nd[f] |  | 22 μM |  |
| atropine | 12.5 μM |  | 43 μM |  |

*CCh = carbamylcholine
[a]200 μM nicotine
[b]300 μM CCh
[c]3 mM CCh
[d]1 mM cytisine
[e]100 μM cytisine
[f]nd = not determined D. Electrophysiological Analysis of Mammalian Cells Transfected with Human Neuronal nAChR Subunit-Encoding DNA Electrophysiological measurements may be used to assess the activity of recombinant receptors or to assess the ability of a test compound to potentiate, antagonize or otherwise modulate the magnitude and duration of the flow of cations through the ligand-gated recombinant nAChR. The function of the expressed neuronal nAChR can be assessed by a variety of electrophysiological techniques, including two-electrode voltage clamp and patch clamp methods. The cation-conducting channel intrinsic to the nAChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques. In preferred embodiments, transfected mammalian cells or injected oocytes are analyzed electrophysiologically for the presence of nAChR agonist-dependent currents.

E. Fluroescent Indicator-Based Assays

Activation of the ligand-gated nAChR by agonists leads to an influx of cations, including $Ca^{++}$, through the receptor channel. $Ca^{++}$ entry into the cell through the channel can induce release of calcium contained in intracellular stores. Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic nAChR expression. One method for measuring intracellular calcium levels relies on calcium-sensitive fluorescent indicators.

Calcium-sensitive indicators, such as fluo-3 (Catalog No. F01241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying nicotinic nAChR has been described (see, U.S. patent application Ser. Nos. 08/229,150, 08/244,985, 08/434,511, and 08/434,968 and corresponding published International PCT Patent Application No. US92/11090; see, also, published International PCT application No. 96/05488).

HEK cells that are transiently or stably co-transfected with DNA encoding appropriate α and/or β subunits and $α_6$ and $β_3$ subunits are analyzed for expression of functional recombinant nAChR using the automated fluorescent indicator-based assay. The assay procedure is as follows. Untransfected HEK cells and HEK cells co-transfected with DNA encoding the appropriate α and β subunits are plated in the wells of a 96-well microtiter dish and loaded with fluo-3 by incubation for 2 hours at 20° C. in a medium containing 20 µM fluo-3, 0.2% Pluronic F-127 in HBS (125 mM NaCl, 5 mM KCl, 1.8 mM $CaCl_2$, 0.62 mM $MgSO_4$, 6 mM glucose, 20 mM HEPES, pH 7.4). The cells are then washed with assay buffer (i.e., HBS). The antagonist d-tubocurarine is added to some of the wells at a final concentration of 10 µM. The microtiter dish is then placed into a fluorescence plate reader and the basal fluorescence of each well is measured and recorded before addition of agonist, e.g., 200 µM nicotine, to the wells. The fluorescence of the wells is monitored repeatedly during a period of approximately 60 seconds following addition of nicotine.

The fluorescence of the untransfected HEK cells does not change after addition of nicotine. In contrast, the fluorescence of the co-transfected cells, in absence of d-tubocurarine, increases dramatically after addition of nicotine to the wells. This nicotine-stimulated increase in fluorescence is not observed in co-transfected cells that had been exposed to the antagonist d-tubocurarine. Such results demonstrate that the co-transfected cells express functional recombinant nAChR that are activated by nicotine and blocked by d-tubocurarine.

While the invention has been described in detail with reference to certain preferred embodiments thereof, it will be understood that modifications and variations are within the spirit and scope of that which is described and claimed.

Since modifications will be apparent to those of skill in this art, it is intended that this invention be limited only by the scope of the appended claims.

---

What is claimed:

1. A substantially pure human neuronal nicotinic acetylcholine α₆ subunit encoded by a nucleic acid molecule comprising nucicotides 143–1624 of SEQ ID NO:9.

2. A substantially pure human neuronal nicotinic acetylcholine receptor, comprising an α₆ human neuronal nicotinic acetylcholine receptor subunit, wherein the subunit comprises the amino acid sequence as set in any one of SEQ ID NO:10.

3. The nicotinic receptor of claim 2, further comprising a human neuronal nicotinic acetylcholine receptor β subunit.

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 2664 base pairs
      (B) TYPE: nucleic acid
      (C) STRANDEDNESS: double
      (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
      (A) NAME/KEY: 5'UTR
      (B) LOCATION: 555...2141
      (D) OTHER INFORMATION: alpha2 subunit of human neuronal
          nicotinic acetylcholine receptor (xi) SEQUENCE DESCRIPTION: SEQ ID NO: 1:

```
GAGAGAACAG CGTGAGCCTG TGTGCTTGTG TGCTGAGCCC TCATCCCCTC CTGGGGCCAG    60
```

-continued

```
GCTTGGGTTT CACCTGCAGA ATCGCTTGTG CTGGGCTGCC TGGGCTGTCC TCAGTGGCAC    120

CTGCATGAAG CCGTTCTGGC TGCCAGAGCT GGACAGCCCC AGGAAAACCC ACCTCTCTGC    180

AGAGCTTGCC CAGCTGTCCC CGGGAAGCCA AATGCCTCTC ATGTAAGTCT TCTGCTCGAC    240

GGGGTGTCTC CTAAACCCTC ACTCTTCAGC CTCTGTTTGA CCATGAAATG AAGTGACTGA    300

GCTCTATTCT GTACCTGCCA CTCTATTTCT GGGGTGACTT TTGTCAGCTG CCCAGAATCT    360

CCAAGCCAGG CTGGTTCTCT GCATCCTTTC AATGACCTGT TTTCTTCTGT AACCACAGGT    420

TCGGTGGTGA GAGGAAGCCT CGCAGAATCC AGCAGAATCC TCACAGAATC CAGCAGCAGC    480

TCTGCTGGGG ACATGGTCCA TGGTGCAACC CACAGCAAAG CCCTGACCTG ACCTCCTGAT    540
```

```
GCTCAGGAGA AGCC ATG GGC CCC TCC TGT CCT GTG TTC CTG TCC TTC ACA      590
              Met Gly Pro Ser Cys Pro Val Phe Leu Ser Phe Thr
              1                5                       10

AAG CTC AGC CTG TGG TGG CTC CTT CTG ACC CCA GCA GGT GGA GAG GAA      638
Lys Leu Ser Leu Trp Trp Leu Leu Leu Thr Pro Ala Gly Gly Glu Glu
         15                  20                  25

GCT AAG CGC CCA CCT CCC AGG GCT CCT GGA GAC CCA CTC TCC TCT CCC      686
Ala Lys Arg Pro Pro Pro Arg Ala Pro Gly Asp Pro Leu Ser Ser Pro
    30                  35                  40

AGT CCC ACG GCA TTG CCG CAG GGA GGC TCG CAT ACC GAG ACT GAG GAC      734
Ser Pro Thr Ala Leu Pro Gln Gly Gly Ser His Thr Glu Thr Glu Asp
45                  50                  55                  60

CGG CTC TTC AAA CAC CTC TTC CGG GGC TAC AAC CGC TGG GCG CGC CCG      782
Arg Leu Phe Lys His Leu Phe Arg Gly Tyr Asn Arg Trp Ala Arg Pro
                65                  70                  75

GTG CCC AAC ACT TCA GAC GTG GTG ATT GTG CGC TTT GGA CTG TCC ATC      830
Val Pro Asn Thr Ser Asp Val Val Ile Val Arg Phe Gly Leu Ser Ile
            80                  85                  90

GCT CAG CTC ATC GAT GTG GAT GAG AAG AAC CAA ATG ATG ACC ACC AAC      878
Ala Gln Leu Ile Asp Val Asp Glu Lys Asn Gln Met Met Thr Thr Asn
        95                  100                 105

GTC TGG CTA AAA CAG GAG TGG AGC GAC TAC AAA CTG CGC TGG AAC CCC      926
Val Trp Leu Lys Gln Glu Trp Ser Asp Tyr Lys Leu Arg Trp Asn Pro
    110                 115                 120

GCT GAT TTT GGC AAC ATC ACA TCT CTC AGG GTC CCT TCT GAG ATG ATC      974
Ala Asp Phe Gly Asn Ile Thr Ser Leu Arg Val Pro Ser Glu Met Ile
125                 130                 135                 140

TGG ATC CCC GAC ATT GTT CTC TAC AAC AAT GCA GAT GGG GAG TTT GCA      1022
Trp Ile Pro Asp Ile Val Leu Tyr Asn Asn Ala Asp Gly Glu Phe Ala
                145                 150                 155

GTG ACC CAC ATG ACC AAG GCC CAC CTC TTC TCC ACG GGC ACT GTG CAC      1070
Val Thr His Met Thr Lys Ala His Leu Phe Ser Thr Gly Thr Val His
            160                 165                 170

TGG GTG CCC CCG GCC ATC TAC AAG AGC TCC TGC AGC ATC GAC GTC ACC      1118
Trp Val Pro Pro Ala Ile Tyr Lys Ser Ser Cys Ser Ile Asp Val Thr
        175                 180                 185

TTC TTC CCC TTC GAC CAG CAG AAC TGC AAG ATG AAG TTT GGC TCC TGG      1166
Phe Phe Pro Phe Asp Gln Gln Asn Cys Lys Met Lys Phe Gly Ser Trp
    190                 195                 200

ACT TAT GAC AAG GCC AAG ATC GAC CTG GAG CAG ATG GAG CAG ACT GTG      1214
Thr Tyr Asp Lys Ala Lys Ile Asp Leu Glu Gln Met Glu Gln Thr Val
205                 210                 215                 220

GAC CTG AAG GAC TAC TGG GAG AGC GGC GAG TGG GCC ATC GTC AAT GCC      1262
Asp Leu Lys Asp Tyr Trp Glu Ser Gly Glu Trp Ala Ile Val Asn Ala
                225                 230                 235

ACG GGC ACC TAC AAC AGC AAG AAG TAC GAC TGC TGC GCC GAG ATC TAC      1310
Thr Gly Thr Tyr Asn Ser Lys Lys Tyr Asp Cys Cys Ala Glu Ile Tyr
```

```
                240               245               250
CCC GAC GTC ACC TAC GCC TTC GTC ATC CGG CGG CTG CCG CTC TTC TAC        1358
Pro Asp Val Thr Tyr Ala Phe Val Ile Arg Arg Leu Pro Leu Phe Tyr
            255               260               265

ACC ATC AAC CTC ATC ATC CCC TGC CTG CTC ATC TCC TGC CTC ACT GTG        1406
Thr Ile Asn Leu Ile Ile Pro Cys Leu Leu Ile Ser Cys Leu Thr Val
        270               275               280

CTG GTC TTC TAC CTG CCC TCC GAC TGC GGC GAG AAG ATC ACG CTG TGC        1454
Leu Val Phe Tyr Leu Pro Ser Asp Cys Gly Glu Lys Ile Thr Leu Cys
285               290               295               300

ATT TCG GTG CTG CTG TCA CTC ACC GTC TTC CTG CTG CTC ATC ACT GAG        1502
Ile Ser Val Leu Leu Ser Leu Thr Val Phe Leu Leu Leu Ile Thr Glu
                305               310               315

ATC ATC CCG TCC ACC TCG CTG GTC ATC CCG CTC ATC GGC GAG TAC CTG        1550
Ile Ile Pro Ser Thr Ser Leu Val Ile Pro Leu Ile Gly Glu Tyr Leu
            320               325               330

CTG TTC ACC ATG ATC TTC GTC ACC CTG TCC ATC GTC ATC ACC GTC TTC        1598
Leu Phe Thr Met Ile Phe Val Thr Leu Ser Ile Val Ile Thr Val Phe
        335               340               345

GTG CTC AAT GTG CAC CAC CGC TCC CCC AGC ACC CAC ACC ATG CCC CAC        1646
Val Leu Asn Val His His Arg Ser Pro Ser Thr His Thr Met Pro His
    350               355               360

TGG GTG CGG GGG GCC CTT CTG GGC TGT GTG CCC CGG TGG CTT CTG ATG        1694
Trp Val Arg Gly Ala Leu Leu Gly Cys Val Pro Arg Trp Leu Leu Met
365               370               375               380

AAC CGG CCC CCA CCA CCC GTG GAG CTC TGC CAC CCC CTA CGC CTG AAG        1742
Asn Arg Pro Pro Pro Pro Val Glu Leu Cys His Pro Leu Arg Leu Lys
                385               390               395

CTC AGC CCC TCT TAT CAC TGG CTG GAG AGC AAC GTG GAT GCC GAG GAG        1790
Leu Ser Pro Ser Tyr His Trp Leu Glu Ser Asn Val Asp Ala Glu Glu
            400               405               410

AGG GAG GTG GTG GTG GAG GAG GAG GAC AGA TGG GCA TGT GCA GGT CAT        1838
Arg Glu Val Val Val Glu Glu Glu Asp Arg Trp Ala Cys Ala Gly His
        415               420               425

GTG GCC CCC TCT GTG GGC ACC CTC TGC AGC CAC GGC CAC CTG CAC TCT        1886
Val Ala Pro Ser Val Gly Thr Leu Cys Ser His Gly His Leu His Ser
    430               435               440

GGG GCC TCA GGT CCC AAG GCT GAG GCT CTG CTG CAG GAG GGT GAG CTG        1934
Gly Ala Ser Gly Pro Lys Ala Glu Ala Leu Leu Gln Glu Gly Glu Leu
445               450               455               460

CTG CTA TCA CCC CAC ATG CAG AAG GCA CTG GAA GGT GTG CAC TAC ATT        1982
Leu Leu Ser Pro His Met Gln Lys Ala Leu Glu Gly Val His Tyr Ile
                465               470               475

GCC GAC CAC CTG CGG TCT GAG GAT GCT GAC TCT TCG GTG AAG GAG GAC        2030
Ala Asp His Leu Arg Ser Glu Asp Ala Asp Ser Ser Val Lys Glu Asp
            480               485               490

TGG AAG TAT GTT GCC ATG GTC ATC GAC AGG ATC TTC CTC TGG CTG TTT        2078
Trp Lys Tyr Val Ala Met Val Ile Asp Arg Ile Phe Leu Trp Leu Phe
        495               500               505

ATC ATC GTC TGC TTC CTG GGG ACC ATC GGC CTC TTT CTG CCT CCG TTC        2126
Ile Ile Val Cys Phe Leu Gly Thr Ile Gly Leu Phe Leu Pro Pro Phe
    510               515               520

CTA GCT GGA ATG ATC TGACTGCACC TCCCTCGAGC TGGCTCCCAG GGCAAAGGGG AG     2183
Leu Ala Gly Met Ile
525

GGTTCTTGGA TGTGGAAGGG CTTTGAACAA TGTTTAGATT TGGAGATGAG CCCAAAGTGC      2243

CAGGGAGAAC AGCCAGGTGA GGTGGGAGGT TGGAGAGCCA GGTGAGGTCT CTCTAAGTCA      2303

GGCTGGGGTT GAAGTTTGGA GTCTGTCCGA GTTTGCAGGG TGCTGAGCTG TATGGTCCAG      2363
```

-continued

```
CAGGGGAGTA ATAAGGGCTC TTCCGGAAGG GGAGGAAGCG GGAGGCAGGC CTGCACCTGA    2423

TGTGGAGGTA CAGGCAGATC TTCCCTACCG GGGAGGGATG GATGGTTGGA TACAGGTGGC    2483

TGGGCTATTC CATCCATCTG GAAGCACATT TGAGCCTCCA GGCTTCTCCT TGACGTCATT    2543

CCTCTCCTTC CTTGCTGCAA AATGGCTCTG CACCAGCCGG CCCCCAGGAG GTCTGGCAGA    2603

GCTGAGAGCC ATGGCCTGCA GGGGCTCCAT ATGTCCCTAC GCGTGCAGCA GGCAAACAAG    2663

A                                                                    2664
```

(2) INFORMATION FOR SEQ ID NO: 2:

(i) SEQUENCE CHARACTERISTICS:
      (A) LENGTH: 529 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 2:

```
Met Gly Pro Ser Cys Pro Val Phe Leu Ser Phe Thr Lys Leu Ser Leu
1               5                   10                  15

Trp Trp Leu Leu Leu Thr Pro Ala Gly Gly Glu Glu Ala Lys Arg Pro
            20                  25                  30

Pro Pro Arg Ala Pro Gly Asp Pro Leu Ser Ser Pro Ser Pro Thr Ala
        35                  40                  45

Leu Pro Gln Gly Gly Ser His Thr Glu Thr Glu Asp Arg Leu Phe Lys
    50                  55                  60

His Leu Phe Arg Gly Tyr Asn Arg Trp Ala Arg Pro Val Pro Asn Thr
65                  70                  75                  80

Ser Asp Val Val Ile Val Arg Phe Gly Leu Ser Ile Ala Gln Leu Ile
                85                  90                  95

Asp Val Asp Glu Lys Asn Gln Met Met Thr Thr Asn Val Trp Leu Lys
            100                 105                 110

Gln Glu Trp Ser Asp Tyr Lys Leu Arg Trp Asn Pro Ala Asp Phe Gly
        115                 120                 125

Asn Ile Thr Ser Leu Arg Val Pro Ser Glu Met Ile Trp Ile Pro Asp
    130                 135                 140

Ile Val Leu Tyr Asn Asn Ala Asp Gly Glu Phe Ala Val Thr His Met
145                 150                 155                 160

Thr Lys Ala His Leu Phe Ser Thr Gly Thr Val His Trp Val Pro Pro
                165                 170                 175

Ala Ile Tyr Lys Ser Ser Cys Ser Ile Asp Val Thr Phe Phe Pro Phe
            180                 185                 190

Asp Gln Gln Asn Cys Lys Met Lys Phe Gly Ser Trp Thr Tyr Asp Lys
        195                 200                 205

Ala Lys Ile Asp Leu Glu Gln Met Glu Gln Thr Val Asp Leu Lys Asp
    210                 215                 220

Tyr Trp Glu Ser Gly Glu Trp Ala Ile Val Asn Ala Thr Gly Thr Tyr
225                 230                 235                 240
```

```
Asn Ser Lys Lys Tyr Asp Cys Cys Ala Glu Ile Tyr Pro Asp Val Thr
            245                 250                 255

Tyr Ala Phe Val Ile Arg Arg Leu Pro Leu Phe Tyr Thr Ile Asn Leu
            260                 265                 270

Ile Ile Pro Cys Leu Leu Ile Ser Cys Leu Thr Val Leu Val Phe Tyr
            275                 280                 285

Leu Pro Ser Asp Cys Gly Glu Lys Ile Thr Leu Cys Ile Ser Val Leu
            290                 295                 300

Leu Ser Leu Thr Val Phe Leu Leu Ile Thr Glu Ile Ile Pro Ser
305                 310                 315                 320

Thr Ser Leu Val Ile Pro Leu Ile Gly Glu Tyr Leu Leu Phe Thr Met
            325                 330                 335

Ile Phe Val Thr Leu Ser Ile Val Ile Thr Val Phe Val Leu Asn Val
            340                 345                 350

His His Arg Ser Pro Ser Thr His Thr Met Pro His Trp Val Arg Gly
            355                 360                 365

Ala Leu Leu Gly Cys Val Pro Arg Trp Leu Leu Met Asn Arg Pro Pro
            370                 375                 380

Pro Pro Val Glu Leu Cys His Pro Leu Arg Leu Lys Leu Ser Pro Ser
385                 390                 395                 400

Tyr His Trp Leu Glu Ser Asn Val Asp Ala Glu Glu Arg Glu Val Val
            405                 410                 415

Val Glu Glu Asp Arg Trp Ala Cys Ala Gly His Val Ala Pro Ser
            420                 425                 430

Val Gly Thr Leu Cys Ser His Gly His Leu His Ser Gly Ala Ser Gly
            435                 440                 445

Pro Lys Ala Glu Ala Leu Leu Gln Glu Gly Leu Leu Leu Ser Pro
450                 455                 460

His Met Gln Lys Ala Leu Glu Gly Val His Tyr Ile Ala Asp His Leu
465                 470                 475                 480

Arg Ser Glu Asp Ala Asp Ser Ser Val Lys Glu Asp Trp Lys Tyr Val
            485                 490                 495

Ala Met Val Ile Asp Arg Ile Phe Leu Trp Leu Phe Ile Ile Val Cys
            500                 505                 510

Phe Leu Gly Thr Ile Gly Leu Phe Leu Pro Pro Phe Leu Ala Gly Met
            515                 520                 525

Ile
```

(2) INFORMATION FOR SEQ ID NO: 3:

(i) SEQUENCE CHARACTERISTICS:
        (A) LENGTH: 1908 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 190...1704
        (D) OTHER INFORMATION: alpha3 subunit human neuronal -continued nicotinic acetylcholine receptor (xi) SEQUENCE DESCRIPTION: SEQ ID NO: 3:

```
CCTGTCCTCC CGCGGGTCCG AGGGCGCTGG AAACCCAGCG GCGGCGAAGC GGAGAGGAGC      60

CCCGCGCGTC TCCGCCCGCA CGGCTCCAGG TCTGGGGTCT GCGCTGGAGC CGCGCGGGGA     120

GAGGCCGTCT CTGCGACCGC CGCGCCCGCT CCCGACCGTC CGGGTCCGCG GCCAGCCCGG     180

CCACCAGCC ATG GGC TCT GGC CCG CTC TCG CTG CCC CTG GCG CTG TCG CCG    231
           Met Gly Ser Gly Pro Leu Ser Leu Pro Leu Ala Leu Ser Pro
             1               5                  10

CCG CGG CTG CTG CTG CTG CTG CTG TCT CTG CTG CCA GTG GCC AGG GCC      279
Pro Arg Leu Leu Leu Leu Leu Leu Ser Leu Leu Pro Val Ala Arg Ala
 15                  20                  25                  30

TCA GAG GCT GAG CAC CGT CTA TTT GAG CGG CTG TTT GAA GAT TAC AAT      327
Ser Glu Ala Glu His Arg Leu Phe Glu Arg Leu Phe Glu Asp Tyr Asn
                 35                  40                  45

GAG ATC ATC CGG CCT GTA GCC AAC GTG TCT GAC CCA GTC ATC ATC CAT      375
Glu Ile Ile Arg Pro Val Ala Asn Val Ser Asp Pro Val Ile Ile His
             50                  55                  60

TTC GAG GTG TCC ATG TCT CAG CTG GTG AAG GTG GAT GAA GTA AAC CAG      423
Phe Glu Val Ser Met Ser Gln Leu Val Lys Val Asp Glu Val Asn Gln
         65                  70                  75

ATG ATG GAG ACC AAC CTG TGG CTC AAG CAA ATC TGG AAT GAC TAC AAG      471
Ile Met Glu Thr Asn Leu Trp Leu Lys Gln Ile Trp Asn Asp Tyr Lys
     80                  85                  90

CTG AAG TGG AAC CCC TCT GAC TAT GGT GGG GCA GAG TTC ATG CGT GTC      519
Leu Lys Trp Asn Pro Ser Asp Tyr Gly Gly Ala Glu Phe Met Arg Val
 95                 100                 105                 110

CCT GCA CAG AAG ATC TGG AAG CCA GAC ATT GTG CTG TAT AAC AAT GCT      567
Pro Ala Gln Lys Ile Trp Lys Pro Asp Ile Val Leu Tyr Asn Asn Ala
                115                 120                 125

GTT GGG GAT TTC CAG GTG GAC GAC AAG ACC AAA GCC TTA CTC AAG TAC      615
Val Gly Asp Phe Gln Val Asp Asp Lys Thr Lys Ala Leu Leu Lys Tyr
            130                 135                 140

ACT GGG GAG GTG ACT TGG ATA CCT CCG GCC ATC TTT AAG AGC TCC TGT      663
Thr Gly Glu Val Thr Trp Ile Pro Pro Ala Ile Phe Lys Ser Ser Cys
        145                 150                 155

AAA ATC GAC GTG ACC TAC TTC CCG TTT GAT TAC CAA AAC TGT ACC ATG      711
Lys Ile Asp Val Thr Tyr Phe Pro Phe Asp Tyr Gln Asn Cys Thr Met
    160                 165                 170

AAG TTC GGT TCC TGG TCC TAC GAT AAG GCG AAA ATC GAT CTG GTC CTG      759
Lys Phe Gly Ser Trp Ser Tyr Asp Lys Ala Lys Ile Asp Leu Val Leu
175                 180                 185                 190

ATC GGC TCT TCC ATG AAC CTC AAG GAC TAT TGG GAG AGC GGC GAG TGG      807
Ile Gly Ser Ser Met Asn Leu Lys Asp Tyr Trp Glu Ser Gly Glu Trp
                195                 200                 205

GCC ATC ATC AAA GCC CCA GGC TAC AAA CAC GAC ATC AAG TAC AAC TGC      855
Ala Ile Ile Lys Ala Pro Gly Tyr Lys His Asp Ile Lys Tyr Asn Cys
            210                 215                 220

TGC GAG GAG ATC TAC CCC GAC ATC ACA TAC TCG CTG TAC ATC CGG CGC      903
Cys Glu Glu Ile Tyr Pro Asp Ile Thr Tyr Ser Leu Tyr Ile Arg Arg
        225                 230                 235

CTG CCC TTG TTC TAC ACC ATC AAC CTC ATC ATC CCC TGC CTG CTC ATC      951
Leu Pro Leu Phe Tyr Thr Ile Asn Leu Ile Ile Pro Cys Leu Leu Ile
    240                 245                 250

TCC TTC CTC ACT GTG CTC GTC TTC TAC CTG CCC TCC GAC TGC GGT GAG      999
Ser Phe Leu Thr Val Leu Val Phe Tyr Leu Pro Ser Asp Cys Gly Glu
255                 260                 265                 270

AAG GTG ACC CTG TGC ATT TCT GTC CTC CTC TCC CTG ACG GTG TTT CTC     1047
```

```
Lys Val Thr Leu Cys Ile Ser Val Leu Leu Ser Leu Thr Val Phe Leu
            275                 280                 285

CTG GTG ATC ACT GAG ACC ATC CCT TCC ACC TCG CTG GTC ATC CCC CTG      1095
Leu Val Ile Thr Glu Thr Ile Pro Ser Thr Ser Leu Val Ile Pro Leu
            290                 295                 300

ATT GGA GAG TAC CTC CTG TTC ACC ATG ATT TTT GTA ACC TTG TCC ATC      1143
Ile Gly Glu Tyr Leu Leu Phe Thr Met Ile Phe Val Thr Leu Ser Ile
            305                 310                 315

GTC ATC ACC GTC TTC GTG CTC AAC GTG CAC TAC AGA ACC CCG ACG ACA      1191
Val Ile Thr Val Phe Val Leu Asn Val His Tyr Arg Thr Pro Thr Thr
            320                 325                 330

CAC ACA ATG CCC TCA TGG GTG AAG ACT GTA TTC TTG AAC CTG CTC CCC      1239
His Thr Met Pro Ser Trp Val Lys Thr Val Phe Leu Asn Leu Leu Pro
335                 340                 345                 350

AGG GTC ATG TTC ATG ACC AGG CCA ACA AGC AAC GAG GGC AAC GCT CAG      1287
Arg Val Met Phe Met Thr Arg Pro Thr Ser Asn Glu Gly Asn Ala Gln
            355                 360                 365

AAG CCG AGG CCC CTC TAC GGT GCC GAG CTC TCA AAT CTG AAT TGC TTC      1335
Lys Pro Arg Pro Leu Tyr Gly Ala Glu Leu Ser Asn Leu Asn Cys Phe
            370                 375                 380

AGC CGC GCA GAG TCC AAA GGC TGC AAG GAG GGC TAC CCC TGC CAG GAC      1383
Ser Arg Ala Glu Ser Lys Gly Cys Lys Glu Gly Tyr Pro Cys Gln Asp
            385                 390                 395

GGG ATG TGT GGT TAC TGC CAC CAC CGC AGG ATA AAA ATC TCC AAT TTC      1431
Gly Met Cys Gly Tyr Cys His His Arg Arg Ile Lys Ile Ser Asn Phe
            400                 405                 410

AGT GCT AAC CTC ACG AGA AGC TCT AGT TCT GAA TCT GTT GAT GCT GTG      1479
Ser Ala Asn Leu Thr Arg Ser Ser Ser Ser Glu Ser Val Asp Ala Val
415                 420                 425                 430

CTG TCC CTC TCT GCT TTG TCA CCA GAA ATC AAA GAA GCC ATC CAA AGT      1527
Leu Ser Leu Ser Ala Leu Ser Pro Glu Ile Lys Glu Ala Ile Gln Ser
            435                 440                 445

GTC AAG TAT ATT GCT GAA AAT ATG AAA GCA CAA AAT GAA GCC AAA GAG      1575
Val Lys Tyr Ile Ala Glu Asn Met Lys Ala Gln Asn Glu Ala Lys Glu
            450                 455                 460

ATT CAA GAT GAT TGG AAG TAT GTT GCC ATG GTG ATT GAT CGT ATT TTT      1623
Ile Gln Asp Asp Trp Lys Tyr Val Ala Met Val Ile Asp Arg Ile Phe
            465                 470                 475

CTG TGG GTT TTC ACC CTG GTG TGC ATT CTA GGG ACA GCA GGA TTG TTT      1671
Leu Trp Val Phe Thr Leu Val Cys Ile Leu Gly Thr Ala Gly Leu Phe
            480                 485                 490

CTG CAA CCC CTG ATG GCC AGG GAA GAT GCA TAA GCACTAAGCT GTGTGCCTGC    1724
Leu Gln Pro Leu Met Ala Arg Glu Asp Ala  *
495                 500                 505

CTGGGAGACT TCCTTGTGTC AGGGCAGGAG GAGGCTGCTT CCTAGTAAGA ACGTACTTTC    1784

TGTTATCAAG CTACCAGCTT TGTTTTTGGC ATTTCGAGGT TTACTTATTT TCCACTTATC    1844

TTGGAATCAT GCAAAAAAAA AATGTCAAGA GTATTTATTA CCGATAAATG AACATTTAAC    1904

TAGC                                                                 1908
```

(2) INFORMATION FOR SEQ ID NO: 4:

(i) SEQUENCE CHARACTERISTICS:
        (A) LENGTH: 504 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 4:

```
Met Gly Ser Gly Pro Leu Ser Leu Pro Leu Ala Leu Ser Pro Pro Arg
  1               5                  10                  15

Leu Leu Leu Leu Leu Leu Ser Leu Leu Pro Val Ala Arg Ala Ser Glu
             20                  25                  30

Ala Glu His Arg Leu Phe Glu Arg Leu Phe Glu Asp Tyr Asn Glu Ile
         35                  40                  45

Ile Arg Pro Val Ala Asn Val Ser Asp Pro Val Ile Ile His Phe Glu
 50                  55                  60

Val Ser Met Ser Gln Leu Val Lys Val Asp Glu Val Asn Gln Ile Met
 65                  70                  75                  80

Glu Thr Asn Leu Trp Leu Lys Gln Ile Trp Asn Asp Tyr Lys Leu Lys
                 85                  90                  95

Trp Asn Pro Ser Asp Tyr Gly Gly Ala Glu Phe Met Arg Val Pro Ala
            100                 105                 110

Gln Lys Ile Trp Lys Pro Asp Ile Val Leu Tyr Asn Asn Ala Val Gly
        115                 120                 125

Asp Phe Gln Val Asp Asp Lys Thr Lys Ala Leu Leu Lys Tyr Thr Gly
130                 135                 140

Glu Val Thr Trp Ile Pro Pro Ala Ile Phe Lys Ser Ser Cys Lys Ile
145                 150                 155                 160

Asp Val Thr Tyr Phe Pro Phe Asp Tyr Gln Asn Cys Thr Met Lys Phe
                165                 170                 175

Gly Ser Trp Ser Tyr Asp Lys Ala Lys Ile Asp Leu Val Leu Ile Gly
            180                 185                 190

Ser Ser Met Asn Leu Lys Asp Tyr Trp Glu Ser Gly Glu Trp Ala Ile
        195                 200                 205

Ile Lys Ala Pro Gly Tyr Lys His Asp Ile Lys Tyr Asn Cys Cys Glu
210                 215                 220

Glu Ile Tyr Pro Asp Ile Thr Tyr Ser Leu Tyr Ile Arg Arg Leu Pro
225                 230                 235                 240

Leu Phe Tyr Thr Ile Asn Leu Ile Ile Pro Cys Leu Leu Ile Ser Phe
                245                 250                 255

Leu Thr Val Leu Val Phe Tyr Leu Pro Ser Asp Cys Gly Glu Lys Val
            260                 265                 270

Thr Leu Cys Ile Ser Val Leu Leu Ser Leu Thr Val Phe Leu Leu Val
        275                 280                 285

Ile Thr Glu Thr Ile Pro Ser Thr Ser Leu Val Ile Pro Leu Ile Gly
290                 295                 300

Glu Tyr Leu Leu Phe Thr Met Ile Phe Val Thr Leu Ser Ile Val Ile
305                 310                 315                 320

Thr Val Phe Val Leu Asn Val His Tyr Arg Thr Pro Thr Thr His Thr
                325                 330                 335

Met Pro Ser Trp Val Lys Thr Val Phe Leu Asn Leu Leu Pro Arg Val
            340                 345                 350

Met Phe Met Thr Arg Pro Thr Ser Asn Glu Gly Asn Ala Gln Lys Pro
        355                 360                 365

Arg Pro Leu Tyr Gly Ala Glu Leu Ser Asn Leu Asn Cys Phe Ser Arg
```

```
               370              375              380
Ala Glu Ser Lys Gly Cys Lys Glu Gly Tyr Pro Cys Gln Asp Gly Met
385              390              395              400

Cys Gly Tyr Cys His His Arg Arg Ile Lys Ile Ser Asn Phe Ser Ala
             405              410              415

Asn Leu Thr Arg Ser Ser Ser Glu Ser Val Asp Ala Val Leu Ser
             420              425              430

Leu Ser Ala Leu Ser Pro Glu Ile Lys Glu Ala Ile Gln Ser Val Lys
         435              440              445

Tyr Ile Ala Glu Asn Met Lys Ala Gln Asn Glu Ala Lys Glu Ile Gln
450              455              460

Asp Asp Trp Lys Tyr Val Ala Met Val Ile Asp Arg Ile Phe Leu Trp
465              470              475              480

Val Phe Thr Leu Val Cys Ile Leu Gly Thr Ala Gly Leu Phe Leu Gln
             485              490              495

Pro Leu Met Ala Arg Glu Asp Ala
         500

(2) INFORMATION FOR SEQ ID NO: 5:

(i) SEQUENCE CHARACTERISTICS:
        (A) LENGTH: 3496 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 232...2115
        (D) OTHER INFORMATION: alpha4 subunit human neuronal
            nicotinic acetylcholine receptor (xi) SEQUENCE DESCRIPTION: SEQ ID NO: 5:

TCCCAGCCGG CTGAGGCGGG CAGGGCCGGG CGGGGCCGCG CCACGGAGTC CACAGCCCGG        60

CGCTCCCTGC CGCGCCGCCG CCGCACCGCG CCCCACAGGA GAAGACGAAC CGGGCCCGGC      120

GGCCGAAGCG GCCCGCGAGG CGCGGGAGGC ATGAAGTTGG GCGCGCACGG GCCTCGAAGC      180

GGCGGGGAGC CGGGAGCCGC CCGCATCTAG AGCCCGCGAG GTGCGTGCGC C ATG GAG       237
                                                        Met Glu
                                                          1

CTA GGG GGC CCC GGA GCG CCG CGG CTG CTG CCG CCG CTG CTG CTG CTT        285
Leu Gly Gly Pro Gly Ala Pro Arg Leu Leu Pro Pro Leu Leu Leu Leu
        5                  10                  15

CTG GGG ACC GGC CTC CTG CGC GCC AGC AGC CAT GTG GAG ACC CGG GCC        333
Leu Gly Thr Gly Leu Leu Arg Ala Ser Ser His Val Glu Thr Arg Ala
 20                  25                  30

CAC GCC GAG GAG CGG CTC CTG AAG AAA CTC TTC TCC GGT TAC AAC AAG        381
His Ala Glu Glu Arg Leu Leu Lys Lys Leu Phe Ser Gly Tyr Asn Lys
 35                  40                  45                  50

TGG TCC CGA CCC GTG GCC AAC ATC TCG GAC GTG GTC CTC GTC CGC TTC        429
Trp Ser Arg Pro Val Ala Asn Ile Ser Asp Val Val Leu Val Arg Phe
             55                  60                  65
```

-continued

| | |
|---|---|
| GGC CTG TCC ATC GCT CAG CTC ATT GAC GTG GAT GAG AAG AAC CAG ATG<br>Gly Leu Ser Ile Ala Gln Leu Ile Asp Val Asp Glu Lys Asn Gln Met<br>          70                      75                        80 | 477 |
| ATG ACC ACG AAC GTA TGG GTG AAG CAG GAG TGG CAC GAC TAC AAG CTG<br>Met Thr Thr Asn Val Trp Val Lys Gln Glu Trp His Asp Tyr Lys Leu<br>                85                     90                        95 | 525 |
| CGC TGG GAC CCA GCT GAC TAT GAG AAT GTC ACC TCC ATC CGC ATC CCC<br>Arg Trp Asp Pro Ala Asp Tyr Glu Asn Val Thr Ser Ile Arg Ile Pro<br>100                        105                     110 | 573 |
| TCC GAG CTC ATC TGG CGG CCG GAC ATC GTC CTC TAC AAC AAT GCT GAC<br>Ser Glu Leu Ile Trp Arg Pro Asp Ile Val Leu Tyr Asn Asn Ala Asp<br>115                     120                    125                  130 | 621 |
| GGG GAC TTC GCG GTC ACC CAC CTG ACC AAG GCC CAC CTG TTC CAT GAC<br>Gly Asp Phe Ala Val Thr His Leu Thr Lys Ala His Leu Phe His Asp<br>                     135                    140                    145 | 669 |
| GGG CGG GTG CAG TGG ACT CCC CCG GCC ATT TAC AAG AGC TCC TGC AGC<br>Gly Arg Val Gln Trp Thr Pro Pro Ala Ile Tyr Lys Ser Ser Cys Ser<br>                    150                    155                    160 | 717 |
| ATC GAC GTC ACC TTC TTC CCC TTC GAC CAG CAG AAC TGC ACC ATG AAA<br>Ile Asp Val Thr Phe Phe Pro Phe Asp Gln Gln Asn Cys Thr Met Lys<br>           165                    170                    175 | 765 |
| TTC GGC TCC TGG ACC TAC GAC AAG GCC AAG ATC GAC CTG GTG AAC ATG<br>Phe Gly Ser Trp Thr Tyr Asp Lys Ala Lys Ile Asp Leu Val Asn Met<br>180                       185                    190 | 813 |
| CAC AGC CGC GTG GAC CAG CTG GAC TTC TGG GAG AGT GGC GAG TGG GTC<br>His Ser Arg Val Asp Gln Leu Asp Phe Trp Glu Ser Gly Glu Trp Val<br>195                     200                    205                    210 | 861 |
| ATC GTG GAC GCC GTG GGC ACC TAC AAC ACC AGG AAG TAC GAG TGC TGC<br>Ile Val Asp Ala Val Gly Thr Tyr Asn Thr Arg Lys Tyr Glu Cys Cys<br>                    215                    220                    225 | 909 |
| GCC GAG ATC TAC CCG GAC ATC ACC TAT GCC TTC GTC ATC CGG CGG CTG<br>Ala Glu Ile Tyr Pro Asp Ile Thr Tyr Ala Phe Val Ile Arg Arg Leu<br>                    230                    235                    240 | 957 |
| CCG CTC TTC TAC ACC ATC AAC CTC ATC ATC CCC TGC CTG CTC ATC TCC<br>Pro Leu Phe Tyr Thr Ile Asn Leu Ile Ile Pro Cys Leu Leu Ile Ser<br>                     245                    250                    255 | 1005 |
| TGC CTC ACC GTG CTG GTC TTC TAC CTG CCC TCC GAG TGT GGC GAG AAG<br>Cys Leu Thr Val Leu Val Phe Tyr Leu Pro Ser Glu Cys Gly Glu Lys<br>260                       265                    270 | 1053 |
| ATC ACG CTG TGC ATC TCC GTG CTG CTG TCG CTC ACC GTC TTC CTG CTG<br>Ile Thr Leu Cys Ile Ser Val Leu Leu Ser Leu Thr Val Phe Leu Leu<br>275                       280                    285                    290 | 1101 |
| CTC ATC ACC GAG ATC ATC CCG TCC ACC TCA CTG GTC ATC CCA CTC ATC<br>Leu Ile Thr Glu Ile Ile Pro Ser Thr Ser Leu Val Ile Pro Leu Ile<br>                    295                    300                    305 | 1149 |
| GGC GAG TAC CTG CTG TTC ACC ATG ATC TTC GTC ACC CTG TCC ATC GTC<br>Gly Glu Tyr Leu Leu Phe Thr Met Ile Phe Val Thr Leu Ser Ile Val<br>           310                    315                    320 | 1197 |
| ATC ACG GTC TTC GTG CTC AAC GTG CAC CAC CGC TCG CCA CGC ACG CAC<br>Ile Thr Val Phe Val Leu Asn Val His His Arg Ser Pro Arg Thr His<br>                     325                    330                    335 | 1245 |
| ACC ATG CCC ACC TGG GTA CGC AGG GTC TTC CTG GAC ATC GTG CCA CGC<br>Thr Met Pro Thr Trp Val Arg Arg Val Phe Leu Asp Ile Val Pro Arg<br>340                       345                    350 | 1293 |
| CTG CTC CTC ATG AAG CGG CCG TCC GTG GTC AAG GAC AAT TGC CGG CGG<br>Leu Leu Leu Met Lys Arg Pro Ser Val Val Lys Asp Asn Cys Arg Arg<br>355                       360                    365                    370 | 1341 |
| CTC ATC GAG TCC ATG CAT AAG ATG GCC AGT GCC CCG CGC TTC TGG CCC<br>Leu Ile Glu Ser Met His Lys Met Ala Ser Ala Pro Arg Phe Trp Pro<br>                    375                    380                    385 | 1389 |

```
GAG CCA GAA GGG GAG CCC CCT GCC ACG AGC GGC ACC CAG AGC CTG CAC        1437
Glu Pro Glu Gly Glu Pro Pro Ala Thr Ser Gly Thr Gln Ser Leu His
            390                 395                 400

CCT CCC TCA CCG TCC TTC TGC GTC CCC CTG GAT GTG CCG GCT GAG CCT        1485
Pro Pro Ser Pro Ser Phe Cys Val Pro Leu Asp Val Pro Ala Glu Pro
                405                 410                 415

GGG CCT TCC TGC AAG TCA CCC TCC GAC CAG CTC CCT CCT CAG CAG CCC        1533
Gly Pro Ser Cys Lys Ser Pro Ser Asp Gln Leu Pro Pro Gln Gln Pro
        420                 425                 430

CTG GAA GCT GAG AAA GCC AGC CCC CAC CCC TCG CCT GGA CCC TGC CGC        1581
Leu Glu Ala Glu Lys Ala Ser Pro His Pro Ser Pro Gly Pro Cys Arg
435                 440                 445                 450

CCG CCC CAC GGC ACC CAG GCA CCA GGG CTG GCC AAA GCC AGG TCC CTC        1629
Pro Pro His Gly Thr Gln Ala Pro Gly Leu Ala Lys Ala Arg Ser Leu
                455                 460                 465

AGC GTC CAG CAC ATG TCC AGC CCT GGC GAA GCG GTG GAA GGC GGC GTC        1677
Ser Val Gln His Met Ser Ser Pro Gly Glu Ala Val Glu Gly Gly Val
            470                 475                 480

CGG TGC CGG TCT CGG AGC ATC CAG TAC TGT GTT CCC CGA GAC GAT GCC        1725
Arg Cys Arg Ser Arg Ser Ile Gln Tyr Cys Val Pro Arg Asp Asp Ala
        485                 490                 495

GCC CCC GAG GCA GAT GGC CAG GCT GCC GGC GCC CTG GCC TCT CGC AAC        1773
Ala Pro Glu Ala Asp Gly Gln Ala Ala Gly Ala Leu Ala Ser Arg Asn
500                 505                 510

ACC CAC TCG GCT GAG CTC CCA CCC CCA GAC CAG CCC TCT CCG TGC AAA        1821
Thr His Ser Ala Glu Leu Pro Pro Pro Asp Gln Pro Ser Pro Cys Lys
515                 520                 525                 530

TGC ACA TGC AAG AAG GAG CCC TCT TCG GTG TCC CCG AGC GCC ACG GTC        1869
Cys Thr Cys Lys Lys Glu Pro Ser Ser Val Ser Pro Ser Ala Thr Val
                535                 540                 545

AAG ACC CGC AGC ACC AAA GCG CCG CCC CCG CAC CTG CCC CTG TCG CCG        1917
Lys Thr Arg Ser Thr Lys Ala Pro Pro Pro His Leu Pro Leu Ser Pro
            550                 555                 560

GCC CTG ACC CGG GCG GTG GAG GGC GTC CAG TAC ATT GCA GAC CAC CTG        1965
Ala Leu Thr Arg Ala Val Glu Gly Val Gln Tyr Ile Ala Asp His Leu
        565                 570                 575

AAG GCC GAA GAC ACA GAC TTC TCG GTG AAG GAG GAC TGG AAG TAC GTG        2013
Lys Ala Glu Asp Thr Asp Phe Ser Val Lys Glu Asp Trp Lys Tyr Val
580                 585                 590

GCC ATG GTC ATC GAC CGC ATC TTC CTC TGG ATG TTC ATC ATC GTC TGC        2061
Ala Met Val Ile Asp Arg Ile Phe Leu Trp Met Phe Ile Ile Val Cys
595                 600                 605                 610

CTG CTG GGG ACG GTG GGC CTC TTC CTG CCG CCC TGG CTG GCT GGC ATG        2109
Leu Leu Gly Thr Val Gly Leu Phe Leu Pro Pro Trp Leu Ala Gly Met
                615                 620                 625

ATC TAG GAAGGGACCG GGAGCCTGCG TGGCCTGGGG CTGCCGTGCA CGGGGCCAGC ATC    2168
Ile *

CATGCGGCCG GCCTGGGGCC GGGCTGGCTT CTCCCTGGAC TCTGTGGGGC CACACGTTTG       2228

CCAAATTTTC CTTCCTGTTC TGTGTCTGCT GTAAGACGGC CTTGGACGGG GACACGGCCT       2288

CTGGGGAGAC CGAGTGTGGA GCTGCTTCCA GTTGGACTGT GGCCTCAGGA GGCAGTGGCT       2348

TGGAGCAGAG GTGGGGGTCG CCGCCTTCTA CCTGCAGGAC TCGGGCTAAG TCCAGCTCTC       2408

CCCCTGCGCA GCCCTCCGCG GCGGACAGGA ACACCAGCCC CAGCGAGTCT GGAGACCAGG       2468

ACTCTGCCTT CCAGGCGTAG GGCCAGGGCT CTGGCAGGTG GCCAGGGCTC ACGGGGGGC        2528

TAGTGGCTTC AGCCCCTGGG GTACTTCTGT GTTGTGATTC CCCGGAGCTG GAAGGTCCC        2588

GAATGGAGTC CAGACCTGGG CCCTGGTTCC CCCAGGACCC TGAGGGTTTC CACCTTGGCG       2648
```

-continued

```
CGCAGCCCGG GAGATCCGCC CTGGGCTCTG GGTTCGGGAA GAAGGACTTC CTGCTACAGT    2708

AGCTGTGGGG AGCTGGTGGG GGCATCCTTG AGGACCTCCA CCTGGGAGAT GCTGGGACCC    2768

TCGGGGCAGG AAGTCCCTGA GAAGCCTCAT GGGAGTCAGG GAGCCCTGGG GTTTCCACAC    2828

AGGCCCATGC CCTCCGTCCT GGCAGGGCAG GCAGAGCTCA GCACAGCCTC ACCCCTGCAG    2888

GCGGTATCCA GAGGTGAGGG AGGCCTGAAA TGTTTCCAGG CATGACCCTG GAGCCCGGCA    2948

GTGCACCCCC TAAAGATGGC GCACCCGGCA GCCCCCCATT GTCCCAGGG GCACACTTCC    3008

CCCTTGGGAT GGGCACAGCC TGCCCCACCC CTCCATGATT CCAAGGGCCA AGAGGGGCGG    3068

GGCCAGGATG GCTTTTCCCC TGCCTGTGAG TGACATCGGT TCAGGAGGAG ACAGTCAGGA    3128

AGCCTCCTGC TGAGTGGTCC ACATTCTGCT GCCCCAGAC CCCATCCAGC CAGGGGTGGG     3188

GATGGGGTTG GGCTCTGCGT CCCACTGAGT CTCATTCCTC TGTCCCCGAG CCGAGCTCTC    3248

CTGGGCCAGG GTCTCGTCAG GAGGTGCCTG AGAGCAGAAT GAATAATTGA GGTTAGGAAC    3308

CCGGCATGCC GAGTGCCCCA GAAATGCCGC TGTGTNCCCC GCGGGCAGTG ACGTGAGTGG    3368

GGAGGAGACT CAGGCCCACA TTGCCCACAC CTGCCTCTGA ACTGCTGCTG GTCACCCCCA    3428

CCCCCGGGTG CCTGTGACCG GGGTCCTGAG GCTGGGGCTT TTGTGCCAGG AGTGGGTGGG    3488

ACACAGAG                                                             3496
```

(2) INFORMATION FOR SEQ ID NO: 6:

(i) SEQUENCE CHARACTERISTICS:
        (A) LENGTH: 627 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 6:

```
Met Glu Leu Gly Gly Pro Gly Ala Pro Arg Leu Leu Pro Pro Leu Leu
 1               5                  10                  15

Leu Leu Leu Gly Thr Gly Leu Leu Arg Ala Ser Ser His Val Glu Thr
                20                  25                  30

Arg Ala His Ala Glu Glu Arg Leu Leu Lys Lys Leu Phe Ser Gly Tyr
            35                  40                  45

Asn Lys Trp Ser Arg Pro Val Ala Asn Ile Ser Asp Val Val Leu Val
    50                  55                  60

Arg Phe Gly Leu Ser Ile Ala Gln Leu Ile Asp Val Asp Glu Lys Asn
65                  70                  75                  80

Gln Met Met Thr Thr Asn Val Trp Val Lys Gln Glu Trp His Asp Tyr
                85                  90                  95

Lys Leu Arg Trp Asp Pro Ala Asp Tyr Glu Asn Val Thr Ser Ile Arg
            100                 105                 110

Ile Pro Ser Glu Leu Ile Trp Arg Pro Asp Ile Val Leu Tyr Asn Asn
        115                 120                 125

Ala Asp Gly Asp Phe Ala Val Thr His Leu Thr Lys Ala His Leu Phe
    130                 135                 140
```

-continued

His Asp Gly Arg Val Gln Trp Thr Pro Pro Ala Ile Tyr Lys Ser Ser
145                 150                 155                 160

Cys Ser Ile Asp Val Thr Phe Phe Pro Phe Asp Gln Gln Asn Cys Thr
                165                 170                 175

Met Lys Phe Gly Ser Trp Thr Tyr Asp Lys Ala Lys Ile Asp Leu Val
            180                 185                 190

Asn Met His Ser Arg Val Asp Gln Leu Asp Phe Trp Glu Ser Gly Glu
        195                 200                 205

Trp Val Ile Val Asp Ala Val Gly Thr Tyr Asn Thr Arg Lys Tyr Glu
    210                 215                 220

Cys Cys Ala Glu Ile Tyr Pro Asp Ile Thr Tyr Ala Phe Val Ile Arg
225                 230                 235                 240

Arg Leu Pro Leu Phe Tyr Thr Ile Asn Leu Ile Ile Pro Cys Leu Leu
                245                 250                 255

Ile Ser Cys Leu Thr Val Leu Val Phe Tyr Leu Pro Ser Glu Cys Gly
            260                 265                 270

Glu Lys Ile Thr Leu Cys Ile Ser Val Leu Leu Ser Leu Thr Val Phe
        275                 280                 285

Leu Leu Leu Ile Thr Glu Ile Ile Pro Ser Thr Ser Leu Val Ile Pro
    290                 295                 300

Leu Ile Gly Glu Tyr Leu Leu Phe Thr Met Ile Phe Val Thr Leu Ser
305                 310                 315                 320

Ile Val Ile Thr Val Phe Val Leu Asn Val His His Arg Ser Pro Arg
                325                 330                 335

Thr His Thr Met Pro Thr Trp Val Arg Arg Val Phe Leu Asp Ile Val
            340                 345                 350

Pro Arg Leu Leu Leu Met Lys Arg Pro Ser Val Val Lys Asp Asn Cys
        355                 360                 365

Arg Arg Leu Ile Glu Ser Met His Lys Met Ala Ser Ala Pro Arg Phe
    370                 375                 380

Trp Pro Glu Pro Glu Gly Glu Pro Pro Ala Thr Ser Gly Thr Gln Ser
385                 390                 395                 400

Leu His Pro Pro Ser Pro Ser Phe Cys Val Pro Leu Asp Val Pro Ala
                405                 410                 415

Glu Pro Gly Pro Ser Cys Lys Ser Pro Ser Asp Gln Leu Pro Pro Gln
            420                 425                 430

Gln Pro Leu Glu Ala Glu Lys Ala Ser Pro His Pro Ser Pro Gly Pro
        435                 440                 445

Cys Arg Pro Pro His Gly Thr Gln Ala Pro Gly Leu Ala Lys Ala Arg
    450                 455                 460

Ser Leu Ser Val Gln His Met Ser Ser Pro Gly Glu Ala Val Glu Gly
465                 470                 475                 480

Gly Val Arg Cys Arg Ser Arg Ser Ile Gln Tyr Cys Val Pro Arg Asp
                485                 490                 495

Asp Ala Ala Pro Glu Ala Asp Gly Gln Ala Ala Gly Ala Leu Ala Ser
            500                 505                 510

Arg Asn Thr His Ser Ala Glu Leu Pro Pro Asp Gln Pro Ser Pro
        515                 520                 525

Cys Lys Cys Thr Cys Lys Lys Glu Pro Ser Ser Val Ser Pro Ser Ala
    530                 535                 540

Thr Val Lys Thr Arg Ser Thr Lys Ala Pro Pro Pro His Leu Pro Leu
545                 550                 555                 560

Ser Pro Ala Leu Thr Arg Ala Val Glu Gly Val Gln Tyr Ile Ala Asp

```
                565                 570                 575
His Leu Lys Ala Glu Asp Thr Asp Phe Ser Val Lys Glu Asp Trp Lys
            580                 585                 590

Tyr Val Ala Met Val Ile Asp Arg Ile Phe Leu Trp Met Phe Ile Ile
            595                 600                 605

Val Cys Leu Leu Gly Thr Val Gly Leu Phe Leu Pro Pro Trp Leu Ala
            610                 615                 620

Gly Met Ile
625

(2) INFORMATION FOR SEQ ID NO: 7:

(i) SEQUENCE CHARACTERISTICS:
        (A) LENGTH: 1828 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 155...1561
        (D) OTHER INFORMATION: alpha5 subunit human neuronal
            nicotinic acetylcholine receptor (xi) SEQUENCE DESCRIPTION: SEQ ID NO: 7:

CCCGGCGGGA GCTGTGGCGC GGAGCGGCCC CGCTGCTGCG TCTGCCCTCG TTTTGTCTCA    60

CGACTCACAC TCAGTGCTGC ATTCCCCAAG AGTTCGCGTT CCCCGCGCGG CGGTCGAGAG   120

GCGGCTGCCC GCGGTCCCGC GCGGGCGCGG GGCG ATG GCG GCG CGG GGG TCA GGG   175
                                     Met Ala Ala Arg Gly Ser Gly
                                       1               5

CCC CGC GCG CTC CGC CTG CTG CTC TTG GTC CAG CTG GTC GCG GGG CGC    223
Pro Arg Ala Leu Arg Leu Leu Leu Leu Val Gln Leu Val Ala Gly Arg
            10                  15                  20

TGC GGT CTA GCG GGC GCG GCG GGC GGC GCG CAG AGA GGA TTA TCT GAA    271
Cys Gly Leu Ala Gly Ala Ala Gly Gly Ala Gln Arg Gly Leu Ser Glu
        25                  30                  35

CCT TCT TCT ATT GCA AAA CAT GAA GAT AGT TTG CTT AAG GAT TTA TTT    319
Pro Ser Ser Ile Ala Lys His Glu Asp Ser Leu Leu Lys Asp Leu Phe
40                  45                  50                  55

CAA GAC TAC GAA AGA TGG GTT CGT CCT GTG GAA CAC CTG AAT GAC AAA    367
Gln Asp Tyr Glu Arg Trp Val Arg Pro Val Glu His Leu Asn Asp Lys
                60                  65                  70

ATA AAA ATA AAA TTT GGA CTT GCA ATA TCT CAA TTG GTG GAT GTG GAT    415
Ile Lys Ile Lys Phe Gly Leu Ala Ile Ser Gln Leu Val Asp Val Asp
            75                  80                  85

GAG AAA AAT CAG TTA ATG ACA ACA AAC GTC TGG TTG AAA CAG GAA TGG    463
Glu Lys Asn Gln Leu Met Thr Thr Asn Val Trp Leu Lys Gln Glu Trp
        90                  95                  100

ATA GAT GTA AAA TTA AGA TGG AAC CCT GAT GAC TAT GGT GGA ATA AAA    511
Ile Asp Val Lys Leu Arg Trp Asn Pro Asp Asp Tyr Gly Gly Ile Lys
    105                 110                 115

GTT ATA CGT GTT CCT TCA GAC TCT GTC TGG ACA CCA GAC ATC GTT TTG    559
Val Ile Arg Val Pro Ser Asp Ser Val Trp Thr Pro Asp Ile Val Leu
```

```
                      -continued
120                 125                 130                 135

TTT GAT AAT GCA GAT GGA CGT TTT GAA GGG ACC AGT ACG AAA ACA GTC      607
Phe Asp Asn Ala Asp Gly Arg Phe Glu Gly Thr Ser Thr Lys Thr Val
                140                 145                 150

ATC AGG TAC AAT GGC ACT GTC ACC TGG ACT CCA CCG GCA AAC TAC AAA      655
Ile Arg Tyr Asn Gly Thr Val Thr Trp Thr Pro Pro Ala Asn Tyr Lys
                155                 160                 165

AGT TCC TGT ACC ATA GAT GTC ACG TTT TTC CCA TTT GAC CTT CAG AAC      703
Ser Ser Cys Thr Ile Asp Val Thr Phe Phe Pro Phe Asp Leu Gln Asn
                170                 175                 180

TGT TCC ATG AAA TTT GGT TCT TGG ACT TAT GAT GGA TCA CAG GTT GAT      751
Cys Ser Met Lys Phe Gly Ser Trp Thr Tyr Asp Gly Ser Gln Val Asp
        185                 190                 195

ATA ATT CTA GAG GAC CAA GAT GTA GAC AAG AGA GAT TTT TTT GAT AAT      799
Ile Ile Leu Glu Asp Gln Asp Val Asp Lys Arg Asp Phe Phe Asp Asn
200                 205                 210                 215

GGA GAA TGG GAG ATT GTG AGT GCA ACA GGG AGC AAA GGA AAC AGA ACC      847
Gly Glu Trp Glu Ile Val Ser Ala Thr Gly Ser Lys Gly Asn Arg Thr
                220                 225                 230

GAC AGC TGT TGC TGG TAT CCG TAT GTC ACT TAC TCA TTT GTA ATC AAG      895
Asp Ser Cys Cys Trp Tyr Pro Tyr Val Thr Tyr Ser Phe Val Ile Lys
                235                 240                 245

CGC CTG CCT CTC TTT TAT ACC TTG TTC CTT ATA ATA CCC TGT ATT GGG      943
Arg Leu Pro Leu Phe Tyr Thr Leu Phe Leu Ile Ile Pro Cys Ile Gly
                250                 255                 260

CTC TCA TTT TTA ACT GTA CTT GTC TTC TAT CTT CCT TCA AAT GAA GGT      991
Leu Ser Phe Leu Thr Val Leu Val Phe Tyr Leu Pro Ser Asn Glu Gly
            265                 270                 275

GAA AAG ATT TGT CTC TGC ACT TCA GTA CTT GTG TCT TTG ACT GTC TTC     1039
Glu Lys Ile Cys Leu Cys Thr Ser Val Leu Val Ser Leu Thr Val Phe
280                 285                 290                 295

CTT CTG GTT ATT GAA GAG ATC ATA CCA TCA TCT TCA AAA GTC ATA CCT     1087
Leu Leu Val Ile Glu Glu Ile Ile Pro Ser Ser Ser Lys Val Ile Pro
                300                 305                 310

CTA ATT GGA GAG TAT CTG GTA TTT ACC ATG ATT TTT GTG ACA CTG TCA     1135
Leu Ile Gly Glu Tyr Leu Val Phe Thr Met Ile Phe Val Thr Leu Ser
                315                 320                 325

ATT ATG GTA ACC GTC TTC GCT ATC AAC ATT CAT CAT CGT TCT TCC TCA     1183
Ile Met Val Thr Val Phe Ala Ile Asn Ile His His Arg Ser Ser Ser
                330                 335                 340

ACA CAT AAT GCC ATG GCG CCT TTG GTC CGC AAG ATA TTT CTT CAC ACG     1231
Thr His Asn Ala Met Ala Pro Leu Val Arg Lys Ile Phe Leu His Thr
            345                 350                 355

CTT CCC AAA CTG CTT TGC ATG AGA AGT CAT GTA GAC AGG TAC TTC ACT     1279
Leu Pro Lys Leu Leu Cys Met Arg Ser His Val Asp Arg Tyr Phe Thr
360                 365                 370                 375

CAG AAA GAG GAA ACT GAG AGT GGT AGT GGA CCA AAA TCT TCT AGA AAC     1327
Gln Lys Glu Glu Thr Glu Ser Gly Ser Gly Pro Lys Ser Ser Arg Asn
                380                 385                 390

ACA TTG GAA GCT GCG CTC AAT TCT ATT CGC TAC ATT ACA AGA CAC ATC     1375
Thr Leu Glu Ala Ala Leu Asn Ser Ile Arg Tyr Ile Thr Arg His Ile
                395                 400                 405

ATG AAG GAA AAT GAT GTC CGT GAG GTT GTT GAA GAT TGG AAA TTC ATA     1423
Met Lys Glu Asn Asp Val Arg Glu Val Val Glu Asp Trp Lys Phe Ile
                410                 415                 420

GCC CAG GTT CTT GAT CGG ATG TTT CTG TGG ACT TTT CTT TTC GTT TCA     1471
Ala Gln Val Leu Asp Arg Met Phe Leu Trp Thr Phe Leu Phe Val Ser
            425                 430                 435

ATT GTT GGA TCT CTT GGG CTT TTT GTT CCT GTT ATT TAT AAA TGG GCA     1519
```

```
Ile Val Gly Ser Leu Gly Leu Phe Val Pro Val Ile Tyr Lys Trp Ala
440                 445                 450                 455

AAT ATA TTA ATA CCA GTT CAT ATT GGA AAT GCA AAT AAG TGA AGCCTCCCAA   1571
Asn Ile Leu Ile Pro Val His Ile Gly Asn Ala Asn Lys  *
                    460                 465

GGGACTGAAG TATACATTTA GTTAACACAC ATATATCTGA TGGCACCTAT AAAATTATGA    1631

AAATGTAAGT TATGTGTTAA ATTTAGTGCA AGCTTTAACA GACTAAGTTG CTAACCTCAA    1691

TTTATGTTAA CAGATGATCC ATTTGAACAG TTGGCTGTAT GACTGAAGTA ATAACTGATG    1751

AGATACATTT GATCTTGTAA AAATAGCAAA ATATTATCTG AACTGGACTA GTGAAAAATC    1811

TAGTATTTGT ATCCTGG                                                   1828

(2) INFORMATION FOR SEQ ID NO: 8:

(i) SEQUENCE CHARACTERISTICS:
        (A) LENGTH: 468 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 8:

Met Ala Ala Arg Gly Ser Gly Pro Arg Ala Leu Arg Leu Leu Leu Leu
1               5                   10                  15

Val Gln Leu Val Ala Gly Arg Cys Gly Leu Ala Gly Ala Ala Gly Gly
                20                  25                  30

Ala Gln Arg Gly Leu Ser Glu Pro Ser Ser Ile Ala Lys His Glu Asp
            35                  40                  45

Ser Leu Leu Lys Asp Leu Phe Gln Asp Tyr Glu Arg Trp Val Arg Pro
50                  55                  60

Val Glu His Leu Asn Asp Lys Ile Lys Ile Lys Phe Gly Leu Ala Ile
65                  70                  75                  80

Ser Gln Leu Val Asp Val Asp Glu Lys Asn Gln Leu Met Thr Thr Asn
                85                  90                  95

Val Trp Leu Lys Gln Glu Trp Ile Asp Val Lys Leu Arg Trp Asn Pro
                100                 105                 110

Asp Asp Tyr Gly Gly Ile Lys Val Ile Arg Val Pro Ser Asp Ser Val
                115                 120                 125

Trp Thr Pro Asp Ile Val Leu Phe Asp Asn Ala Asp Gly Arg Phe Glu
            130                 135                 140

Gly Thr Ser Thr Lys Thr Val Ile Arg Tyr Asn Gly Thr Val Thr Trp
145                 150                 155                 160

Thr Pro Pro Ala Asn Tyr Lys Ser Ser Cys Thr Ile Asp Val Thr Phe
                165                 170                 175

Phe Pro Phe Asp Leu Gln Asn Cys Ser Met Lys Phe Gly Ser Trp Thr
                180                 185                 190

Tyr Asp Gly Ser Gln Val Asp Ile Ile Leu Glu Asp Gln Asp Val Asp
            195                 200                 205

Lys Arg Asp Phe Phe Asp Asn Gly Glu Trp Glu Ile Val Ser Ala Thr
210                 215                 220
```

```
Gly Ser Lys Gly Asn Arg Thr Asp Ser Cys Cys Trp Tyr Pro Tyr Val
225                 230                 235                 240

Thr Tyr Ser Phe Val Ile Lys Arg Leu Pro Leu Phe Tyr Thr Leu Phe
            245                 250                 255

Leu Ile Ile Pro Cys Ile Gly Leu Ser Phe Leu Thr Val Leu Val Phe
            260                 265                 270

Tyr Leu Pro Ser Asn Glu Gly Glu Lys Ile Cys Leu Cys Thr Ser Val
            275                 280                 285

Leu Val Ser Leu Thr Val Phe Leu Leu Val Ile Glu Glu Ile Ile Pro
290                 295                 300

Ser Ser Ser Lys Val Ile Pro Leu Ile Gly Glu Tyr Leu Val Phe Thr
305                 310                 315                 320

Met Ile Phe Val Thr Leu Ser Ile Met Val Thr Val Phe Ala Ile Asn
                325                 330                 335

Ile His His Arg Ser Ser Ser Thr His Asn Ala Met Ala Pro Leu Val
                340                 345                 350

Arg Lys Ile Phe Leu His Thr Leu Pro Lys Leu Leu Cys Met Arg Ser
            355                 360                 365

His Val Asp Arg Tyr Phe Thr Gln Lys Glu Glu Thr Glu Ser Gly Ser
370                 375                 380

Gly Pro Lys Ser Ser Arg Asn Thr Leu Glu Ala Ala Leu Asn Ser Ile
385                 390                 395                 400

Arg Tyr Ile Thr Arg His Ile Met Lys Glu Asn Asp Val Arg Glu Val
                405                 410                 415

Val Glu Asp Trp Lys Phe Ile Ala Gln Val Leu Asp Arg Met Phe Leu
            420                 425                 430

Trp Thr Phe Leu Phe Val Ser Ile Val Gly Ser Leu Gly Leu Phe Val
            435                 440                 445

Pro Val Ile Tyr Lys Trp Ala Asn Ile Leu Ile Pro Val His Ile Gly
            450                 455                 460

Asn Ala Asn Lys
465

(2) INFORMATION FOR SEQ ID NO: 9:

(i) SEQUENCE CHARACTERISTICS:
        (A) LENGTH: 1743 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 143...1627
        (D) OTHER INFORMATION: alpha6 subunit human neuronal
            nicotinic acetylcholine receptor (xi) SEQUENCE DESCRIPTION: SEQ ID NO: 9:

CGGGTTTTGA TTTCTGAGAA GACACACACG GATTGCAGTG GGCTTCTGAT GATGTCAAGG       60

TTGGATGCAT GTGGCTGACT GATAGCTCTT TGTTTTCCAC AATCCTTTGC CTAGGAAAAA     120
```

-continued

| | | |
|---|---|---|
| GGAATCCAAG TGTGTTTTAA CC ATG CTG ACC AGC AAG GGG CAG GGA TTC CTT | 172 | |
| Met Leu Thr Ser Lys Gly Gln Gly Phe Leu | | |
| 1 5 10 | | |
| CAT GGG GGC TTG TGT CTC TGG CTG TGT GTG TTC ACA CCT TTC TTT AAA | 220 | |
| His Gly Gly Leu Cys Leu Trp Leu Cys Val Phe Thr Pro Phe Phe Lys | | |
| 15 20 25 | | |
| GGC TGT GTG GGC TGT GCA ACT GAG GAG AGG CTC TTC CAC AAA CTG TTT | 268 | |
| Gly Cys Val Gly Cys Ala Thr Glu Glu Arg Leu Phe His Lys Leu Phe | | |
| 30 35 40 | | |
| TCT CAT TAC AAC CAG TTC ATC AGG CCT GTG GAA AAC GTT TCC GAC CCT | 316 | |
| Ser His Tyr Asn Gln Phe Ile Arg Pro Val Glu Asn Val Ser Asp Pro | | |
| 45 50 55 | | |
| GTC ACG GTA CAC TTT GAA GTG GCC ATC ACC CAG CTG GCC AAC GTG GAT | 364 | |
| Val Thr Val His Phe Glu Val Ala Ile Thr Gln Leu Ala Asn Val Asp | | |
| 60 65 70 | | |
| GAA GTA AAC CAG ATC ATG GAA ACC AAT TTG TGG CTG CGT CAC ATC TGG | 412 | |
| Glu Val Asn Gln Ile Met Glu Thr Asn Leu Trp Leu Arg His Ile Trp | | |
| 75 80 85 90 | | |
| AAT GAT TAT AAA TTG CGC TGG GAT CCA ATG GAA TAT GAT GGC ATT GAG | 460 | |
| Asn Asp Tyr Lys Leu Arg Trp Asp Pro Met Glu Tyr Asp Gly Ile Glu | | |
| 95 100 105 | | |
| ACT CTT CGC GTT CCT GCA GAT AAG ATT TGG AAG CCC GAC ATT GTT CTC | 508 | |
| Thr Leu Arg Val Pro Ala Asp Lys Ile Trp Lys Pro Asp Ile Val Leu | | |
| 110 115 120 | | |
| TAT AAC AAT GCT GTT GGT GAC TTC CAA GTA GAA GGC AAA ACA AAA GCT | 556 | |
| Tyr Asn Asn Ala Val Gly Asp Phe Gln Val Glu Gly Lys Thr Lys Ala | | |
| 125 130 135 | | |
| CTT CTT AAA TAC AAT GGC ATG ATA ACC TGG ACT CCA CCA GCT ATT TTT | 604 | |
| Leu Leu Lys Tyr Asn Gly Met Ile Thr Trp Thr Pro Pro Ala Ile Phe | | |
| 140 145 150 | | |
| AAG AGT TCC TGC CCT ATG GAT ATC ACC TTT TTC CCT TTT GAT CAT CAA | 652 | |
| Lys Ser Ser Cys Pro Met Asp Ile Thr Phe Phe Pro Phe Asp His Gln | | |
| 155 160 165 170 | | |
| AAC TGT TCC CTA AAA TTT GGT TCC TGG ACG TAT GAC AAA GCT GAA ATT | 700 | |
| Asn Cys Ser Leu Lys Phe Gly Ser Trp Thr Tyr Asp Lys Ala Glu Ile | | |
| 175 180 185 | | |
| GAT CTT CTA ATC ATT GGA TCA AAA GTG GAT ATG AAT GAT TTT TGG GAA | 748 | |
| Asp Leu Leu Ile Ile Gly Ser Lys Val Asp Met Asn Asp Phe Trp Glu | | |
| 190 195 200 | | |
| AAC AGT GAA TGG GAA ATC ATT GAT GCC TCT GGC TAC AAA CAT GAC ATC | 796 | |
| Asn Ser Glu Trp Glu Ile Ile Asp Ala Ser Gly Tyr Lys His Asp Ile | | |
| 205 210 215 | | |
| AAA TAC AAC TGT TGT GAA GAG ATA TAC ACA GAT ATA ACC TAT TCT TTC | 844 | |
| Lys Tyr Asn Cys Cys Glu Glu Ile Tyr Thr Asp Ile Thr Tyr Ser Phe | | |
| 220 225 230 | | |
| TAC ATT AGA AGA TTG CCG ATG TTT TAC ACG ATT AAT CTG ATC ATC CCT | 892 | |
| Tyr Ile Arg Arg Leu Pro Met Phe Tyr Thr Ile Asn Leu Ile Ile Pro | | |
| 235 240 245 250 | | |
| TGT CTC TTT ATT TCA TTT CTA ACC GTG TTG GTC TTT TAC CTT CCT TCG | 940 | |
| Cys Leu Phe Ile Ser Phe Leu Thr Val Leu Val Phe Tyr Leu Pro Ser | | |
| 255 260 265 | | |
| GAC TGT GGT GAA AAA GTG ACG CTT TGT ATT TCA GTC CTG CTT TCT CTG | 988 | |
| Asp Cys Gly Glu Lys Val Thr Leu Cys Ile Ser Val Leu Leu Ser Leu | | |
| 270 275 280 | | |
| ACT GTG TTT TTG CTG GTC ATC ACA GAA ACC ATC CCA TCC ACA TCT CTG | 1036 | |
| Thr Val Phe Leu Leu Val Ile Thr Glu Thr Ile Pro Ser Thr Ser Leu | | |
| 285 290 295 | | |
| GTG GTC CCA CTG GTG GGT GAG TAC CTG CTG TTC ACC ATG ATC TTT GTC | 1084 | |
| Val Val Pro Leu Val Gly Glu Tyr Leu Leu Phe Thr Met Ile Phe Val | | |

-continued

```
       300              305              310
ACA CTG TCC ATC GTG GTG ACT GTG TTT GTG TTG AAC ATA CAC TAC CGC      1132
Thr Leu Ser Ile Val Val Thr Val Phe Val Leu Asn Ile His Tyr Arg
315              320              325              330

ACC CCA ACC ACG CAC ACA ATG CCC AGG TGG GTG AAG ACA GTT TTC CTG      1180
Thr Pro Thr Thr His Thr Met Pro Arg Trp Val Lys Thr Val Phe Leu
             335              340              345

AAG CTG CTG CCC CAG GTC CTG CTG ATG AGG TGG CCT CTG GAC AAG ACA      1228
Lys Leu Leu Pro Gln Val Leu Leu Met Arg Trp Pro Leu Asp Lys Thr
             350              355              360

AGG GGC ACA GGC TCT GAT GCA GTG CCC AGA GGC CTT GCC AGG AGG CCT      1276
Arg Gly Thr Gly Ser Asp Ala Val Pro Arg Gly Leu Ala Arg Arg Pro
             365              370              375

GCC AAA GGC AAG CTT GCA AGC CAT GGG GAA CCC AGA CAT CTT AAA GAA      1324
Ala Lys Gly Lys Leu Ala Ser His Gly Glu Pro Arg His Leu Lys Glu
             380              385              390

TGC TTC CAT TGT CAC AAA TCA AAT GAG CTT GCC ACA AGC AAG AGA AGA      1372
Cys Phe His Cys His Lys Ser Asn Glu Leu Ala Thr Ser Lys Arg Arg
395              400              405              410

TTA AGT CAT CAG CCA TTA CAG TGG GTG GTG GAA AAT TCG GAG CAC TCG      1420
Leu Ser His Gln Pro Leu Gln Trp Val Val Glu Asn Ser Glu His Ser
             415              420              425

CCT GAA GTT GAA GAT GTG ATT AAC AGT GTT CAG TTC ATA GCA GAA AAC      1468
Pro Glu Val Glu Asp Val Ile Asn Ser Val Gln Phe Ile Ala Glu Asn
             430              435              440

ATG AAG AGC CAC AAT GAA ACC AAG GAG GTA GAA GAT GAC TGG AAA TAC      1516
Met Lys Ser His Asn Glu Thr Lys Glu Val Glu Asp Asp Trp Lys Tyr
             445              450              455

GTG GCC ATG GTG GTG GAC AGA GTA TTT CTT TGG GTA TTT ATA ATT GTC      1564
Val Ala Met Val Val Asp Arg Val Phe Leu Trp Val Phe Ile Ile Val
460              465              470

TGT GTA TTT GGA ACT GCA GGG CTA TTT CTA CAG CCA CTA CTT GGG AAC      1612
Cys Val Phe Gly Thr Ala Gly Leu Phe Leu Gln Pro Leu Leu Gly Asn
475              480              485              490

ACA GGA AAA TCT TAA AATGTATTTT CTTTTATGTT CAGAAATTTA CAGACACCAT AT   1669
Thr Gly Lys Ser *
             495

TTGTTCTGCA TTCCCTGCCA CAAGGAAAGG AAAGCAAAGG CTTCCCACCC AAGTCCCCCA   1729

TCTGCTAAAA CCCG                                                     1743
```

(2) INFORMATION FOR SEQ ID NO: 10:

(i) SEQUENCE CHARACTERISTICS:
        (A) LENGTH: 494 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 10:

```
Met Leu Thr Ser Lys Gly Gln Gly Phe Leu His Gly Gly Leu Cys Leu
1               5                   10                  15

Trp Leu Cys Val Phe Thr Pro Phe Phe Lys Gly Cys Val Gly Cys Ala
```

```
                   20                  25                  30
Thr Glu Glu Arg Leu Phe His Lys Leu Phe Ser His Tyr Asn Gln Phe
                35                  40                  45
Ile Arg Pro Val Glu Asn Val Ser Asp Pro Val Thr Val His Phe Glu
            50                  55                  60
Val Ala Ile Thr Gln Leu Ala Asn Val Asp Glu Val Asn Gln Ile Met
65                  70                  75                  80
Glu Thr Asn Leu Trp Leu Arg His Ile Trp Asn Asp Tyr Lys Leu Arg
                    85                  90                  95
Trp Asp Pro Met Glu Tyr Asp Gly Ile Glu Thr Leu Arg Val Pro Ala
                100                 105                 110
Asp Lys Ile Trp Lys Pro Asp Ile Val Leu Tyr Asn Asn Ala Val Gly
                115                 120                 125
Asp Phe Gln Val Glu Gly Lys Thr Lys Ala Leu Leu Lys Tyr Asn Gly
            130                 135                 140
Met Ile Thr Trp Thr Pro Pro Ala Ile Phe Lys Ser Ser Cys Pro Met
145                 150                 155                 160
Asp Ile Thr Phe Phe Pro Phe Asp His Gln Asn Cys Ser Leu Lys Phe
                    165                 170                 175
Gly Ser Trp Thr Tyr Asp Lys Ala Glu Ile Asp Leu Leu Ile Ile Gly
                180                 185                 190
Ser Lys Val Asp Met Asn Asp Phe Trp Glu Asn Ser Glu Trp Glu Ile
            195                 200                 205
Ile Asp Ala Ser Gly Tyr Lys His Asp Ile Lys Tyr Asn Cys Cys Glu
        210                 215                 220
Glu Ile Tyr Thr Asp Ile Thr Tyr Ser Phe Tyr Ile Arg Arg Leu Pro
225                 230                 235                 240
Met Phe Tyr Thr Ile Asn Leu Ile Ile Pro Cys Leu Phe Ile Ser Phe
                    245                 250                 255
Leu Thr Val Leu Val Phe Tyr Leu Pro Ser Asp Cys Gly Glu Lys Val
                260                 265                 270
Thr Leu Cys Ile Ser Val Leu Leu Ser Leu Thr Val Phe Leu Leu Val
            275                 280                 285
Ile Thr Glu Thr Ile Pro Ser Thr Ser Leu Val Val Pro Leu Val Gly
        290                 295                 300
Glu Tyr Leu Leu Phe Thr Met Ile Phe Val Thr Leu Ser Ile Val Val
305                 310                 315                 320
Thr Val Phe Val Leu Asn Ile His Tyr Arg Thr Pro Thr Thr His Thr
                    325                 330                 335
Met Pro Arg Trp Val Lys Thr Val Phe Leu Lys Leu Leu Pro Gln Val
                340                 345                 350
Leu Leu Met Arg Trp Pro Leu Asp Lys Thr Arg Gly Thr Gly Ser Asp
            355                 360                 365
Ala Val Pro Arg Gly Leu Ala Arg Arg Pro Ala Lys Gly Lys Leu Ala
        370                 375                 380
Ser His Gly Glu Pro Arg His Leu Lys Glu Cys Phe His Cys His Lys
385                 390                 395                 400
Ser Asn Glu Leu Ala Thr Ser Lys Arg Arg Leu Ser His Gln Pro Leu
                    405                 410                 415
Gln Trp Val Val Glu Asn Ser Glu His Ser Pro Glu Val Glu Asp Val
                420                 425                 430
Ile Asn Ser Val Gln Phe Ile Ala Glu Asn Met Lys Ser His Asn Glu
            435                 440                 445
```

```
Thr Lys Glu Val Glu Asp Asp Trp Lys Tyr Val Ala Met Val Val Asp
    450                 455                 460

Arg Val Phe Leu Trp Val Phe Ile Ile Val Cys Val Phe Gly Thr Ala
465                 470                 475                 480

Gly Leu Phe Leu Gln Pro Leu Leu Gly Asn Thr Gly Lys Ser
                485                 490

(2) INFORMATION FOR SEQ ID NO: 11:

(i) SEQUENCE CHARACTERISTICS:
        (A) LENGTH: 1876 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 73...1581
        (D) OTHER INFORMATION: alpha7 human neuronal nicotinic
            acetylcholine receptor (xi) SEQUENCE DESCRIPTION: SEQ ID NO: 11:

GGCCGCAGGC GCAGGCCCGG GCGACAGCCG AGACGTGGAG CGCGCCGGCT CGCTGCAGCT        60

CCGGGACTCA AC ATG CGC TGC TCG CCG GGA GGC GTC TGG CTG GCG CTG GCC      111
              Met Arg Cys Ser Pro Gly Gly Val Trp Leu Ala Leu Ala
                1               5                   10

GCG TCG CTC CTG CAC GTG TCC CTG CAA GGC GAG TTC CAG AGG AAG CTT         159
Ala Ser Leu Leu His Val Ser Leu Gln Gly Glu Phe Gln Arg Lys Leu
 15                  20                  25

TAC AAG GAG CTG GTC AAG AAC TAC AAT CCC TTG GAG AGG CCC GTG GCC         207
Tyr Lys Glu Leu Val Lys Asn Tyr Asn Pro Leu Glu Arg Pro Val Ala
 30                  35                  40                  45

AAT GAC TCG CAA CCA CTC ACC GTC TAC TTC TCC CTG AGC CTC CTG CAG         255
Asn Asp Ser Gln Pro Leu Thr Val Tyr Phe Ser Leu Ser Leu Leu Gln
                 50                  55                  60

ATC ATG GAC GTG GAT GAG AAG AAC CAA GTT TTA ACC ACC AAC ATT TGG         303
Ile Met Asp Val Asp Glu Lys Asn Gln Val Leu Thr Thr Asn Ile Trp
             65                  70                  75

CTG CAA ATG TCT TGG ACA GAT CAC TAT TTA CAG TGG AAT GTG TCA GAA         351
Leu Gln Met Ser Trp Thr Asp His Tyr Leu Gln Trp Asn Val Ser Glu
         80                  85                  90

TAT CCA GGG GTG AAG ACT GTT CGT TTC CCA GAT GGC CAG ATT TGG AAA         399
Tyr Pro Gly Val Lys Thr Val Arg Phe Pro Asp Gly Gln Ile Trp Lys
     95                  100                 105

CCA GAC ATT CTT CTC TAT AAC AGT GCT GAT GAG CGC TTT GAC GCC ACA         447
Pro Asp Ile Leu Leu Tyr Asn Ser Ala Asp Glu Arg Phe Asp Ala Thr
110                 115                 120                 125

TTC CAC ACT AAC GTG TTG GTG AAT TCT TCT GGG CAT TGC CAG TAC CTG         495
Phe His Thr Asn Val Leu Val Asn Ser Ser Gly His Cys Gln Tyr Leu
                130                 135                 140

CCT CCA GGC ATA TTC AAG AGT TCC TGC TAC ATC GAT GTA CGC TGG TTT         543
Pro Pro Gly Ile Phe Lys Ser Ser Cys Tyr Ile Asp Val Arg Trp Phe
            145                 150                 155
```

```
CCC TTT GAT GTG CAG CAC TGC AAA CTG AAG TTT GGG TCC TGG TCT TAC      591
Pro Phe Asp Val Gln His Cys Lys Leu Lys Phe Gly Ser Trp Ser Tyr
        160                 165                 170

GGA GGC TGG TCC TTG GAT CTG CAG ATG CAG GAG GCA GAT ATC AGT GGC      639
Gly Gly Trp Ser Leu Asp Leu Gln Met Gln Glu Ala Asp Ile Ser Gly
    175                 180                 185

TAT ATC CCC AAT GGA GAA TGG GAC CTA GTG GGA ATC CCC GGC AAG AGG      687
Tyr Ile Pro Asn Gly Glu Trp Asp Leu Val Gly Ile Pro Gly Lys Arg
190                 195                 200                 205

AGT GAA AGG TTC TAT GAG TGC TGC AAA GAG CCC TAC CCC GAT GTC ACC      735
Ser Glu Arg Phe Tyr Glu Cys Cys Lys Glu Pro Tyr Pro Asp Val Thr
                210                 215                 220

TTC ACA GTG ACC ATG CGC CGC AGG ACG CTC TAC TAT GGC CTC AAC CTG      783
Phe Thr Val Thr Met Arg Arg Arg Thr Leu Tyr Tyr Gly Leu Asn Leu
            225                 230                 235

CTG ATC CCC TGT GTG CTC ATC TCC GCC CTC GCC CTG CTG GTG TTC CTG      831
Leu Ile Pro Cys Val Leu Ile Ser Ala Leu Ala Leu Leu Val Phe Leu
        240                 245                 250

CTT CCT GCA GAT TCC GGG GAG AAG ATT TCC CTG GGG ATA ACA GTC TTA      879
Leu Pro Ala Asp Ser Gly Glu Lys Ile Ser Leu Gly Ile Thr Val Leu
    255                 260                 265

CTC TCT CTT ACC GTC TTC ATG CTG CTC GTG GCT GAG ATC ATG CCC GCA      927
Leu Ser Leu Thr Val Phe Met Leu Leu Val Ala Glu Ile Met Pro Ala
270                 275                 280                 285

ACA TCC GAT TCG GTA CCA TTG ATA GCC CAG TAC TTC GCC AGC ACC ATG      975
Thr Ser Asp Ser Val Pro Leu Ile Ala Gln Tyr Phe Ala Ser Thr Met
                290                 295                 300

ATC ATC GTG GGC CTC TCG GTG GTG GTG ACG GTG ATC GTG CTG CAG TAC     1023
Ile Ile Val Gly Leu Ser Val Val Val Thr Val Ile Val Leu Gln Tyr
            305                 310                 315

CAC CAC CAC GAC CCC GAC GGG GGC AAG ATG CCC AAG TGG ACC AGA GTC     1071
His His His Asp Pro Asp Gly Gly Lys Met Pro Lys Trp Thr Arg Val
        320                 325                 330

ATC CTT CTG AAC TGG TGC GCG TGG TTC CTG CGA ATG AAG AGG CCC GGG     1119
Ile Leu Leu Asn Trp Cys Ala Trp Phe Leu Arg Met Lys Arg Pro Gly
    335                 340                 345

GAG GAC AAG GTG CGC CCG GCC TGC CAG CAC AAG CAG CGG CGC TGC AGC     1167
Glu Asp Lys Val Arg Pro Ala Cys Gln His Lys Gln Arg Arg Cys Ser
350                 355                 360                 365

CTG GCC AGT GTG GAG ATG AGC GCC GTG GCG CCG CCG CCC GCC AGC AAC     1215
Leu Ala Ser Val Glu Met Ser Ala Val Ala Pro Pro Pro Ala Ser Asn
                370                 375                 380

GGG AAC CTG CTG TAC ATC GGC TTC CGC GGC CTG GAC GGC GTG CAC TGT     1263
Gly Asn Leu Leu Tyr Ile Gly Phe Arg Gly Leu Asp Gly Val His Cys
            385                 390                 395

GTC CCG ACC CCC GAC TCT GGG GTA GTG TGT GGC CGC ATG GCC TGC TCC     1311
Val Pro Thr Pro Asp Ser Gly Val Val Cys Gly Arg Met Ala Cys Ser
        400                 405                 410

CCC ACG CAC GAT GAG CAC CTC CTG CAC GGC GGG CAA CCC CCC GAG GGG     1359
Pro Thr His Asp Glu His Leu Leu His Gly Gly Gln Pro Pro Glu Gly
    415                 420                 425

GAC CCG GAC TTG GCC AAG ATC CTG GAG GAG GTC CGC TAC ATT GCC AAT     1407
Asp Pro Asp Leu Ala Lys Ile Leu Glu Glu Val Arg Tyr Ile Ala Asn
430                 435                 440                 445

CGC TTC CGC TGC CAG GAC GAA AGC GAG GCG GTC TGC AGC GAG TGG AAG     1455
Arg Phe Arg Cys Gln Asp Glu Ser Glu Ala Val Cys Ser Glu Trp Lys
                450                 455                 460

TTC GCC GCC TGT GTG GTG GAC CGC CTG TGC CTC ATG GCC TTC TCG GTC     1503
Phe Ala Ala Cys Val Val Asp Arg Leu Cys Leu Met Ala Phe Ser Val
            465                 470                 475
```

```
TTC ACC ATC ATC TGC ACC ATC GGC ATC CTG ATG TCG GCT CCC AAC TTC      1551
Phe Thr Ile Ile Cys Thr Ile Gly Ile Leu Met Ser Ala Pro Asn Phe
        480                 485                 490

GTG GAG GCC GTG TCC AAA GAC TTT GCG TAA CCACGCCTGG TTCTGTACAT GTGG   1605
Val Glu Ala Val Ser Lys Asp Phe Ala  *
        495                 500

AAAACTCACA GATGGGCAAG GCCTTTGGCT TGGCGAGATT TGGGGGTGCT AATCCAGGAC    1665

AGCATTACAC GCCACAACTC CAGTGTTCCC TTCTGGCTGT CAGTCGTGTT GCTTACGGTT    1725

TCTTTGTTAC TTTAGGTAGT AGAATCTCAG CACTTTGTTT CATATTCTCA GATGGGCTGA    1785

TAGATATCCT TGGCACATCC GTACCATCGG TCAGCAGGGC CACTGAGTAG TCATTTTGCC    1845

CATTAGCCCA CTGCCTGGAA AGCCCTTCGG A                                   1876

(2) INFORMATION FOR SEQ ID NO: 12:

(i) SEQUENCE CHARACTERISTICS:
        (A) LENGTH: 446 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 12:

Met Arg Cys Ser Pro Gly Gly Val Trp Ala Ala Ser His Val Ser
1               5                   10                  15

Gln Gly Glu Phe Gln Arg Lys Tyr Lys Glu Val Lys Asn Tyr Asn Pro
            20                  25                  30

Glu Arg Pro Val Ala Asn Asp Ser Gln Pro Thr Val Tyr Phe Ser Ser
        35                  40                  45

Gln Ile Met Asp Val Asp Glu Lys Asn Gln Val Thr Thr Asn Ile Trp
    50                  55                  60

Gln Met Ser Trp Thr Asp His Tyr Gln Trp Asn Val Ser Glu Tyr Pro
65                  70                  75                  80

Gly Val Lys Thr Val Arg Phe Pro Asp Gly Gln Ile Trp Lys Pro Asp
                85                  90                  95

Ile Tyr Asn Ser Ala Asp Glu Arg Phe Asp Ala Thr Phe His Thr Asn
                100                 105                 110

Val Val Asn Ser Ser Gly His Cys Gln Tyr Pro Pro Gly Ile Phe Lys
            115                 120                 125

Ser Ser Cys Tyr Ile Asp Val Arg Trp Phe Pro Phe Asp Val Gln His
        130                 135                 140

Cys Lys Lys Phe Gly Ser Trp Ser Tyr Gly Gly Trp Ser Asp Gln Met
145                 150                 155                 160

Gln Glu Ala Asp Ile Ser Gly Tyr Ile Pro Asn Gly Glu Trp Asp Val
                165                 170                 175

Gly Ile Pro Gly Lys Arg Ser Glu Arg Phe Tyr Glu Cys Cys Lys Glu
            180                 185                 190

Pro Tyr Pro Asp Val Thr Phe Thr Val Thr Met Arg Arg Arg Thr Tyr
        195                 200                 205
```

```
Tyr Gly Asn Ile Pro Cys Val Ile Ser Ala Ala Val Phe Pro Ala Asp
    210                 215                 220
Ser Gly Glu Lys Ile Ser Gly Ile Thr Val Ser Thr Val Phe Met Val
225                 230                 235                 240
Ala Glu Ile Met Pro Ala Thr Ser Asp Ser Val Pro Ile Ala Gln Tyr
                245                 250                 255
Phe Ala Ser Thr Met Ile Ile Val Gly Ser Val Val Thr Val Ile
                260                 265                 270
Val Gln Tyr His His His Asp Pro Asp Gly Gly Lys Met Pro Lys Trp
        275                 280                 285
Thr Arg Val Ile Asn Trp Cys Ala Trp Phe Arg Met Lys Arg Pro Gly
290                 295                 300
Glu Asp Lys Val Arg Pro Ala Cys Gln His Lys Gln Arg Arg Cys Ser
305                 310                 315                 320
Ala Ser Val Glu Met Ser Ala Val Ala Pro Pro Ala Ser Asn Gly
                325                 330                 335
Asn Tyr Ile Gly Phe Arg Gly Asp Gly Val His Cys Val Pro Thr Pro
                340                 345                 350
Asp Ser Gly Val Val Cys Gly Arg Met Ala Cys Ser Pro Thr His Asp
        355                 360                 365
Glu His His Gly Gly Gln Pro Pro Glu Gly Asp Pro Asp Ala Lys Ile
        370                 375                 380
Glu Glu Val Arg Tyr Ile Ala Asn Arg Phe Arg Cys Gln Asp Glu Ser
385                 390                 395                 400
Glu Ala Val Cys Ser Glu Trp Lys Phe Ala Ala Cys Val Val Asp Arg
                405                 410                 415
Cys Met Ala Phe Ser Val Phe Thr Ile Ile Cys Thr Ile Gly Ile Met
                420                 425                 430
Ser Ala Pro Asn Phe Val Glu Ala Val Ser Lys Asp Phe Ala
        435                 440                 445
```

(2) INFORMATION FOR SEQ ID NO: 13:

(i) SEQUENCE CHARACTERISTICS:
        (A) LENGTH: 2448 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 265...1773
        (C) OTHER INFORMATION: beta2 human neuronal nicotinic
            acetylcholine receptor (xi) SEQUENCE DESCRIPTION: SEQ ID NO: 13:

```
CTCCTCCCCC TCACCGTCCC AATTGTATTC CCTGGAAGAG CAGCCGGAAA AGCCTCCGCC      60

TGCTCATACC AGGATAGGCA AGAAGCTGGT TTCTCCTCGC AGCCGGCTCC CTGAGGCCCA     120

GGAACCACCG CGGCGGCCGG CACCACCTGG ACCCAGCTCC AGGCGGGCGC GGCTTCAGCA     180

CCACGGACAG CGCCCCACCC GCGGCCCTCC CCCCGGCGGC GCGCTCCAGC CGGTGTAGGC     240
```

-continued

```
GAGGCAGCGA GCTATGCCCG CGGC ATG GCC CGG CGC TGC GGC CCC GTG GCG         291
                          Met Ala Arg Arg Cys Gly Pro Val Ala
                          1               5

CTG CTC CTT GGC TTC GGC CTC CTC CGG CTG TGC TCA GGG GTG TGG GGT         339
Leu Leu Leu Gly Phe Gly Leu Leu Arg Leu Cys Ser Gly Val Trp Gly
10              15                  20                  25

ACG GAT ACA GAG GAG CGG CTG GTG GAG CAT CTC CTG GAT CCT TCC CGC         387
Thr Asp Thr Glu Glu Arg Leu Val Glu His Leu Leu Asp Pro Ser Arg
            30                  35                  40

TAC AAC AAG CTT ATC CGC CCA GCC ACC AAT GGC TCT GAG CTG GTG ACA         435
Tyr Asn Lys Leu Ile Arg Pro Ala Thr Asn Gly Ser Glu Leu Val Thr
        45                  50                  55

GTA CAG CTT ATG GTG TCA CTG GCC CAG CTC ATC AGT GTG CAT GAG CGG         483
Val Gln Leu Met Val Ser Leu Ala Gln Leu Ile Ser Val His Glu Arg
    60                  65                  70

GAG CAG ATC ATG ACC ACC AAT GTC TGG CTG ACC CAG GAG TGG GAA GAT         531
Glu Gln Ile Met Thr Thr Asn Val Trp Leu Thr Gln Glu Trp Glu Asp
75                  80                  85

TAT CGC CTC ACC TGG AAG CCT GAA GAG TTT GAC AAC ATG AAG AAA GTT         579
Tyr Arg Leu Thr Trp Lys Pro Glu Glu Phe Asp Asn Met Lys Lys Val
90                  95                  100                 105

CGG CTC CCT TCC AAA CAC ATC TGG CTC CCA GAT GTG GTC CTG TAC AAC         627
Arg Leu Pro Ser Lys His Ile Trp Leu Pro Asp Val Val Leu Tyr Asn
            110                 115                 120

AAT GCT GAC GGC ATG TAC GAG GTG TCC TTC TAT TCC AAT GCC GTG GTC         675
Asn Ala Asp Gly Met Tyr Glu Val Ser Phe Tyr Ser Asn Ala Val Val
        125                 130                 135

TCC TAT GAT GGC AGC ATC TTC TGG CTG CCG CCT GCC ATC TAC AAG AGC         723
Ser Tyr Asp Gly Ser Ile Phe Trp Leu Pro Pro Ala Ile Tyr Lys Ser
    140                 145                 150

GCA TGC AAG ATT GAA GTA AAG CAC TTC CCA TTT GAC CAG CAG AAC TGC         771
Ala Cys Lys Ile Glu Val Lys His Phe Pro Phe Asp Gln Gln Asn Cys
155                 160                 165

ACC ATG AAG TTC CGT TCG TGG ACC TAC GAC CGC ACA GAG ATC GAC TTG         819
Thr Met Lys Phe Arg Ser Trp Thr Tyr Asp Arg Thr Glu Ile Asp Leu
170                 175                 180                 185

GTG CTG AAG AGT GAG GTG GCC AGC CTG GAC GAC TTC ACA CCT AGT GGT         867
Val Leu Lys Ser Glu Val Ala Ser Leu Asp Asp Phe Thr Pro Ser Gly
            190                 195                 200

GAG TGG GAC ATC GTG GCG CTG CCG GGC CGG CGC AAC GAG AAC CCC GAC         915
Glu Trp Asp Ile Val Ala Leu Pro Gly Arg Arg Asn Glu Asn Pro Asp
        205                 210                 215

GAC TCT ACG TAC GTG GAC ATC ACG TAT GAC TTC ATC ATT CGC CGC AAG         963
Asp Ser Thr Tyr Val Asp Ile Thr Tyr Asp Phe Ile Ile Arg Arg Lys
    220                 225                 230

CCG CTC TTC TAC ACC ATC AAC CTC ATC ATC CCC TGT GTG CTC ATC ACC        1011
Pro Leu Phe Tyr Thr Ile Asn Leu Ile Ile Pro Cys Val Leu Ile Thr
235                 240                 245

TCG CTA GCC ATC CTT GTC TTC TAC CTG CCA TCC GAC TGT GGC GAG AAG        1059
Ser Leu Ala Ile Leu Val Phe Tyr Leu Pro Ser Asp Cys Gly Glu Lys
250                 255                 260                 265

ATG ACG TTG TGC ATC TCA GTG CTG CTG GCG CTC ACG GTC TTC CTG CTG        1107
Met Thr Leu Cys Ile Ser Val Leu Leu Ala Leu Thr Val Phe Leu Leu
            270                 275                 280

CTC ATC TCC AAG ATC GTG CCT CCC ACC TCC CTC GAC GTG CCG CTC GTC        1155
Leu Ile Ser Lys Ile Val Pro Pro Thr Ser Leu Asp Val Pro Leu Val
        285                 290                 295

GGC AAG TAC CTC ATG TTC ACC ATG GTG CTT GTC ACC TTC TCC ATC GTC        1203
Gly Lys Tyr Leu Met Phe Thr Met Val Leu Val Thr Phe Ser Ile Val
```

```
                300             305             310
ACC AGC GTG TGC GTG CTC AAC GTG CAC CAC CGC TCG CCC ACC ACG CAC       1251
Thr Ser Val Cys Val Leu Asn Val His His Arg Ser Pro Thr Thr His
        315                 320                 325

ACC ATG GCG CCC TGG GTG AAG GTC GTC TTC CTG GAG AAG CTG CCC GCG       1299
Thr Met Ala Pro Trp Val Lys Val Val Phe Leu Glu Lys Leu Pro Ala
330                 335                 340                 345

CTG CTC TTC ATG CAG CAG CCA CGC CAT CAT TGC GCC CGT CAG CGC CTG       1347
Leu Leu Phe Met Gln Gln Pro Arg His His Cys Ala Arg Gln Arg Leu
                350                 355                 360

CGC CTG CGG CGA CGC CAG CGT GAG CGC GAG GGC GCT GGA GCC CTC TTC       1395
Arg Leu Arg Arg Arg Gln Arg Glu Arg Glu Gly Ala Gly Ala Leu Phe
            365                 370                 375

TTC CGC GAA GCC CCA GGG GCC GAC TCC TGC ACG TGC TTC GTC AAC CGC       1443
Phe Arg Glu Ala Pro Gly Ala Asp Ser Cys Thr Cys Phe Val Asn Arg
        380                 385                 390

GCG TCG GTG CAG GGG TTG GCC GGG GCC TTC GGG GCT GAG CCT GCA CCA       1491
Ala Ser Val Gln Gly Leu Ala Gly Ala Phe Gly Ala Glu Pro Ala Pro
395                 400                 405

GTG GCG GGC CCC GGG CGC TCA GGG GAG CCG TGT GGC TGT GGC CTC CGG       1539
Val Ala Gly Pro Gly Arg Ser Gly Glu Pro Cys Gly Cys Gly Leu Arg
410                 415                 420                 425

GAG GCG GTG GAC GGC GTG CGC TTC ATC GCA GAC CAC ATG CGG AGC GAG       1587
Glu Ala Val Asp Gly Val Arg Phe Ile Ala Asp His Met Arg Ser Glu
                430                 435                 440

GAC GAT GAC CAG AGC GTG AGT GAG GAC TGG AAG TAC GTC GCC ATG GTG       1635
Asp Asp Asp Gln Ser Val Ser Glu Asp Trp Lys Tyr Val Ala Met Val
            445                 450                 455

ATC GAC CGC CTC TTC CTC TGG ATC TTT GTC TTT GTC TGT GTC TTT GGC       1683
Ile Asp Arg Leu Phe Leu Trp Ile Phe Val Phe Val Cys Val Phe Gly
        460                 465                 470

ACC ATC GGC ATG TTC CTG CAG CCT CTC TTC CAG AAC TAC ACC ACC ACC       1731
Thr Ile Gly Met Phe Leu Gln Pro Leu Phe Gln Asn Tyr Thr Thr Thr
    475                 480                 485

ACC TTC CTC CAC TCA GAC CAC TCA GCC CCC AGC TCC AAG TGA GGCCCTTCCT   1783
Thr Phe Leu His Ser Asp His Ser Ala Pro Ser Ser Lys *
490                 495                 500

CATCTCCATG CTCTTTCACC CTGCCACCCT CTGCTGCACA GTAGTGTTGG GTGGAGGATG    1843

GACGAGTGAG CTACCAGGAA GAGGGGCGCT GCCCCCACAG ATCCATCCTT TTGCTTCATC    1903

TGGAGTCCCT CCTCCCCCAC GCCTCCATCC ACACACAGCA GCTCCAACCT GGAGGCTGGA    1963

CCAACTGCTT TGTTTTGGCT GCTCTCCATC TCTTGTACCA GCCCAGGCAA TAGTGTTGAG    2023

GAGGGGAGCA AGGCTGCTAA GTGGAAGACA GAGATGGCAG AGCCATCCAC CCTGAGGAGT    2083

GACGGGCAAG GGGCCAGGAA GGGGACAGGA TTGTCTGCTG CCTCCAAGTC ATGGGAGAAG    2143

AGGGGTATAG GACAAGGGGT GGAAGGGCAG GAGCTCACAC CGCACCGGGC TGGCCTGACA    2203

CAATGGTAGC TCTGAAGGGA GGGGAAGAGA GAGGCCTGGG TGTGACCTGA CACCTGCCGC    2263

TGCTTGAGTG GACAGCAGCT GGACTGGGTG GGCCCCACAG TGGTCAGCGA TTCCTGCCAA    2323

GTAGGGTTTA GCCGGGCCCC ATGGTCACAG ACCCCTGGGG GAGGCTTCCA GCTCAGTCCC    2383

ACAGCCCCTT GCTTCTAAGG GATCCAGAGA CCTGCTCCAG ATCCTCTTTC CCCACTGAAG    2443

AATTC                                                                2448

(2) INFORMATION FOR SEQ ID NO: 14:

(i) SEQUENCE CHARACTERISTICS:
        (A) LENGTH: 502 amino acids
```

(B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 14:

```
Met Ala Arg Arg Cys Gly Pro Val Ala Leu Leu Leu Gly Phe Gly Leu
 1               5                  10                  15

Leu Arg Leu Cys Ser Gly Val Trp Gly Thr Asp Thr Glu Glu Arg Leu
            20                  25                  30

Val Glu His Leu Leu Asp Pro Ser Arg Tyr Asn Lys Leu Ile Arg Pro
        35                  40                  45

Ala Thr Asn Gly Ser Glu Leu Val Thr Val Gln Leu Met Val Ser Leu
 50                  55                  60

Ala Gln Leu Ile Ser Val His Glu Arg Glu Gln Ile Met Thr Thr Asn
 65                  70                  75                  80

Val Trp Leu Thr Gln Glu Trp Glu Asp Tyr Arg Leu Thr Trp Lys Pro
                85                  90                  95

Glu Glu Phe Asp Asn Met Lys Lys Val Arg Leu Pro Ser Lys His Ile
            100                 105                 110

Trp Leu Pro Asp Val Val Leu Tyr Asn Asn Ala Asp Gly Met Tyr Glu
        115                 120                 125

Val Ser Phe Tyr Ser Asn Ala Val Val Ser Tyr Asp Gly Ser Ile Phe
    130                 135                 140

Trp Leu Pro Pro Ala Ile Tyr Lys Ser Ala Cys Lys Ile Glu Val Lys
145                 150                 155                 160

His Phe Pro Phe Asp Gln Gln Asn Cys Thr Met Lys Phe Arg Ser Trp
                165                 170                 175

Thr Tyr Asp Arg Thr Glu Ile Asp Leu Val Leu Lys Ser Glu Val Ala
            180                 185                 190

Ser Leu Asp Asp Phe Thr Pro Ser Gly Glu Trp Asp Ile Val Ala Leu
        195                 200                 205

Pro Gly Arg Arg Asn Glu Asn Pro Asp Asp Ser Thr Tyr Val Asp Ile
    210                 215                 220

Thr Tyr Asp Phe Ile Ile Arg Arg Lys Pro Leu Phe Tyr Thr Ile Asn
225                 230                 235                 240

Leu Ile Ile Pro Cys Val Leu Ile Thr Ser Leu Ala Ile Leu Val Phe
                245                 250                 255

Tyr Leu Pro Ser Asp Cys Gly Glu Lys Met Thr Leu Cys Ile Ser Val
            260                 265                 270

Leu Leu Ala Leu Thr Val Phe Leu Leu Leu Ile Ser Lys Ile Val Pro
        275                 280                 285

Pro Thr Ser Leu Asp Val Pro Leu Val Gly Lys Tyr Leu Met Phe Thr
    290                 295                 300

Met Val Leu Val Thr Phe Ser Ile Val Thr Ser Val Cys Val Leu Asn
305                 310                 315                 320

Val His His Arg Ser Pro Thr Thr His Thr Met Ala Pro Trp Val Lys
                325                 330                 335
```

-continued

```
Val Val Phe Leu Glu Lys Leu Pro Ala Leu Leu Phe Met Gln Gln Pro
            340                 345                 350

Arg His His Cys Ala Arg Gln Arg Leu Arg Leu Arg Arg Arg Gln Arg
            355                 360                 365

Glu Arg Glu Gly Ala Gly Ala Leu Phe Phe Arg Glu Ala Pro Gly Ala
    370                 375                 380

Asp Ser Cys Thr Cys Phe Val Asn Arg Ala Ser Val Gln Gly Leu Ala
385                 390                 395                 400

Gly Ala Phe Gly Ala Glu Pro Ala Pro Val Ala Gly Pro Gly Arg Ser
                405                 410                 415

Gly Glu Pro Cys Gly Cys Gly Leu Arg Glu Ala Val Asp Gly Val Arg
                420                 425                 430

Phe Ile Ala Asp His Met Arg Ser Glu Asp Asp Gln Ser Val Ser
            435                 440                 445

Glu Asp Trp Lys Tyr Val Ala Met Val Ile Asp Arg Leu Phe Leu Trp
450                 455                 460

Ile Phe Val Phe Val Cys Val Phe Gly Thr Ile Gly Met Phe Leu Gln
465                 470                 475                 480

Pro Leu Phe Gln Asn Tyr Thr Thr Thr Phe Leu His Ser Asp His
                485                 490                 495

Ser Ala Pro Ser Ser Lys
            500
```

(2) INFORMATION FOR SEQ ID NO: 15:

(i) SEQUENCE CHARACTERISTICS:
        (A) LENGTH: 1925 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 98...1474
        (D) OTHER INFORMATION: beta3 human neuronal nicotinic
           acetylcholine receptor (xi) SEQUENCE DESCRIPTION: SEQ ID NO: 15:

```
TCGGAACCCC TGTATTTTCT TTTCAAAACC CCCTTTTCCA GTGGAAATGC TCTGTTGTTA        60

AAAAGGAAGA AACTGTCTTT CTGAAACTGA CATCACG ATG CTC CCA GAT TTT ATG       115
                                        Met Leu Pro Asp Phe Met
                                          1               5

CTG GTT CTC ATC GTC CTT GGC ATC CCT TCC TCA GCC ACC ACA GGT TTC       163
Leu Val Leu Ile Val Leu Gly Ile Pro Ser Ser Ala Thr Thr Gly Phe
            10                  15                  20

AAC TCA ATC GCC GAA AAT GAA GAT GCC CTC CTC AGA CAT TTG TTC CAA       211
Asn Ser Ile Ala Glu Asn Glu Asp Ala Leu Leu Arg His Leu Phe Gln
        25                  30                  35

GGT TAT CAG AAA TGG GTC CGC CCT GTA TTA CAT TCT AAT GAC ACC ATA       259
Gly Tyr Gln Lys Trp Val Arg Pro Val Leu His Ser Asn Asp Thr Ile
    40                  45                  50

AAA GTA TAT TTT GGA TTG AAA ATA TCC CAG CTT GTA GAT GTG GAT GAA       307
```

```
                                          -continued

Lys Val Tyr Phe Gly Leu Lys Ile Ser Gln Leu Val Asp Val Asp Glu
 55                  60                  65                  70

AAG AAT CAG CTG ATG ACA ACC AAT GTG TGG CTC AAA CAG GAA TGG ACA      355
Lys Asn Gln Leu Met Thr Thr Asn Val Trp Leu Lys Gln Glu Trp Thr
                 75                  80                  85

GAC CAC AAG TTA CGC TGG AAT CCT GAT GAT TAT GGT GGG ATC CAT TCC      403
Asp His Lys Leu Arg Trp Asn Pro Asp Asp Tyr Gly Gly Ile His Ser
             90                  95                 100

ATT AAA GTT CCA TCA GAA TCT CTG TGG CTT CCT GAC ATA GTT CTC TTT      451
Ile Lys Val Pro Ser Glu Ser Leu Trp Leu Pro Asp Ile Val Leu Phe
         105                 110                 115

GAA AAT GCT GAC GGC CGC TTC GAA GGC TCC CTG ATG ACC AAG GTC ATC      499
Glu Asn Ala Asp Gly Arg Phe Glu Gly Ser Leu Met Thr Lys Val Ile
     120                 125                 130

GTG AAA TCA AAC GGA ACT GTT GTC TGG ACC CCT CCC GCC AGC TAC AAA      547
Val Lys Ser Asn Gly Thr Val Val Trp Thr Pro Pro Ala Ser Tyr Lys
135                 140                 145                 150

AGC TCC TGC ACC ATG GAC GTC ACG TTT TTC CCG TTC GAC CGA CAG AAC      595
Ser Ser Cys Thr Met Asp Val Thr Phe Phe Pro Phe Asp Arg Gln Asn
                155                 160                 165

TGC TCC ATG AAG TTT GGA TCC TGG ACT TAT GAT GGC ACC ATG GTT GAC      643
Cys Ser Met Lys Phe Gly Ser Trp Thr Tyr Asp Gly Thr Met Val Asp
            170                 175                 180

CTC ATT TTG ATC AAT GAA AAT GTC GAC AGA AAA GAC TTC TTC GAT AAC      691
Leu Ile Leu Ile Asn Glu Asn Val Asp Arg Lys Asp Phe Phe Asp Asn
        185                 190                 195

GGA GAA TGG GAA ATA CTG AAT GCA AAG GGG ATG AAG GGG AAC AGA AGG      739
Gly Glu Trp Glu Ile Leu Asn Ala Lys Gly Met Lys Gly Asn Arg Arg
    200                 205                 210

GAC GGC GTG TAC TCC TAT CCC TTT ATC ACG TAT TCC TTC GTC CTG AGA      787
Asp Gly Val Tyr Ser Tyr Pro Phe Ile Thr Tyr Ser Phe Val Leu Arg
215                 220                 225                 230

CGC CTG CCT TTA TTC TAT ACC CTC TTT CTC ATC ATC CCC TGC CTG GGG      835
Arg Leu Pro Leu Phe Tyr Thr Leu Phe Leu Ile Ile Pro Cys Leu Gly
                235                 240                 245

CTG TCT TTC CTA ACA GTT CTT GTG TTC TAT TTA CCT TCG GAT GAA GGA      883
Leu Ser Phe Leu Thr Val Leu Val Phe Tyr Leu Pro Ser Asp Glu Gly
            250                 255                 260

GAA AAA CTT TCA TTA TCC ACA TCG GTC TTG GTT TCT CTG ACA GTT TTC      931
Glu Lys Leu Ser Leu Ser Thr Ser Val Leu Val Ser Leu Thr Val Phe
        265                 270                 275

CTT TTA GTG ATT GAA GAA ATC ATC CCA TCG TCT TCC AAA GTC ATT CCT      979
Leu Leu Val Ile Glu Glu Ile Ile Pro Ser Ser Ser Lys Val Ile Pro
    280                 285                 290

CTC ATT GGA GAG TAC CTG CTG TTC ATC ATG ATT TTT GTG ACC CTG TCC     1027
Leu Ile Gly Glu Tyr Leu Leu Phe Ile Met Ile Phe Val Thr Leu Ser
295                 300                 305                 310

ATC ATT GTT ACC GTG TTT GTC ATT AAC GTT CAC CAC AGA TCT TCT TCC     1075
Ile Ile Val Thr Val Phe Val Ile Asn Val His His Arg Ser Ser Ser
                315                 320                 325

ACG TAC CAC CCC ATG GCC CCC TGG GTT AAG AGG CTC TTT CTG CAG AAA     1123
Thr Tyr His Pro Met Ala Pro Trp Val Lys Arg Leu Phe Leu Gln Lys
            330                 335                 340

CTT CCA AAA TTA CTT TGC ATG AAA GAT CAT GTG GAT CGC TAC TCA TCC     1171
Leu Pro Lys Leu Leu Cys Met Lys Asp His Val Asp Arg Tyr Ser Ser
        345                 350                 355

CCA GAG AAA GAG GAG AGT CAA CCA GTA GTG AAA GGC AAA GTC CTC GAA     1219
Pro Glu Lys Glu Glu Ser Gln Pro Val Val Lys Gly Lys Val Leu Glu
    360                 365                 370
```

```
AAA AAG AAA CAG AAA CAG CTT AGT GAT GGA GAA AAA GTT CTA GTT GCT     1267
Lys Lys Lys Gln Lys Gln Leu Ser Asp Gly Glu Lys Val Leu Val Ala
375             380                 385                 390

TTT TTG GAA AAA GCT GCT GAT TCC ATT AGA TAC ATT TCC AGA CAT GTG     1315
Phe Leu Glu Lys Ala Ala Asp Ser Ile Arg Tyr Ile Ser Arg His Val
                395                 400                 405

AAG AAA GAA CAT TTT ATC AGC CAG GTA GTA CAA GAC TGG AAA TTT GTA     1363
Lys Lys Glu His Phe Ile Ser Gln Val Val Gln Asp Trp Lys Phe Val
            410                 415                 420

GCT CAA GTT CTT GAC CGA ATC TTC CTG TGG CTC TTT CTG ATA GTG TCA     1411
Ala Gln Val Leu Asp Arg Ile Phe Leu Trp Leu Phe Leu Ile Val Ser
        425                 430                 435

GTA ACA GGC TCG GTT CTG ATT TTT ACC CCT GCT TTG AAG ATG TGG CTA     1459
Val Thr Gly Ser Val Leu Ile Phe Thr Pro Ala Leu Lys Met Trp Leu
    440                 445                 450

CAT AGT TAC CAT TAG GAATTTAAAA GACATAAGAC TAAATTACAC CTTAGACCTG AC  1516
His Ser Tyr His *
455

ATCTGGCTAT CACACAGACA GAATCCAAAT GCATGTGCTT GTTCTACGAA CCCCGAATGC   1576

GTTGTCTTTG TGGAAATGGA ACATCTCCTC ATGGGAGAAA CTCTGGTAAA TGTGCTCATT   1636

TGTGGTTGCC ATGAGAGTGA GCTGCTTTTA AAGAAAGTGG AGCCTCCTCA GACCCCTGCC   1696

TTGGCTTTCC CAGACATTCA GGGAGGGATC ATAGGTCCAG GCTTGAGCTC ACATGTGGCC   1756

AGAGTGCACA AAAAGCTGTT GCTACTTGGT GGAGGAACAC CTCCTAGAAG CAGCAGGCCT   1816

CGGTGGTGGG GGAGGGGGA TTCACCTGGA ATTAAGGAAG TCTCGGTGTC GAGCTATCTG    1876

TGTGGGCAGA GCCTGGATCT CCCACCCTGC ACTGGCCTCC TTGGTGCCG               1925

(2) INFORMATION FOR SEQ ID NO: 16:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 16:

Met Leu Pro Asp Phe Met Leu Val Leu Ile Val Leu Gly Ile Pro Ser
1               5                   10                  15

Ser Ala Thr Thr Gly Phe Asn Ser Ile Ala Glu Asn Glu Asp Ala Leu
                20                  25                  30

Leu Arg His Leu Phe Gln Gly Tyr Gln Lys Trp Val Arg Pro Val Leu
            35                  40                  45

His Ser Asn Asp Thr Ile Lys Val Tyr Phe Gly Leu Lys Ile Ser Gln
        50                  55                  60

Leu Val Asp Val Asp Glu Lys Asn Gln Leu Met Thr Thr Asn Val Trp
65                  70                  75                  80

Leu Lys Gln Glu Trp Thr Asp His Lys Leu Arg Trp Asn Pro Asp Asp
                85                  90                  95

Tyr Gly Gly Ile His Ser Ile Lys Val Pro Ser Glu Ser Leu Trp Leu
                100                 105                 110
```

```
Pro Asp Ile Val Leu Phe Glu Asn Ala Asp Gly Arg Phe Glu Gly Ser
        115                 120                 125

Leu Met Thr Lys Val Ile Val Lys Ser Asn Gly Thr Val Val Trp Thr
130                 135                 140

Pro Pro Ala Ser Tyr Lys Ser Ser Cys Thr Met Asp Val Thr Phe Phe
145                 150                 155                 160

Pro Phe Asp Arg Gln Asn Cys Ser Met Lys Phe Gly Ser Trp Thr Tyr
                165                 170                 175

Asp Gly Thr Met Val Asp Leu Ile Leu Ile Asn Glu Asn Val Asp Arg
            180                 185                 190

Lys Asp Phe Phe Asp Asn Gly Glu Trp Glu Ile Leu Asn Ala Lys Gly
        195                 200                 205

Met Lys Gly Asn Arg Arg Asp Gly Val Tyr Ser Tyr Pro Phe Ile Thr
        210                 215                 220

Tyr Ser Phe Val Leu Arg Arg Leu Pro Leu Phe Tyr Thr Leu Phe Leu
225                 230                 235                 240

Ile Ile Pro Cys Leu Gly Leu Ser Phe Leu Thr Val Leu Val Phe Tyr
            245                 250                 255

Leu Pro Ser Asp Glu Gly Glu Lys Leu Ser Leu Ser Thr Ser Val Leu
            260                 265                 270

Val Ser Leu Thr Val Phe Leu Leu Val Ile Glu Glu Ile Ile Pro Ser
        275                 280                 285

Ser Ser Lys Val Ile Pro Leu Ile Gly Glu Tyr Leu Leu Phe Ile Met
        290                 295                 300

Ile Phe Val Thr Leu Ser Ile Ile Val Thr Val Phe Val Ile Asn Val
305                 310                 315                 320

His His Arg Ser Ser Ser Thr Tyr His Pro Met Ala Pro Trp Val Lys
                325                 330                 335

Arg Leu Phe Leu Gln Lys Leu Pro Lys Leu Leu Cys Met Lys Asp His
            340                 345                 350

Val Asp Arg Tyr Ser Ser Pro Glu Lys Glu Glu Ser Gln Pro Val Val
        355                 360                 365

Lys Gly Lys Val Leu Glu Lys Lys Gln Lys Gln Leu Ser Asp Gly
        370                 375                 380

Glu Lys Val Leu Val Ala Phe Leu Glu Lys Ala Ala Asp Ser Ile Arg
385                 390                 395                 400

Tyr Ile Ser Arg His Val Lys Lys Glu His Phe Ile Ser Gln Val Val
            405                 410                 415

Gln Asp Trp Lys Phe Val Ala Gln Val Leu Asp Arg Ile Phe Leu Trp
        420                 425                 430

Leu Phe Leu Ile Val Ser Val Thr Gly Ser Val Leu Ile Phe Thr Pro
        435                 440                 445

Ala Leu Lys Met Trp Leu His Ser Tyr His
450                 455

(2) INFORMATION FOR SEQ ID NO: 17:

(i) SEQUENCE CHARACTERISTICS:
        (A) LENGTH: 1915 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO
```

(iv) ANTI-SENSE: NO (v) FRAGMENT TYPE: <Unknown>

(vi) ORIGINAL SOURCE:

(ix) FEATURE:
    (A) NAME/KEY: 5'UTR
    (B) LOCATION: 87...1583
    (D) OTHER INFORMATION: beta4 human neuronal nicotinic
        acetylcholine receptor (xi) SEQUENCE DESCRIPTION: SEQ ID NO: 17:

```
CCGGCGCTCA CTCGACCGCG CGGCTCACGG GTGCCCTGTG ACCCCACAGC GGAGCTCGCG      60

GCGGCTGCCA CCCGGCCCCG CCGGCC ATG AGG CGC GCG CCT TCC CTG GTC CTT     113
                              Met Arg Arg Ala Pro Ser Leu Val Leu
                               1               5

TTC TTC CTG GTC GCC CTT TGC GGG CGC GGG AAC TGC CGC GTG GCC AAT     161
Phe Phe Leu Val Ala Leu Cys Gly Arg Gly Asn Cys Arg Val Ala Asn
 10              15                  20                  25

GCG GAG GAA AAG CTG ATG GAC GAC CTT CTG AAC AAA ACC CGT TAC AAT     209
Ala Glu Glu Lys Leu Met Asp Asp Leu Leu Asn Lys Thr Arg Tyr Asn
                 30                  35                  40

AAC CTG ATC CGC CCA GCC ACC AGC TCC TCA CAG CTC ATC TCC ATC AAG     257
Asn Leu Ile Arg Pro Ala Thr Ser Ser Ser Gln Leu Ile Ser Ile Lys
             45                  50                  55

CTG CAG CTC TCC CTG GCC CAG CTT ATC AGC GTG AAT GAG CGA GAG CAG     305
Leu Gln Leu Ser Leu Ala Gln Leu Ile Ser Val Asn Glu Arg Glu Gln
         60                  65                  70

ATC ATG ACC ACC AAT GTC TGG CTG AAA CAG GAA TGG ACT GAT TAC CGC     353
Ile Met Thr Thr Asn Val Trp Leu Lys Gln Glu Trp Thr Asp Tyr Arg
 75                  80                  85

CTG ACC TGG AAC AGC TCC CGC TAC GAG GGT GTG AAC ATC CTG AGG ATC     401
Leu Thr Trp Asn Ser Ser Arg Tyr Glu Gly Val Asn Ile Leu Arg Ile
 90                  95                 100                 105

CCT GCA AAG CGC ATC TGG TTG CCT GAC ATC GTG CTT TAC AAC AAC GCC     449
Pro Ala Lys Arg Ile Trp Leu Pro Asp Ile Val Leu Tyr Asn Asn Ala
             110                 115                 120

GAC GGG ACC TAT GAG GTG TCT GTC TAC ACC AAC TTG ATA GTC CGG TCC     497
Asp Gly Thr Tyr Glu Val Ser Val Tyr Thr Asn Leu Ile Val Arg Ser
         125                 130                 135

AAC GGC AGC GTC CTG TGG CTG CCC CCT GCC ATC TAC AAG AGC GCC TGC     545
Asn Gly Ser Val Leu Trp Leu Pro Pro Ala Ile Tyr Lys Ser Ala Cys
     140                 145                 150

AAG ATT GAG GTG AAG TAC TTT CCC TTC GAC CAG CAG AAC TGC ACC CTC     593
Lys Ile Glu Val Lys Tyr Phe Pro Phe Asp Gln Gln Asn Cys Thr Leu
 155                 160                 165

AAG TTC CGC TCC TGG ACC TAT GAC CAC ACG GAG ATA GAC ATG GTC CTC     641
Lys Phe Arg Ser Trp Thr Tyr Asp His Thr Glu Ile Asp Met Val Leu
170                 175                 180                 185

ATG ACG CCC ACA GCC AGC ATG GAT GAC TTT ACT CCC AGT GGT GAG TGG     689
Met Thr Pro Thr Ala Ser Met Asp Asp Phe Thr Pro Ser Gly Glu Trp
             190                 195                 200

GAC ATA GTG GCC CTC CCA GGG AGA AGG ACA GTG AAC CCA CAA GAC CCC     737
Asp Ile Val Ala Leu Pro Gly Arg Arg Thr Val Asn Pro Gln Asp Pro
         205                 210                 215

AGC TAC GTG GAC GTG ACT TAC GAC TTC ATC ATC AAG CGC AAG CCT CTG     785
Ser Tyr Val Asp Val Thr Tyr Asp Phe Ile Ile Lys Arg Lys Pro Leu
     220                 225                 230

TTC TAC ACC ATC AAC CTC ATC ATC CCC TGC GTG CTC ACC ACC TTG CTG     833
Phe Tyr Thr Ile Asn Leu Ile Ile Pro Cys Val Leu Thr Thr Leu Leu
```

```
                235                  240                  245
GCC ATC CTC GTC TTC TAC CTG CCA TCC GAC TGC GGC GAG AAG ATG ACA        881
Ala Ile Leu Val Phe Tyr Leu Pro Ser Asp Cys Gly Glu Lys Met Thr
250                 255                 260                 265

CTG TGC ATC TCA GTG CTG CTG GCA CTG ACA TTC TTC CTG CTG CTC ATC        929
Leu Cys Ile Ser Val Leu Leu Ala Leu Thr Phe Phe Leu Leu Leu Ile
                270                 275                 280

TCC AAG ATC GTG CCA CCC ACC TCC CTC GAT GTG CCT CTC ATC GGC AAG        977
Ser Lys Ile Val Pro Pro Thr Ser Leu Asp Val Pro Leu Ile Gly Lys
            285                 290                 295

TAC CTC ATG TTC ACC ATG GTG CTG GTC ACC TTC TCC ATC GTC ACC AGC       1025
Tyr Leu Met Phe Thr Met Val Leu Val Thr Phe Ser Ile Val Thr Ser
        300                 305                 310

GTC TGT GTG CTC AAT GTG CAC CAC CGC TCG CCC AGC ACC CAC ACC ATG       1073
Val Cys Val Leu Asn Val His His Arg Ser Pro Ser Thr His Thr Met
    315                 320                 325

GCA CCC TGG GTC AAG CGC TGC TTC CTG CAC AAG CTG CCT ACC TTC CTC       1121
Ala Pro Trp Val Lys Arg Cys Phe Leu His Lys Leu Pro Thr Phe Leu
330                 335                 340                 345

TTC ATG AAG CGC CCT GGC CCC GAC AGC AGC CCG GCC AGA GCC TTC CCG       1169
Phe Met Lys Arg Pro Gly Pro Asp Ser Ser Pro Ala Arg Ala Phe Pro
                350                 355                 360

CCC AGC AAG TCA TGC GTG ACC AAG CCC GAG GCC ACC GCC ACC TCC ACC       1217
Pro Ser Lys Ser Cys Val Thr Lys Pro Glu Ala Thr Ala Thr Ser Thr
            365                 370                 375

AGC CCC TCC AAC TTC TAT GGG AAC TCC ATG TAC TTT GTG AAC CCC GCC       1265
Ser Pro Ser Asn Phe Tyr Gly Asn Ser Met Tyr Phe Val Asn Pro Ala
        380                 385                 390

TCT GCA GCT TCC AAG TCT CCA GCC GGC TCT ACC CCG GTG GCT ATC CCC       1313
Ser Ala Ala Ser Lys Ser Pro Ala Gly Ser Thr Pro Val Ala Ile Pro
    395                 400                 405

AGG GAT TTC TGG CTG CGG TCC TCT GGG AGG TTC CGA CAG GAT GTG CAG       1361
Arg Asp Phe Trp Leu Arg Ser Ser Gly Arg Phe Arg Gln Asp Val Gln
410                 415                 420                 425

GAG GCA TTA GAA GGT GTC AGC TTC ATC GCC CAG CAC ATG AAG AAT GAC       1409
Glu Ala Leu Glu Gly Val Ser Phe Ile Ala Gln His Met Lys Asn Asp
                430                 435                 440

GAT GAA GAC CAG AGT GTC GTT GAG GAC TGG AAG TAC GTG GCT ATG GTG       1457
Asp Glu Asp Gln Ser Val Val Glu Asp Trp Lys Tyr Val Ala Met Val
            445                 450                 455

GTG GAC CGG CTG TTC CTG TGG GTG TTC ATG TTT GTG TGC GTC CTG GGC       1505
Val Asp Arg Leu Phe Leu Trp Val Phe Met Phe Val Cys Val Leu Gly
        460                 465                 470

ACT GTG GGG CTC TTC CTA CCG CCC CTC TTC CAG ACC CAT GCA GCT TCT       1553
Thr Val Gly Leu Phe Leu Pro Pro Leu Phe Gln Thr His Ala Ala Ser
    475                 480                 485

GAG GGG CCC TAC GCT GCC CAG CGT GAC TGA GGGCCCCTG GGTTGTGGG TGAG      1607
Glu Gly Pro Tyr Ala Ala Gln Arg Asp  *
490                 495

AGGATGTGAG TGGCCGGGTG GGCACTTTGC TGCTTCTTTC TGGGTTGTGG CCGATGAGGC     1667

CCTAAGTAAA TATGTGAGCA TTGGCCATCA ACCCCATCAA ACCAGCCACA GCCGTGGAAC     1727

AGGCAAGGAT GGGGGCCTGG GCTGTCCTCT CTGAATGCCT TGGAGGGATC CAGGAAGCC      1787

CCAGTAGGAG GGAGCTTCAG ACAGTTCAAT TCTGGCCTGT CTTCCTTCCC TGCACCGGGC     1847

AATGGGGATA AAGATGACTT CGTAGCAGCA CCTACTATGC TTCAGGCATG GTGCCGGCCT     1907

GCCTCTCC                                                              1915
```

(2) INFORMATION FOR SEQ ID NO: 18:

(i) SEQUENCE CHARACTERISTICS:
　　　　(A) LENGTH: 498 amino acids
　　　　(B) TYPE: amino acid
　　　　(C) STRANDEDNESS: single
　　　　(D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 18:

```
Met Arg Arg Ala Pro Ser Leu Val Leu Phe Leu Val Ala Leu Cys
 1               5                  10                  15

Gly Arg Gly Asn Cys Arg Val Ala Asn Ala Glu Glu Lys Leu Met Asp
                20                  25                  30

Asp Leu Leu Asn Lys Thr Arg Tyr Asn Asn Leu Ile Arg Pro Ala Thr
            35                  40                  45

Ser Ser Ser Gln Leu Ile Ser Ile Lys Leu Gln Leu Ser Leu Ala Gln
50                  55                  60

Leu Ile Ser Val Asn Glu Arg Glu Gln Ile Met Thr Thr Asn Val Trp
65                  70                  75                  80

Leu Lys Gln Glu Trp Thr Asp Tyr Arg Leu Thr Trp Asn Ser Ser Arg
                85                  90                  95

Tyr Glu Gly Val Asn Ile Leu Arg Ile Pro Ala Lys Arg Ile Trp Leu
                100                 105                 110

Pro Asp Ile Val Leu Tyr Asn Asn Ala Asp Gly Thr Tyr Glu Val Ser
            115                 120                 125

Val Tyr Thr Asn Leu Ile Val Arg Ser Asn Gly Ser Val Leu Trp Leu
130                 135                 140

Pro Pro Ala Ile Tyr Lys Ser Ala Cys Lys Ile Glu Val Lys Tyr Phe
145                 150                 155                 160

Pro Phe Asp Gln Gln Asn Cys Thr Leu Lys Phe Arg Ser Trp Thr Tyr
                165                 170                 175

Asp His Thr Glu Ile Asp Met Val Leu Met Thr Pro Thr Ala Ser Met
            180                 185                 190

Asp Asp Phe Thr Pro Ser Gly Glu Trp Asp Ile Val Ala Leu Pro Gly
            195                 200                 205

Arg Arg Thr Val Asn Pro Gln Asp Pro Ser Tyr Val Asp Val Thr Tyr
210                 215                 220

Asp Phe Ile Ile Lys Arg Lys Pro Leu Phe Tyr Thr Ile Asn Leu Ile
225                 230                 235                 240

Ile Pro Cys Val Leu Thr Thr Leu Leu Ala Ile Leu Val Phe Tyr Leu
                245                 250                 255

Pro Ser Asp Cys Gly Glu Lys Met Thr Leu Cys Ile Ser Val Leu Leu
            260                 265                 270

Ala Leu Thr Phe Phe Leu Leu Leu Ile Ser Lys Ile Val Pro Pro Thr
            275                 280                 285

Ser Leu Asp Val Pro Leu Ile Gly Lys Tyr Leu Met Phe Thr Met Val
290                 295                 300

Leu Val Thr Phe Ser Ile Val Thr Ser Val Cys Val Leu Asn Val His
305                 310                 315                 320
```

```
His Arg Ser Pro Ser Thr His Thr Met Ala Pro Trp Val Lys Arg Cys
                325                 330                 335

Phe Leu His Lys Leu Pro Thr Phe Leu Phe Met Lys Arg Pro Gly Pro
                340                 345                 350

Asp Ser Ser Pro Ala Arg Ala Phe Pro Pro Ser Lys Ser Cys Val Thr
                355                 360                 365

Lys Pro Glu Ala Thr Ala Thr Ser Thr Ser Pro Ser Asn Phe Tyr Gly
            370                 375                 380

Asn Ser Met Tyr Phe Val Asn Pro Ala Ser Ala Ser Lys Ser Pro
385                 390                 395                 400

Ala Gly Ser Thr Pro Val Ala Ile Pro Arg Asp Phe Trp Leu Arg Ser
                405                 410                 415

Ser Gly Arg Phe Arg Gln Asp Val Gln Ala Leu Glu Gly Val Ser
                420                 425                 430

Phe Ile Ala Gln His Met Lys Asn Asp Asp Glu Asp Gln Ser Val Val
                435                 440                 445

Glu Asp Trp Lys Tyr Val Ala Met Val Val Asp Arg Leu Phe Leu Trp
            450                 455                 460

Val Phe Met Phe Val Cys Val Leu Gly Thr Val Gly Leu Phe Leu Pro
465                 470                 475                 480

Pro Leu Phe Gln Thr His Ala Ala Ser Glu Gly Pro Tyr Ala Ala Gln
                485                 490                 495

Arg Asp (2) INFORMATION FOR SEQ ID NO: 19:

(i) SEQUENCE CHARACTERISTICS:
        (A) LENGTH: 1698 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE: <Unknown>

(vi) ORIGINAL SOURCE:

(ix) FEATURE:
        (A) NAME/KEY: 5'UTR
        (B) LOCATION: 143...1582
        (D) OTHER INFORMATION: alpha6 (del 74-88) subunit
            human neuronal nicotinic acetylcholine rec.

(xi) SEQUENCE DESCRIPTION: SEQ ID NO: 19:

CGGGTTTTGA TTTCTGAGAA GACACACACG GATTGCAGTG GGCTTCTGAT GATGTCAAGG      60

TTGGATGCAT GTGGCTGACT GATAGCTCTT TGTTTTCCAC AATCCTTTGC CTAGGAAAAA     120

GGAATCCAAG TGTGTTTTAA CC ATG CTG ACC AGC AAG GGG CAG GGA TTC CTT     172
                         Met Leu Thr Ser Lys Gly Gln Gly Phe Leu
                          1               5                  10

CAT GGG GGC TTG TGT CTC TGG CTG TGT GTG TTC ACA CCT TTC TTT AAA     220
His Gly Gly Leu Cys Leu Trp Leu Cys Val Phe Thr Pro Phe Phe Lys
                15                  20                  25

GGC TGT GTG GGC TGT GCA ACT GAG GAG AGG CTC TTC CAC AAA CTG TTT     268
Gly Cys Val Gly Cys Ala Thr Glu Glu Arg Leu Phe His Lys Leu Phe
            30                  35                  40
```

```
                                                                    -continued TCT CAT TAC AAC CAG TTC ATC AGG CCT GTG GAA AAC GTT TCC GAC CCT       316
Ser His Tyr Asn Gln Phe Ile Arg Pro Val Glu Asn Val Ser Asp Pro
        45                  50                  55

GTC ACG GTA CAC TTT GAA GTG GCC ATC ACC CAG CTG GCC AAC GTG ATC       364
Val Thr Val His Phe Glu Val Ala Ile Thr Gln Leu Ala Asn Val Ile
    60                  65                  70

TGG AAT GAT TAT AAA TTG CGC TGG GAT CCA ATG GAA TAT GAT GGC ATT       412
Trp Asn Asp Tyr Lys Leu Arg Trp Asp Pro Met Glu Tyr Asp Gly Ile
75                  80                  85                  90

GAG ACT CTT CGC GTT CCT GCA GAT AAG ATT TGG AAG CCC GAC ATT GTT       460
Glu Thr Leu Arg Val Pro Ala Asp Lys Ile Trp Lys Pro Asp Ile Val
                95                  100                 105

CTC TAT AAC AAT GCT GTT GGT GAC TTC CAA GTA GAA GGC AAA ACA AAA       508
Leu Tyr Asn Asn Ala Val Gly Asp Phe Gln Val Glu Gly Lys Thr Lys
            110                 115                 120

GCT CTT CTT AAA TAC AAT GGC ATG ATA ACC TGG ACT CCA CCA GCT ATT       556
Ala Leu Leu Lys Tyr Asn Gly Met Ile Thr Trp Thr Pro Pro Ala Ile
        125                 130                 135

TTT AAG AGT TCC TGC CCT ATG GAT ATC ACC TTT TTC CCT TTT GAT CAT       604
Phe Lys Ser Ser Cys Pro Met Asp Ile Thr Phe Phe Pro Phe Asp His
    140                 145                 150

CAA AAC TGT TCC CTA AAA TTT GGT TCC TGG ACG TAT GAC AAA GCT GAA       652
Gln Asn Cys Ser Leu Lys Phe Gly Ser Trp Thr Tyr Asp Lys Ala Glu
155                 160                 165                 170

ATT GAT CTT CTA ATC ATT GGA TCA AAA GTG GAT ATG AAT GAT TTT TGG       700
Ile Asp Leu Leu Ile Ile Gly Ser Lys Val Asp Met Asn Asp Phe Trp
                175                 180                 185

GAA AAC AGT GAA TGG GAA ATC ATT GAT GCC TCT GGC TAC AAA CAT GAC       748
Glu Asn Ser Glu Trp Glu Ile Ile Asp Ala Ser Gly Tyr Lys His Asp
            190                 195                 200

ATC AAA TAC AAC TGT TGT GAA GAG ATA TAC ACA GAT ATA ACC TAT TCT       796
Ile Lys Tyr Asn Cys Cys Glu Glu Ile Tyr Thr Asp Ile Thr Tyr Ser
        205                 210                 215

TTC TAC ATT AGA AGA TTG CCG ATG TTT TAC ACG ATT AAT CTG ATC ATC       844
Phe Tyr Ile Arg Arg Leu Pro Met Phe Tyr Thr Ile Asn Leu Ile Ile
    220                 225                 230

CCT TGT CTC TTT ATT TCA TTT CTA ACC GTG TTG GTC TTT TAC CTT CCT       892
Pro Cys Leu Phe Ile Ser Phe Leu Thr Val Leu Val Phe Tyr Leu Pro
235                 240                 245                 250

TCG GAC TGT GGT GAA AAA GTG ACG CTT TGT ATT TCA GTC CTG CTT TCT       940
Ser Asp Cys Gly Glu Lys Val Thr Leu Cys Ile Ser Val Leu Leu Ser
                255                 260                 265

CTG ACT GTG TTT TTG CTG GTC ATC ACA GAA ACC ATC CCA TCC ACA TCT       988
Leu Thr Val Phe Leu Leu Val Ile Thr Glu Thr Ile Pro Ser Thr Ser
            270                 275                 280

CTG GTG GTC CCA CTG GTG GGT GAG TAC CTG CTG TTC ACC ATG ATC TTT      1036
Leu Val Val Pro Leu Val Gly Glu Tyr Leu Leu Phe Thr Met Ile Phe
        285                 290                 295

GTC ACA CTG TCC ATC GTG GTG ACT GTG TTT GTG TTG AAC ATA CAC TAC      1084
Val Thr Leu Ser Ile Val Val Thr Val Phe Val Leu Asn Ile His Tyr
    300                 305                 310

CGC ACC CCA ACC ACG CAC ACA ATG CCC AGG TGG GTG AAG ACA GTT TTC      1132
Arg Thr Pro Thr Thr His Thr Met Pro Arg Trp Val Lys Thr Val Phe
315                 320                 325                 330

CTG AAG CTG CTG CCC CAG GTC CTG CTG ATG AGG TGG CCT CTG GAC AAG      1180
Leu Lys Leu Leu Pro Gln Val Leu Leu Met Arg Trp Pro Leu Asp Lys
                335                 340                 345

ACA AGG GGC ACA GGC TCT GAT GCA GTG CCC AGA GGC CTT GCC AGG AGG      1228
Thr Arg Gly Thr Gly Ser Asp Ala Val Pro Arg Gly Leu Ala Arg Arg
            350                 355                 360
```

```
CCT GCC AAA GGC AAG CTT GCA AGC CAT GGG GAA CCC AGA CAT CTT AAA      1276
Pro Ala Lys Gly Lys Leu Ala Ser His Gly Glu Pro Arg His Leu Lys
        365                 370                 375

GAA TGC TTC CAT TGT CAC AAA TCA AAT GAG CTT GCC ACA AGC AAG AGA      1324
Glu Cys Phe His Cys His Lys Ser Asn Glu Leu Ala Thr Ser Lys Arg
    380                 385                 390

AGA TTA AGT CAT CAG CCA TTA CAG TGG GTG GTG GAA AAT TCG GAG CAC      1372
Arg Leu Ser His Gln Pro Leu Gln Trp Val Val Glu Asn Ser Glu His
395                 400                 405                 410

TCG CCT GAA GTT GAA GAT GTG ATT AAC AGT GTT CAG TTC ATA GCA GAA      1420
Ser Pro Glu Val Glu Asp Val Ile Asn Ser Val Gln Phe Ile Ala Glu
                415                 420                 425

AAC ATG AAG AGC CAC AAT GAA ACC AAG GAG GTA GAA GAT GAC TGG AAA      1468
Asn Met Lys Ser His Asn Glu Thr Lys Glu Val Glu Asp Asp Trp Lys
            430                 435                 440

TAC GTG GCC ATG GTG GTG GAC AGA GTA TTT CTT TGG GTA TTT ATA ATT      1516
Tyr Val Ala Met Val Val Asp Arg Val Phe Leu Trp Val Phe Ile Ile
                445                 450                 455

GTC TGT GTA TTT GGA ACT GCA GGG CTA TTT CTA CAG CCA CTA CTT GGG      1564
Val Cys Val Phe Gly Thr Ala Gly Leu Phe Leu Gln Pro Leu Leu Gly
460                 465                 470

AAC ACA GGA AAA TCT TAA AATGTATTTT CTTTTATGTT CAGAAATTTA CAGACACCA   1621
Asn Thr Gly Lys Ser *
475                 480

TATTTGTTCT GCATTCCCTG CCACAAGGAA AGGAAAGCAA AGGCTTCCCA CCCAAGTCCC   1681

CCATCTGCTA AAACCCG                                                   1698

(2) INFORMATION FOR SEQ ID NO: 20:

(i) SEQUENCE CHARACTERISTICS:
        (A) LENGTH: 479 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 20:

Met Leu Thr Ser Lys Gly Gln Gly Phe Leu His Gly Gly Leu Cys Leu
1               5                   10                  15

Trp Leu Cys Val Phe Thr Pro Phe Phe Lys Gly Cys Val Gly Cys Ala
            20                  25                  30

Thr Glu Glu Arg Leu Phe His Lys Leu Phe Ser His Tyr Asn Gln Phe
        35                  40                  45

Ile Arg Pro Val Glu Asn Val Ser Asp Pro Val Thr Val His Phe Glu
    50                  55                  60

Val Ala Ile Thr Gln Leu Ala Asn Val Ile Trp Asn Asp Tyr Lys Leu
65                  70                  75                  80

Arg Trp Asp Pro Met Glu Tyr Asp Gly Ile Glu Thr Leu Arg Val Pro
                85                  90                  95

Ala Asp Lys Ile Trp Lys Pro Asp Ile Val Leu Tyr Asn Asn Ala Val
            100                 105                 110
```

```
Gly Asp Phe Gln Val Glu Gly Lys Thr Lys Ala Leu Leu Lys Tyr Asn
        115                 120                 125

Gly Met Ile Thr Trp Thr Pro Pro Ala Ile Phe Lys Ser Ser Cys Pro
        130                 135                 140

Met Asp Ile Thr Phe Phe Pro Phe Asp His Gln Asn Cys Ser Leu Lys
145                 150                 155                 160

Phe Gly Ser Trp Thr Tyr Asp Lys Ala Glu Ile Asp Leu Leu Ile Ile
                165                 170                 175

Gly Ser Lys Val Asp Met Asn Asp Phe Trp Glu Asn Ser Glu Trp Glu
                180                 185                 190

Ile Ile Asp Ala Ser Gly Tyr Lys His Asp Ile Lys Tyr Asn Cys Cys
        195                 200                 205

Glu Glu Ile Tyr Thr Asp Ile Thr Tyr Ser Phe Tyr Ile Arg Arg Leu
        210                 215                 220

Pro Met Phe Tyr Thr Ile Asn Leu Ile Ile Pro Cys Leu Phe Ile Ser
225                 230                 235                 240

Phe Leu Thr Val Leu Val Phe Tyr Leu Pro Ser Asp Cys Gly Glu Lys
                245                 250                 255

Val Thr Leu Cys Ile Ser Val Leu Leu Ser Leu Thr Val Phe Leu Leu
                260                 265                 270

Val Ile Thr Glu Thr Ile Pro Ser Thr Ser Leu Val Val Pro Leu Val
                275                 280                 285

Gly Glu Tyr Leu Leu Phe Thr Met Ile Phe Val Thr Leu Ser Ile Val
        290                 295                 300

Val Thr Val Phe Val Leu Asn Ile His Tyr Arg Thr Pro Thr Thr His
305                 310                 315                 320

Thr Met Pro Arg Trp Val Lys Thr Val Phe Leu Lys Leu Leu Pro Gln
                325                 330                 335

Val Leu Leu Met Arg Trp Pro Leu Asp Lys Thr Arg Gly Thr Gly Ser
                340                 345                 350

Asp Ala Val Pro Arg Gly Leu Ala Arg Arg Pro Ala Lys Gly Lys Leu
        355                 360                 365

Ala Ser His Gly Glu Pro Arg His Leu Lys Glu Cys Phe His Cys His
        370                 375                 380

Lys Ser Asn Glu Leu Ala Thr Ser Lys Arg Arg Leu Ser His Gln Pro
385                 390                 395                 400

Leu Gln Trp Val Val Glu Asn Ser Glu His Ser Pro Glu Val Glu Asp
                405                 410                 415

Val Ile Asn Ser Val Gln Phe Ile Ala Glu Asn Met Lys Ser His Asn
                420                 425                 430

Glu Thr Lys Glu Val Glu Asp Asp Trp Lys Tyr Val Ala Met Val Val
        435                 440                 445

Asp Arg Val Phe Leu Trp Val Phe Ile Ile Val Cys Val Phe Gly Thr
        450                 455                 460

Ala Gly Leu Phe Leu Gln Pro Leu Leu Gly Asn Thr Gly Lys Ser
465                 470                 475
```